US010435435B2

(12) United States Patent
Pettit et al.

(10) Patent No.: US 10,435,435 B2
(45) Date of Patent: Oct. 8, 2019

(54) QUINSTATIN COMPOUNDS

(71) Applicants: George Robert Pettit, Paradise Valley, AZ (US); Noeleen Melody, Mesa, AZ (US)

(72) Inventors: George Robert Pettit, Paradise Valley, AZ (US); Noeleen Melody, Mesa, AZ (US)

(73) Assignee: THE ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/747,077

(22) PCT Filed: Jul. 22, 2016

(86) PCT No.: PCT/US2016/043519
§ 371 (c)(1),
(2) Date: Jan. 23, 2018

(87) PCT Pub. No.: WO2017/019489
PCT Pub. Date: Feb. 2, 2017

(65) Prior Publication Data
US 2018/0371012 A1     Dec. 27, 2018

Related U.S. Application Data

(60) Provisional application No. 62/196,890, filed on Jul. 24, 2015, provisional application No. 62/359,313, filed on Jul. 7, 2016.

(51) Int. Cl.
| | |
|---|---|
| *C07K 7/02* | (2006.01) |
| *C07K 5/02* | (2006.01) |
| *C07K 5/062* | (2006.01) |
| *A61P 35/00* | (2006.01) |
| *A61K 38/00* | (2006.01) |

(52) U.S. Cl.
CPC ............ *C07K 5/0205* (2013.01); *A61P 35/00* (2018.01); *C07K 5/06043* (2013.01); *C07K 7/02* (2013.01); *A61K 38/00* (2013.01)

(58) Field of Classification Search
None
See application file for complete search history.

(56) References Cited

U.S. PATENT DOCUMENTS

| | | |
|---|---|---|
| 5,654,399 A | 8/1997 | Sakakibara et al. |
| 5,767,237 A | 6/1998 | Sakakibara et al. |
| 6,214,345 B1 | 4/2001 | Firestone et al. |
| 7,745,394 B2 | 6/2010 | Doronina et al. |
| 9,044,518 B2 | 6/2015 | Pettit et al. |
| 9,249,186 B2 | 2/2016 | Doroski et al. |
| 9,539,342 B2 | 1/2017 | Pettit et al. |
| 2004/0254343 A1* | 12/2004 | Miyazaki ............. C07K 5/0205 530/330 |
| 2013/0190248 A1 | 7/2013 | Mendelsohn et al. |
| 2013/0203496 A1 | 8/2013 | Lewis et al. |
| 2014/0023666 A1* | 1/2014 | Pettit .................... C07D 401/12 424/179.1 |
| 2017/0100491 A1 | 4/2017 | Pettit et al. |
| 2018/0030095 A1 | 2/2018 | Pettit et al. |

FOREIGN PATENT DOCUMENTS

WO    WO 2008103277    2/2008

OTHER PUBLICATIONS

Amsberry, K., et al., J. Org. Chem., 1990, 55, 5867-5877.
Baba, A., et al. J. Med. Chem. 1996, 39, 5176-5182.
Bai, R., et al., Mol. Pharmacol., 2009, 75, 218-226.
Flygare, J. et al., Chem. Biol. Drug Des., 2013, 81, 113-121.
Hay, M. et al., Bioorg. Med. Chem. Lett., 1999, 9, 2237-2242.
Maderna, A. and Leveret C., Mol. Pharmaceutics, 2015, 12, 1798-1812.
Micovic, V.M. and Mihailovic, M.L., J. Org. Chem.,1953, 18, 1190-1200.
Newman, M.S. and Fukunaga, T., J. Am. Chem. Soc., 1960, 82, 693-696.
Pettit et al., J. Nat. Prod., 2018, 81, 451-457.
Pettit et al., J. Nat. Prod., 2017, 80, 2447-2452.
Pettit, G.R., et al., J. Nat. Prod., 2015, 78, 476-485.
Rodrigues, M.L., et al., Curr Biol., 1995, 2, 223-227.
Sievers, E.L. and Senter, P.D. Annu. Rev. Med. 2013, 64, 15-29.
Storm et al., J. Am. Chem. Soc., 1972, 94, 5815-5825.
Younes, A., et al., J. Clin. Oncol., 2012, 30, 2183-3019.
Doronina, S.O., et al., Nat. Biotech. 2003, 21(7), 778-784.
International Preliminary Report on Patentability dated Feb. 8, 2018 in International Patent Application No. PCT/US2016/043519.
International Search Report and Written Opinion dated Oct. 5, 2016 in International Application No. PCT/US2016/043519.
Kung Suterland, M, et al., J. Biol. Chem, 2006, 281, 10540-10547.
Mordant, C., et al., Tetrahedron, 2007, 63, 6115-6123.
Pettit, G.R., "Progress in the Chemistry of Organic Natural Products 70: The Dolastatins", Springer-Verlag, 1997.
Pettit, G.R., et al., Anti-Cancer Drug Desgin, 1995, 10, 529-544.
Pettit, G.R., et al., Anti-Cancer Drug Design, 1998, 13, 243-277.
Pettit, G.R., et al., J. Chem. Soc., Perkin Trans. 1, 1996, 859-863.
Pettit, G.R., et al., J. Nat. Prod. 2011, 74, 962-968.
Pettit, G.R., et al., J. Am. Chem. Soc., 1987, 109, 6883-6885.
Pettit, G.R., et al., J. Org. Chem. 1994, 59, 6287-6295.
Pettit, G.R., International Oncology Updates: Marine Anticancer Compounds in the Era of Targeted Therapies, Permanyer Publications, Barcelona, 2009, 19-49.
Rodrigues et al., Chem. Biol., 1995, 2, 223-227.

\* cited by examiner

*Primary Examiner* — Lianko G Garyu
(74) *Attorney, Agent, or Firm* — Byrne Poh LLP; Nina R. Horan

(57) ABSTRACT

The present disclosure relates to Quinstatin compounds, pharmaceutical compositions comprising such compounds, kits, and methods for using such compounds or pharmaceutical compositions.

18 Claims, No Drawings

QUINSTATIN COMPOUNDS

BACKGROUND OF THE INVENTION

The discovery[1b] of the dolastatin series[1c,d] of cancer cell growth inhibitors contained in the wide ranging sea hare *Dolabella auricularia* revealed a new and very promising vista for anticancer drug discovery. That's proved to be broadly confirmed by clinical development,[2] of dolastatin 10 (1) and 15[2c] and structural modifications designated auristatins.[3] By 2001, auristatin E (2a)[3b] began preclinical development as a very promising antibody drug conjugate (ADC) by linkage to a CD30 monoclonal antibody. Soon the development continued, employing the cancer biology equivalent desmethyl auristatin E (2b).

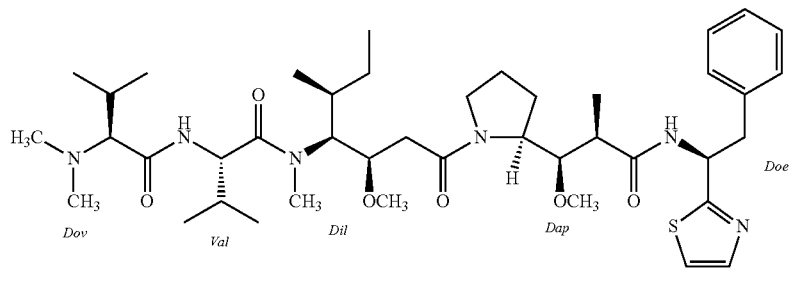

1, dolastatin 10

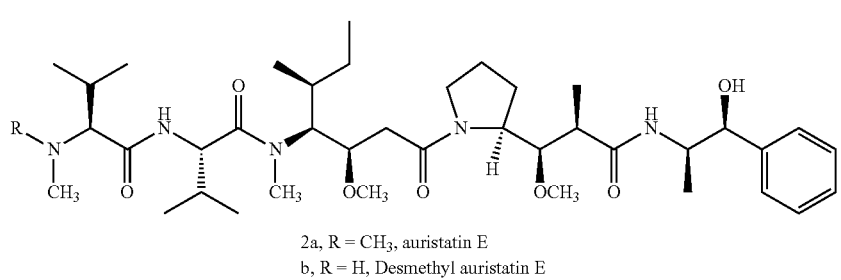

2a, R = CH₃, auristatin E
b, R = H, Desmethyl auristatin E

Presently the resulting ADC anticancer drug[4a-e] designated ADCETRIS has been approved for use in 50 countries, for example, treatment of patients with refractory Hodgkin's lymphoma and large cell lymphoma thereby resulting in remarkable complete remissions.[4d] Those early clinical results have inspired a massive current research effort to link auristatin (2b) to other monoclonal antibodies[4a,b] representing a spectrum of cancer types. In parallel, considerable research has been continued to discover structural modifications of dolastatin 10 that would provide powerful cancer cell growth inhibition without the high toxic level, and provide a much better therapeutic range for inspired ADC use. Citation of any reference in this section is not to be construed as an admission that such reference is prior art to the present disclosure.

BRIEF SUMMARY OF THE INVENTION

The present disclosure relates to Quinstatin compounds, pharmaceutical compositions comprising such compounds, kits, and methods for using such compounds or pharmaceutical compositions. The compounds of the present disclosure contain an easily derivatizable group for conjugation to monoclonal antibodies. The compounds have, or are believed to have, suitable cancer cell growth inhibition values.

In a first embodiment, the present disclosure provides a compound of formula (I):

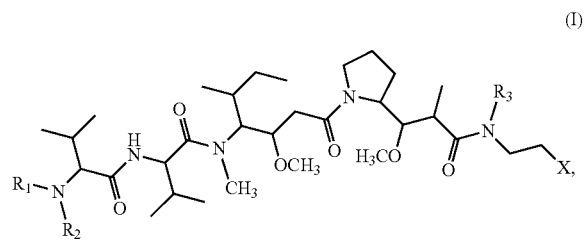

(I)

or a pharmaceutically acceptable salt thereof, wherein $R_1$ is selected from H, $(C_1-C_6)$ alkyl, $(C_2-C_6)$ alkenyl, $(C_2-C_6)$ alkynyl, a Protecting Group or a Linker Unit;

$R_2$ is selected from H, $(C_1-C_6)$ alkyl, $(C_2-C_6)$ alkenyl or $(C_2-C_6)$ alkynyl;

$R_3$ is H or $(C_1-C_6)$ alkyl; and

X is a bicyclic heterocyclic ring system selected from quinolinyl, isoquinolinyl, 1,5-naphthyridinyl, quinoxalinyl, quinazolinyl, cinnolinyl, 2,7-naphthyridinyl, 1,8-naphthyridinyl, 2,6-naphthyridinyl, phthalazinyl, 2H-chromenyl, 1H-1,5-benzodiazepinyl, 1,2,3-benzotriazinyl and 2,5-benzodiazocinyl, wherein the bicyclic heterocyclic ring system is unsubstituted or substituted with 1, 2 or 3 substituent(s) selected from $(C_1-C_6)$ alkoxy, methylene dioxy, hydroxyl, O-Protecting Group and O-Linker Unit.

In a second embodiment, the present disclosure provides a compound of formula (Ia),

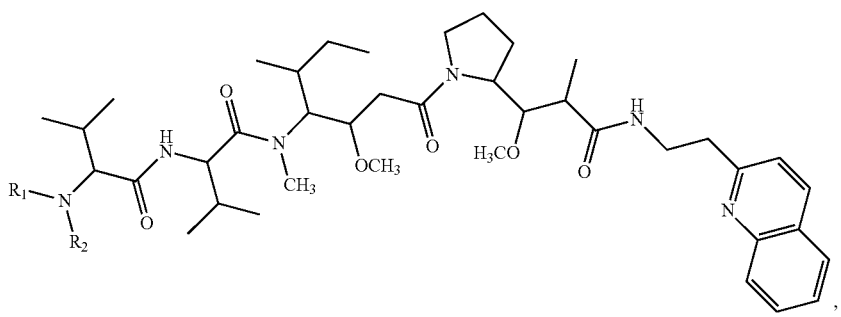

(Ia)

or a pharmaceutically acceptable salt thereof, wherein $R_1$ is selected from H, $(C_1-C_6)$ alkyl, $(C_2-C_6)$ alkenyl, $(C_2-C_6)$ alkynyl, a Protecting Group or a Linker Unit; and $R_2$ is selected from H, $(C_1-C_6)$ alkyl, $(C_2-C_6)$ alkenyl or $(C_2-C_6)$ alkynyl.

In a third embodiment, the present disclosure provides a compound of formula (Ib),

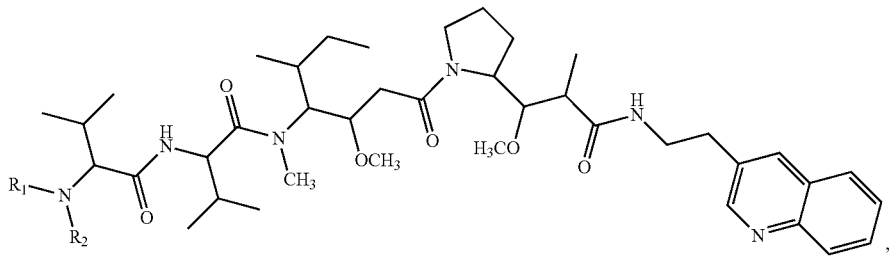

(Ib)

or a pharmaceutically acceptable salt thereof, wherein $R_1$ is selected from H, $(C_1-C_6)$ alkyl, $(C_2-C_6)$ alkenyl, $(C_2-C_6)$ alkynyl, a Protecting Group or a Linker Unit; and $R_2$ is selected from H, $(C_1-C_6)$ alkyl, $(C_2-C_6)$ alkenyl or $(C_2-C_6)$ alkynyl.

In a fourth embodiment, the present disclosure provides a compound of formula (Ic),

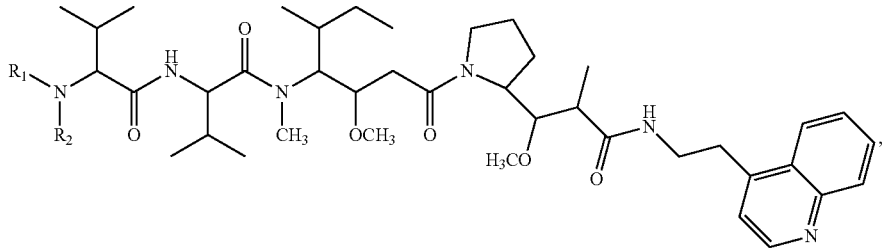

(Ic)

or a pharmaceutically acceptable salt thereof, wherein $R_1$ is selected from H, $(C_1-C_6)$ alkyl, $(C_2-C_6)$ alkenyl, $(C_2-C_6)$ alkynyl, a Protecting Group or a Linker Unit; and $R_2$ is selected from H, $(C_1-C_6)$ alkyl, $(C_2-C_6)$ alkenyl or $(C_2-C_6)$ alkynyl.

In a fifth embodiment, the present disclosure provides a compound of formula (Id), (Id)

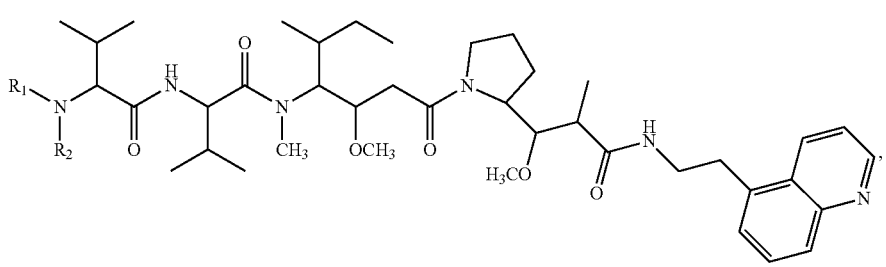

or a pharmaceutically acceptable salt thereof, wherein $R_1$ is selected from H, $(C_1-C_6)$ alkyl, $(C_2-C_6)$ alkenyl, $(C_2-C_6)$ alkynyl, a Protecting Group or a Linker Unit; and $R_2$ is selected from H, $(C_1-C_6)$ alkyl, $(C_2-C_6)$ alkenyl or $(C_2-C_6)$ alkynyl.

In a sixth embodiment, the present disclosure provides a compound of formula (Ie), (Ie)

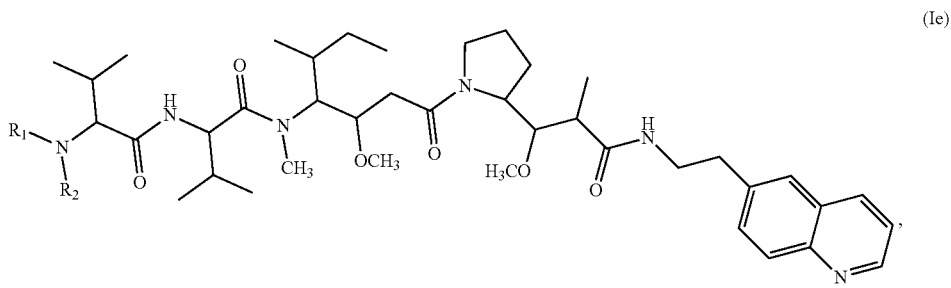

or a pharmaceutically acceptable salt thereof, wherein $R_1$ is selected from H, $(C_1-C_6)$ alkyl, $(C_2-C_6)$ alkenyl, $(C_2-C_6)$ alkynyl, a Protecting Group or a Linker Unit; and $R_2$ is selected from H, $(C_1-C_6)$ alkyl, $(C_2-C_6)$ alkenyl or $(C_2-C_6)$ alkynyl.

In a seventh embodiment, the present disclosure provides a compound of formula (If), (If)

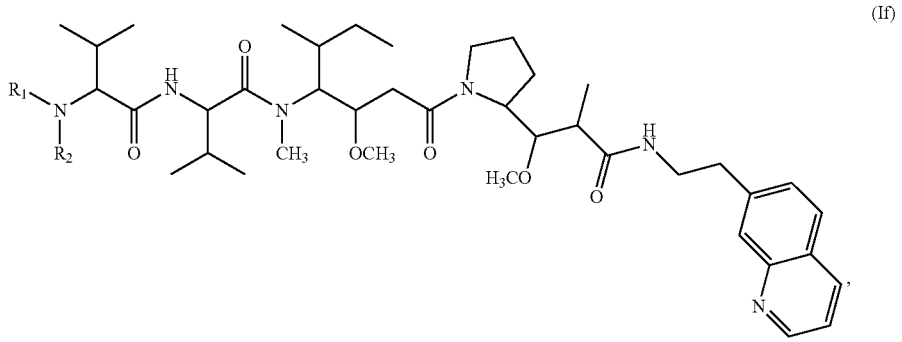

or a pharmaceutically acceptable salt thereof, wherein $R_1$ is selected from H, $(C_1-C_6)$ alkyl, $(C_2-C_6)$ alkenyl, $(C_2-C_6)$ alkynyl, a Protecting Group or a Linker Unit; and $R_2$ is selected from H, $(C_1-C_6)$ alkyl, $(C_2-C_6)$ alkenyl or $(C_2-C_6)$ alkynyl.

In an eighth embodiment, the present disclosure provides a compound of formula (Ig),

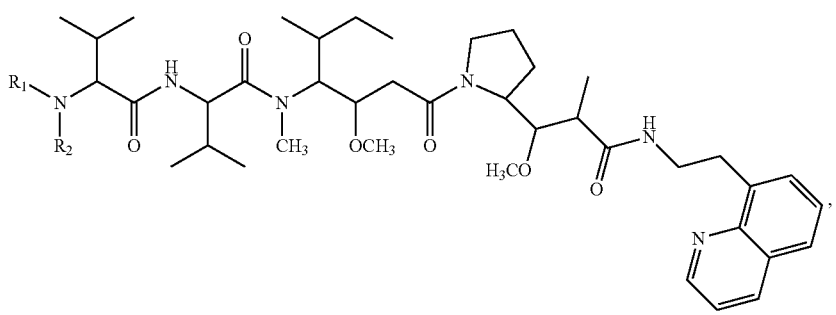

or a pharmaceutically acceptable salt thereof, wherein $R_1$ is selected from H, ($C_1$-$C_6$) alkyl, ($C_2$-$C_6$) alkenyl, ($C_2$-$C_6$) alkynyl, a Protecting Group or a Linker Unit; and $R_2$ is selected from H, ($C_1$-$C_6$) alkyl, ($C_2$-$C_6$) alkenyl or ($C_2$-$C_6$) alkynyl.

The compounds of this disclosure have or are believed to have highly favorable cancer cell growth inhibitory activities. In particular, compounds of formula (I) exhibit nanomolar cancer cell growth inhibitory activities. See Example 6. The cancer cell growth inhibitory activities are significantly improved relative to auristatin AQ.

DETAILED DESCRIPTION OF THE INVENTION

The invention includes the following:

(1.) A compound of formula (I),

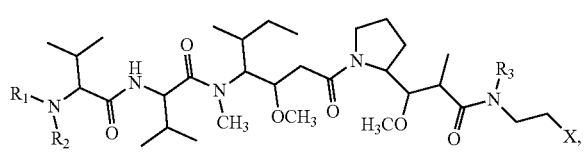

or a pharmaceutically acceptable salt thereof, wherein $R_1$ is selected from H, ($C_1$-$C_6$) alkyl, ($C_2$-$C_6$) alkenyl, ($C_2$-$C_6$) alkynyl, a Protecting Group or a Linker Unit;

$R_2$ is selected from H, ($C_1$-$C_6$) alkyl, ($C_2$-$C_6$) alkenyl or ($C_2$-$C_6$) alkynyl;

$R_3$ is H or ($C_1$-$C_6$) alkyl; and

X is a bicyclic heterocyclic ring system selected from quinolinyl, isoquinolinyl, 1,5-naphthyridinyl, quinoxalinyl, quinazolinyl, cinnolinyl, 2,7-naphthyridinyl, 1,8-naphthyridinyl, 2,6-naphthyridinyl, phthalazinyl, 2H-chromenyl, 1H-1,5-benzodiazepinyl, 1,2,3-benzotriazinyl and 2,5-benzodiazocinyl, wherein the bicyclic heterocyclic ring system is unsubstituted or substituted with 1, 2 or 3 substituent(s) selected from ($C_1$-$C_6$) alkoxy, methylene dioxy, hydroxyl, O-Protecting Group and O-Linker Unit.

(2.) The compound of the above (1.), wherein X is quinolinyl.

(3.) The compound of the above (1.), wherein X is isoquinolinyl.

(4.) The compound of the above (1.), wherein X is 2-quinolinyl, 3-quinolinyl, 6-quinolinyl, 7-quinolinyl or 8-quinolinyl.

(5.) The compound of the above (1.), wherein X is 2-quinolinyl, 6-quinolinyl, 7-quinolinyl or 8-quinolinyl.

(6.) A compound of formula (Ia),

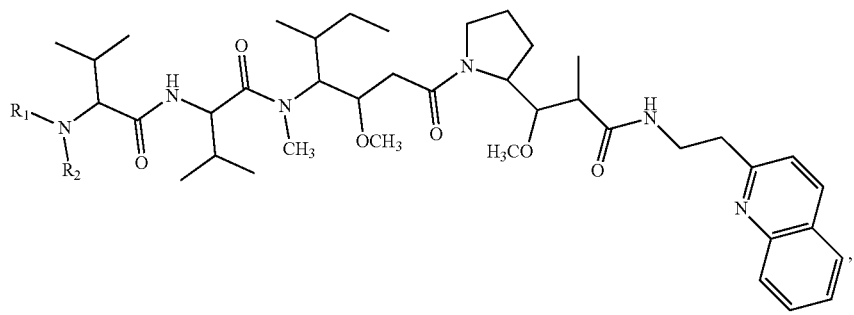

or a pharmaceutically acceptable salt thereof, wherein $R_1$ is selected from H, $(C_1-C_6)$ alkyl, $(C_2-C_6)$ alkenyl, $(C_2-C_6)$ alkynyl, a Protecting Group or a Linker Unit; and $R_2$ is selected from H, $(C_1-C_6)$ alkyl, $(C_2-C_6)$ alkenyl or $(C_2-C_6)$ alkynyl.

(7.) The compound of the above (6.), wherein $R_1$ is H, $(C_1-C_6)$ alkyl or a Linker Unit.

(8.) The compound of the above (6.), wherein $R_1$ is H or $(C_1-C_6)$ alkyl.

(9.) The compound of the above (6.), wherein $R_1$ is H or a Linker Unit.

(10.) The compound of the above (6.), wherein $R_1$ is $(C_1-C_6)$ alkyl or a Linker Unit.

(11.) The compound of the above (6.), wherein $R_1$ is H, methyl or a Linker Unit.

(12.) The compound of the above (6.), wherein $R_1$ is H or methyl.

(13.) The compound of the above (6.), wherein $R_1$ is H or a Linker Unit.

(14.) The compound of the above (6.), wherein $R_1$ is methyl or a Linker Unit.

(15.) The compound of the above (6.), wherein $R_1$ is H.

(16.) The compound of the above (6.), wherein $R_1$ is methyl.

(17.) The compound of the above (6.), wherein $R_1$ is a Linker Unit.

(18.) The compound of any of the above (6.) to (17.), wherein $R_2$ is H or $(C_1-C_6)$ alkyl.

(19.) The compound of any of the above (6.) to (17.), wherein $R_2$ is H or methyl.

(20.) The compound of any of the above (6.) to (17.), wherein $R_2$ is H.

(21.) The compound of any of the above (6.) to (17.), wherein $R_2$ is $(C_1-C_6)$ alkyl.

(22.) The compound of any of the above (6.) to (17.), wherein $R_2$ is methyl.

(23.) A compound of formula (Ib), or a pharmaceutically acceptable salt thereof, wherein $R_1$ is selected from H, $(C_1-C_6)$ alkyl, $(C_2-C_6)$ alkenyl, $(C_2-C_6)$ alkynyl, a Protecting Group or a Linker Unit; and $R_2$ is selected from H, $(C_1-C_6)$ alkyl, $(C_2-C_6)$ alkenyl or $(C_2-C_6)$ alkynyl.

(24.) The compound of the above (23.), wherein $R_1$ is H, $(C_1-C_6)$ alkyl or a Linker Unit.

(25.) The compound of the above (23.), wherein $R_1$ is H or $(C_1-C_6)$ alkyl.

(26.) The compound of the above (23.), wherein $R_1$ is H or a Linker Unit.

(27.) The compound of the above (23.), wherein $R_1$ is $(C_1-C_6)$ alkyl or a Linker Unit.

(28.) The compound of the above (23.), wherein $R_1$ is H, methyl or a Linker Unit.

(29.) The compound of the above (23.), wherein $R_1$ is H or methyl.

(30.) The compound of the above (23.), wherein $R_1$ is H or a Linker Unit.

(31.) The compound of the above (23.), wherein $R_1$ is methyl or a Linker Unit.

(32.) The compound of the above (23.), wherein $R_1$ is H.

(33.) The compound of the above (23.), wherein $R_1$ is methyl.

(34.) The compound of the above (23.), wherein $R_1$ is a Linker Unit.

(35.) The compound of any of the above (23.) to (34.), wherein $R_2$ is H or $(C_1-C_6)$ alkyl.

(36.) The compound of any of the above (23.) to (34.), wherein $R_2$ is H or methyl.

(37.) The compound of any of the above (23.) to (34.), wherein $R_2$ is H.

(38.) The compound of any of the above (23.) to (34.), wherein $R_2$ is $(C_1-C_6)$ alkyl.

(39.) The compound of any of the above (23.) to (34.), wherein $R_2$ is methyl.

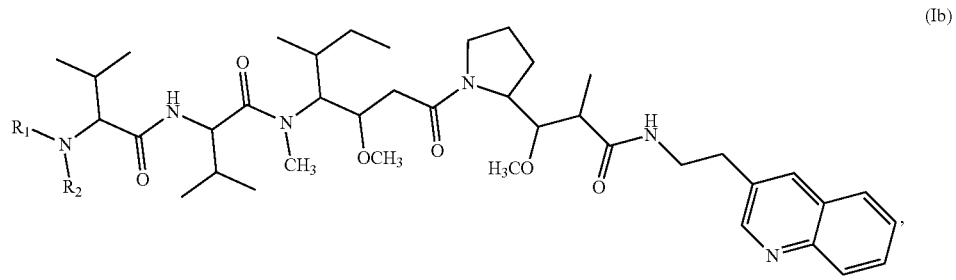

(Ib)

(40.) A compound of formula (Ic),

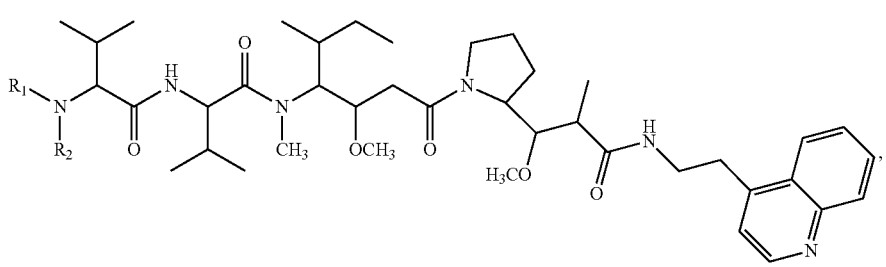

or a pharmaceutically acceptable salt thereof, wherein
$R_1$ is selected from H, $(C_1\text{-}C_6)$ alkyl, $(C_2\text{-}C_6)$ alkenyl, $(C_2\text{-}C_6)$ alkynyl, a Protecting Group or a Linker Unit; and
$R_2$ is selected from H, $(C_1\text{-}C_6)$ alkyl, $(C_2\text{-}C_6)$ alkenyl or $(C_2\text{-}C_6)$ alkynyl.

(41.) The compound of the above (40.), wherein $R_1$ is H, $(C_1\text{-}C_6)$ alkyl or a Linker Unit.
(42.) The compound of the above (40.), wherein $R_1$ is H or $(C_1\text{-}C_6)$ alkyl.
(43.) The compound of the above (40.), wherein $R_1$ is H or a Linker Unit.
(44.) The compound of the above (40.), wherein $R_1$ is $(C_1\text{-}C_6)$ alkyl or a Linker Unit.
(45.) The compound of the above (40.), wherein $R_1$ is H, methyl or a Linker Unit.
(46.) The compound of the above (40.), wherein $R_1$ is H or methyl.
(47.) The compound of the above (40.), wherein $R_1$ is H or a Linker Unit.
(48.) The compound of the above (40.), wherein $R_1$ is methyl or a Linker Unit.
(49.) The compound of the above (40.), wherein $R_1$ is H.
(50.) The compound of the above (40.), wherein $R_1$ is methyl.
(51.) The compound of the above (40.), wherein $R_1$ is a Linker Unit.
(52.) The compound of any of the above (40.) to (51.), wherein $R_2$ is H or $(C_1\text{-}C_6)$ alkyl.
(53.) The compound of any of the above (40.) to (51.), wherein $R_2$ is H or methyl.
(54.) The compound of any of the above (40.) to (51.), wherein $R_2$ is H.
(55.) The compound of any of the above (40.) to (51.), wherein $R_2$ is $(C_1\text{-}C_6)$ alkyl.
(56.) The compound of any of the above (40.) to (51.), wherein $R_2$ is methyl.
(57.) A compound of formula (Id),

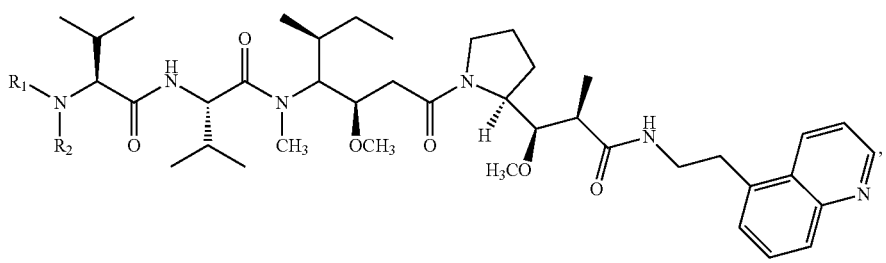

or a pharmaceutically acceptable salt thereof, wherein
$R_1$ is selected from H, $(C_1\text{-}C_6)$ alkyl, $(C_2\text{-}C_6)$ alkenyl, $(C_2\text{-}C_6)$ alkynyl, a Protecting Group or a Linker Unit; and
$R_2$ is selected from H, $(C_1\text{-}C_6)$ alkyl, $(C_2\text{-}C_6)$ alkenyl or $(C_2\text{-}C_6)$ alkynyl.

(58.) The compound of the above (57.), wherein $R_1$ is H, $(C_1\text{-}C_6)$ alkyl or a Linker Unit.
(59.) The compound of the above (57.), wherein $R_1$ is H or $(C_1\text{-}C_6)$ alkyl.
(60.) The compound of the above (57.), wherein $R_1$ is H or a Linker Unit.
(61.) The compound of the above (57.), wherein $R_1$ is $(C_1\text{-}C_6)$ alkyl or a Linker Unit.
(62.) The compound of the above (57.), wherein $R_1$ is H, methyl or a Linker Unit.
(63.) The compound of the above (57.), wherein $R_1$ is H or methyl.
(64.) The compound of the above (57.), wherein $R_1$ is H or a Linker Unit.
(65.) The compound of the above (57.), wherein $R_1$ is methyl or a Linker Unit.
(66.) The compound of the above (57.), wherein $R_1$ is H.
(67.) The compound of the above (57.), wherein $R_1$ is methyl.
(68.) The compound of the above (57.), wherein $R_1$ is a Linker Unit.
(69.) The compound of any of the above (57.) to (68.), wherein $R_2$ is H or $(C_1\text{-}C_6)$ alkyl.
(70.) The compound of any of the above (57.) to (68.), wherein $R_2$ is H or methyl.
(71.) The compound of any of the above (57.) to (68.), wherein $R_2$ is H.
(72.) The compound of any of the above (57.) to (68.), wherein $R_2$ is $(C_1\text{-}C_6)$ alkyl.
(73.) The compound of any of the above (57.) to (68.), wherein $R_2$ is methyl.

(74.) A compound of formula (Ie),

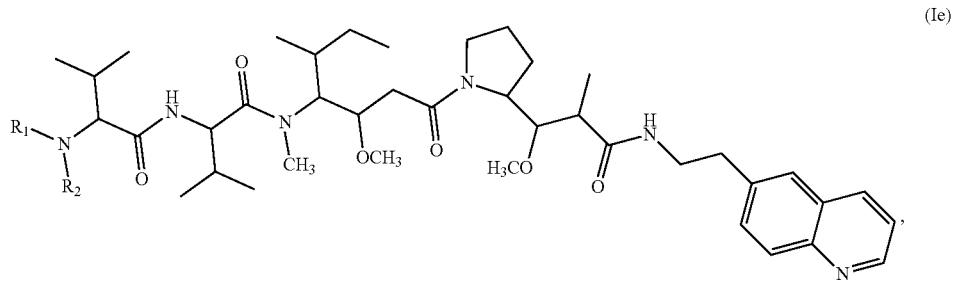

or a pharmaceutically acceptable salt thereof, wherein
$R_1$ is selected from H, $(C_1-C_6)$ alkyl, $(C_2-C_6)$ alkenyl, $(C_2-C_6)$ alkynyl, a Protecting Group or a Linker Unit; and
$R_2$ is selected from H, $(C_1-C_6)$ alkyl, $(C_2-C_6)$ alkenyl or $(C_2-C_6)$ alkynyl.

(75.) The compound of the above (74.), wherein $R_1$ is H, $(C_1-C_6)$ alkyl or a Linker Unit.
(76.) The compound of the above (74.), wherein $R_1$ is H or $(C_1-C_6)$ alkyl.
(77.) The compound of the above (74.), wherein $R_1$ is H or a Linker Unit.
(78.) The compound of the above (74.), wherein $R_1$ is $(C_1-C_6)$ alkyl or a Linker Unit.
(79.) The compound of the above (74.), wherein $R_1$ is H, methyl or a Linker Unit.
(80.) The compound of the above (74.), wherein $R_1$ is H or methyl.
(81.) The compound of the above (74.), wherein $R_1$ is H or a Linker Unit.
(82.) The compound of the above (74.), wherein $R_1$ is methyl or a Linker Unit.
(83.) The compound of the above (74.), wherein $R_1$ is H.
(84.) The compound of the above (74.), wherein $R_1$ is methyl.
(85.) The compound of the above (74.), wherein $R_1$ is a Linker Unit.
(86.) The compound of any of the above (74.) to (85.), wherein $R_2$ is H or $(C_1-C_6)$ alkyl.
(87.) The compound of any of the above (74.) to (85.), wherein $R_2$ is H or methyl.
(88.) The compound of any of the above (74.) to (85.), wherein $R_2$ is H.
(89.) The compound of any of the above (74.) to (85.), wherein $R_2$ is $(C_1-C_6)$ alkyl.
(90.) The compound of any of the above (74.) to (85.), wherein $R_2$ is methyl.
(91.) A compound of formula (If), or a pharmaceutically acceptable salt thereof, wherein
$R_1$ is selected from H, $(C_1-C_6)$ alkyl, $(C_2-C_6)$ alkenyl, $(C_2-C_6)$ alkynyl, a Protecting Group or a Linker Unit; and
$R_2$ is selected from H, $(C_1-C_6)$ alkyl, $(C_2-C_6)$ alkenyl or $(C_2-C_6)$ alkynyl.

(92.) The compound of the above (91.), wherein $R_1$ is H, $(C_1-C_6)$ alkyl or a Linker Unit.
(93.) The compound of the above (91.), wherein $R_1$ is H or $(C_1-C_6)$ alkyl.
(94.) The compound of the above (91.), wherein $R_1$ is H or a Linker Unit.
(95.) The compound of the above (91.), wherein $R_1$ is $(C_1-C_6)$ alkyl or a Linker Unit.
(96.) The compound of the above (91.), wherein $R_1$ is H, methyl or a Linker Unit.
(97.) The compound of the above (91.), wherein $R_1$ is H or methyl.
(98.) The compound of the above (91.), wherein $R_1$ is H or a Linker Unit.
(99.) The compound of the above (91.), wherein $R_1$ is methyl or a Linker Unit.
(100.) The compound of the above (91.), wherein $R_1$ is H.
(101.) The compound of the above (91.), wherein $R_1$ is methyl.
(102.) The compound of the above (91.), wherein $R_1$ is a Linker Unit.
(103.) The compound of any of the above (91.) to 102.), wherein $R_2$ is H or $(C_1-C_6)$ alkyl.
(104.) The compound of any of the above (91.) to (102.), wherein $R_2$ is H or methyl.
(105.) The compound of any of the above (91.) to (102.), wherein $R_2$ is H.
(106.) The compound of any of the above (91.) to (102.), wherein $R_2$ is $(C_1-C_6)$ alkyl.
(107.) The compound of any of the above (91.) to (102.), wherein $R_2$ is methyl.

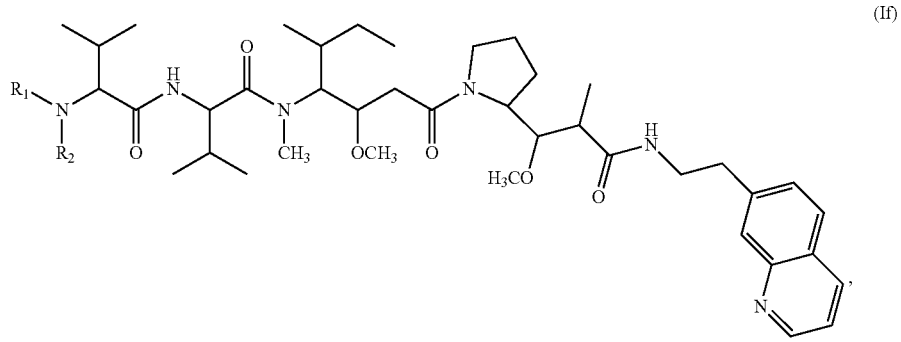

(108.) A compound of formula (Ig),

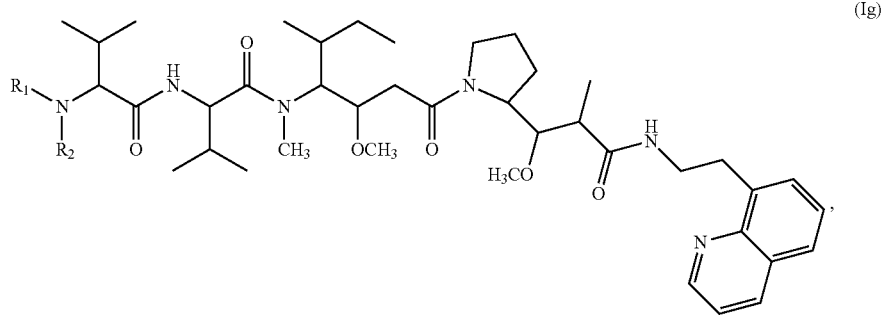

or a pharmaceutically acceptable salt thereof, wherein R$_1$ is selected from H, (C$_1$-C$_6$) alkyl, (C$_2$-C$_6$) alkenyl, (C$_2$-C$_6$) alkynyl, a Protecting Group or a Linker Unit; and R$_2$ is selected from H, (C$_1$-C$_6$) alkyl, (C$_2$-C$_6$) alkenyl or (C$_2$-C$_6$) alkynyl.

(109.) The compound of the above (108.), wherein R$_1$ is H, (C$_1$-C$_6$) alkyl or a Linker Unit.

(110.) The compound of the above (108.), wherein R$_1$ is H or (C$_1$-C$_6$) alkyl.

(111.) The compound of the above (108.), wherein R$_1$ is H or a Linker Unit.

(112.) The compound of the above (108.), wherein R$_1$ is (C$_1$-C$_6$) alkyl or a Linker Unit.

(113.) The compound of the above (108.), wherein R$_1$ is H, methyl or a Linker Unit.

(114.) The compound of the above (108.), wherein R$_1$ is H or methyl.

(115.) The compound of the above (108.), wherein R$_1$ is H or a Linker Unit.

(116.) The compound of the above (108.), wherein R$_1$ is methyl or a Linker Unit.

(117.) The compound of the above (108.), wherein R$_1$ is H.

(118.) The compound of the above (108.), wherein R$_1$ is methyl.

(119.) The compound of the above (108.), wherein R$_1$ is a Linker Unit.

(120.) The compound of any of the above (108.) to (119.), wherein R$_2$ is H or (C$_1$-C$_6$) alkyl.

(121.) The compound of any of the above (108.) to (119.), wherein R$_2$ is H or methyl.

(122.) The compound of any of the above (108.) to (119.), wherein R$_2$ is H.

(123.) The compound of any of the above (108.) to (119.), wherein R$_2$ is (C$_1$-C$_6$) alkyl.

(124.) The compound of any of the above (108.) to (119.), wherein R$_2$ is methyl.

(125.) The compound of any of the above (1.) to (124.), wherein the Linker Unit comprises a cleavable linker.

(126.) The compound of the above (125.), wherein the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage.

(127.) The compound of the above (126.), wherein the cleavable linker comprises a glycosidic bond, a hydrazone, a cathepsin-B-cleavable peptide, a disulfide or an ester bond.

(128.) The compound of any one of claims 1 to 124, wherein the Linker Unit has formula:

A$_a$W$_w$Y$_y$, wherein

A$_a$ is maleimidocaproyl, W$_w$ is Valine-Citrulline and Y$_y$ is p-aminobenzyloxycarbonyl.

(129.) The compound of the above (126.), wherein the cleavable linker comprises glucuronide.

(130.) The compound of any of the above (1) to (124) or (128.), wherein the Linker Unit comprises a monoclonal antibody.

(131.) A compound selected from the group consisting of:

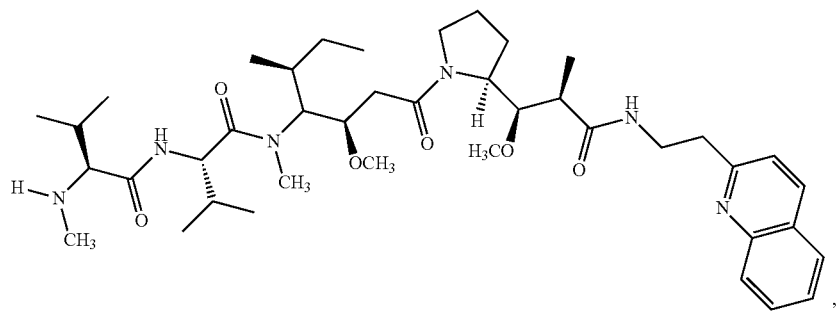

-continued
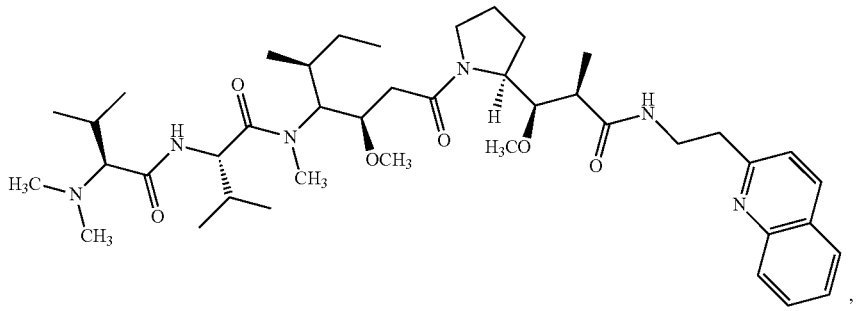
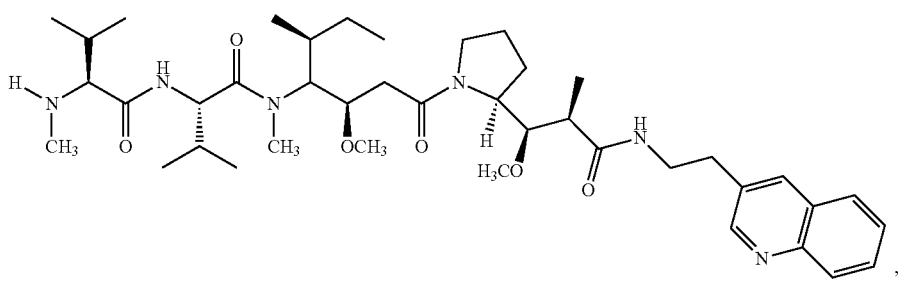
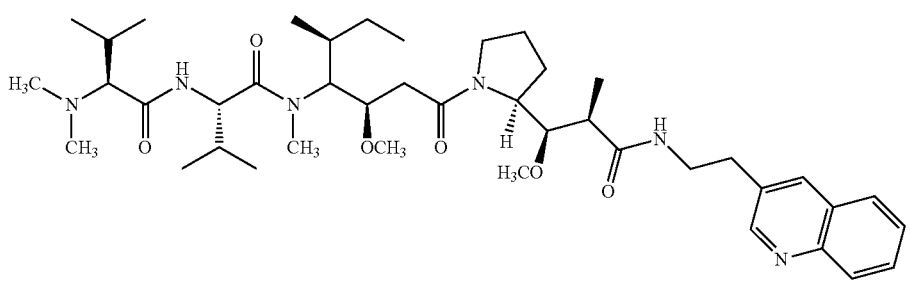
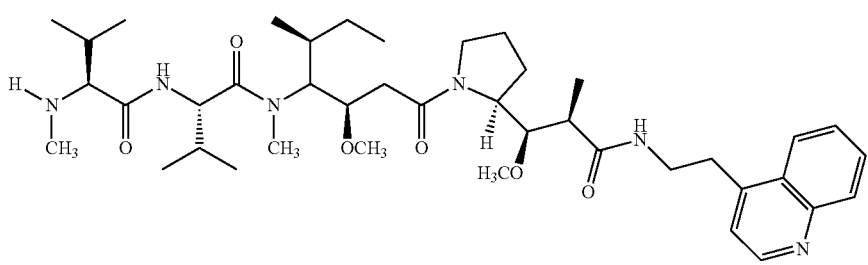
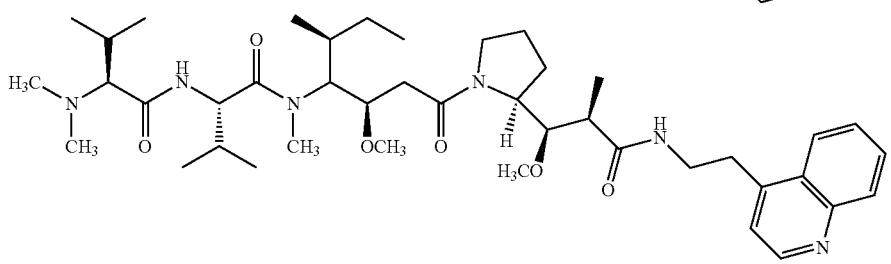
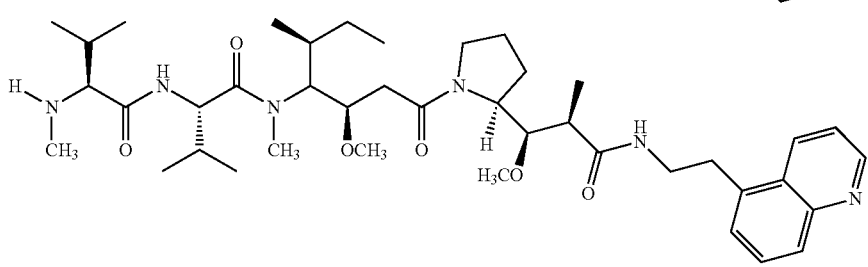

-continued
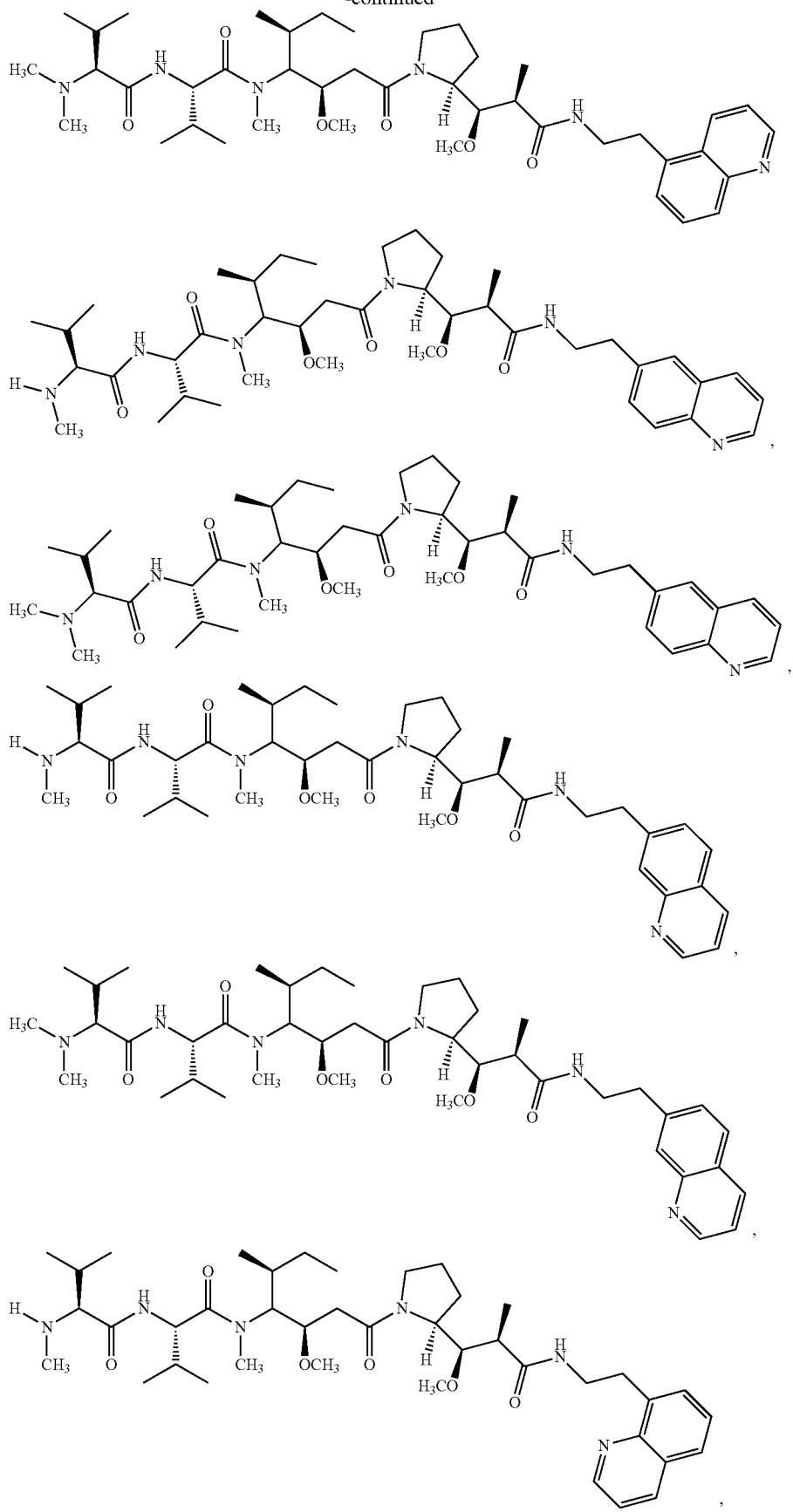

-continued
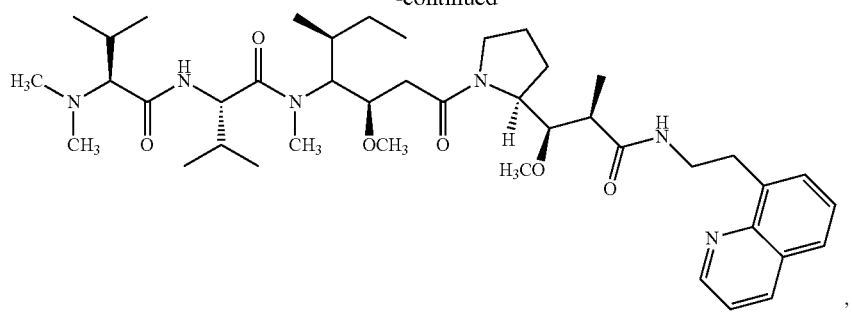
,
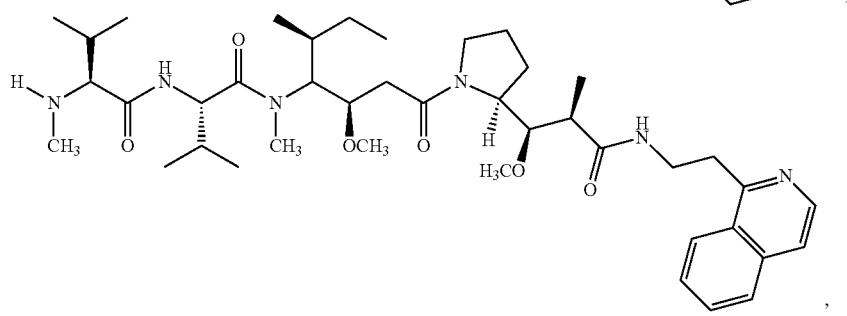
,
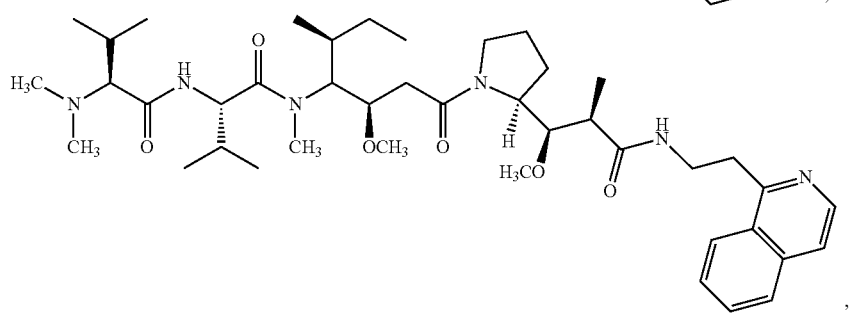
,
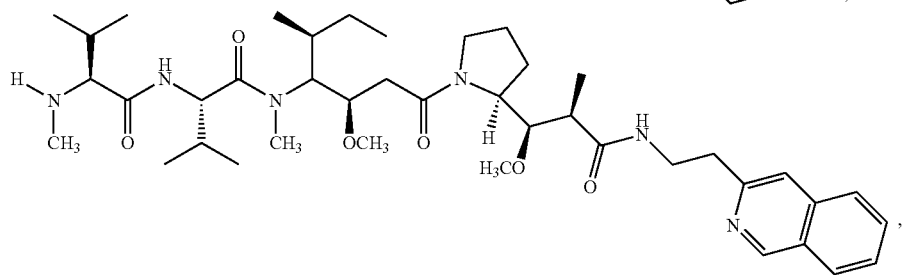
,
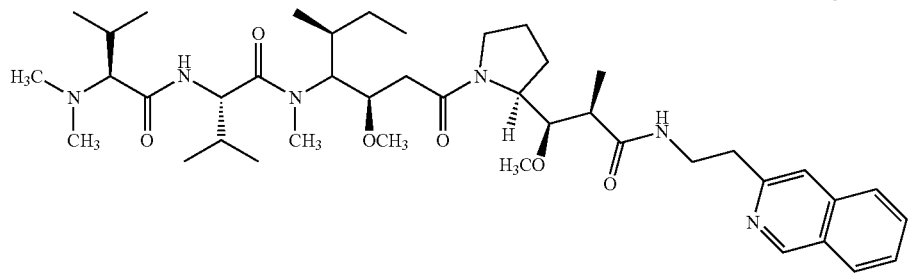
,
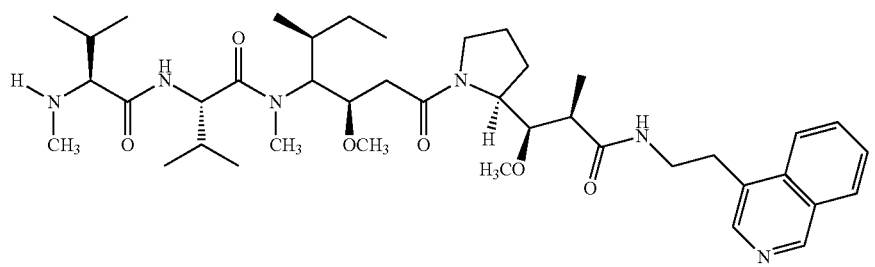

-continued
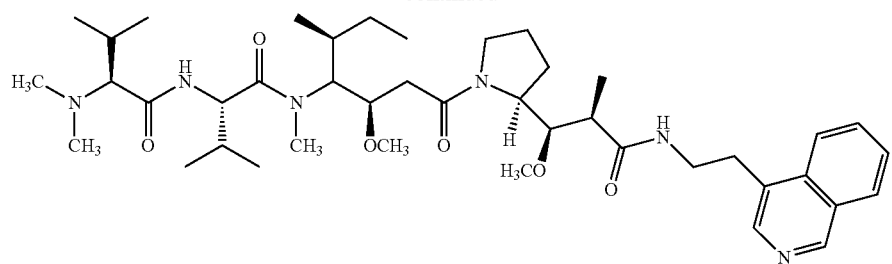
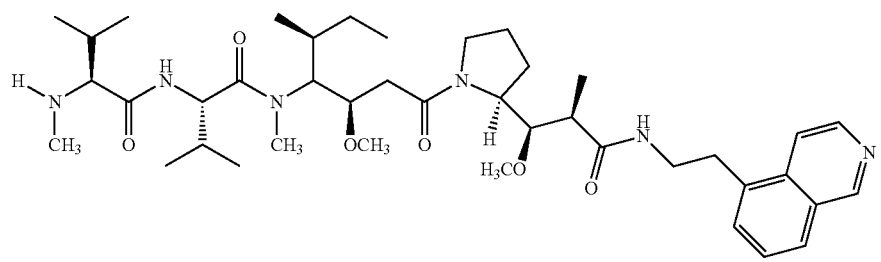
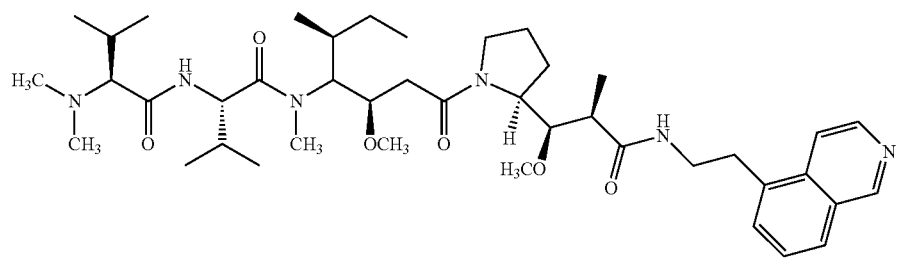
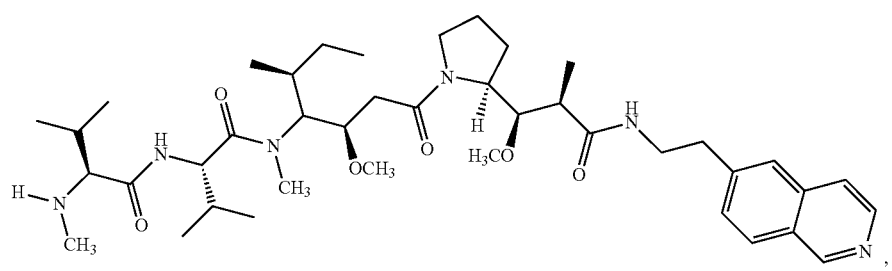
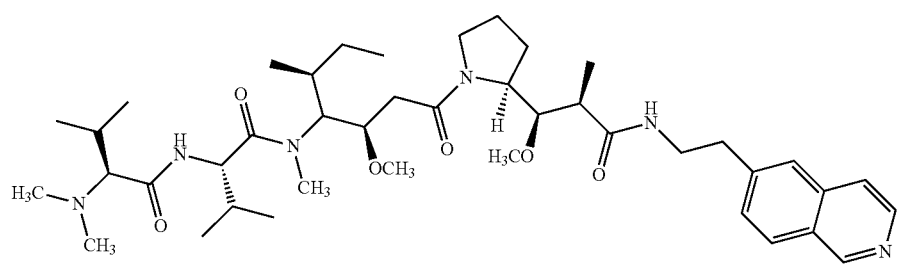
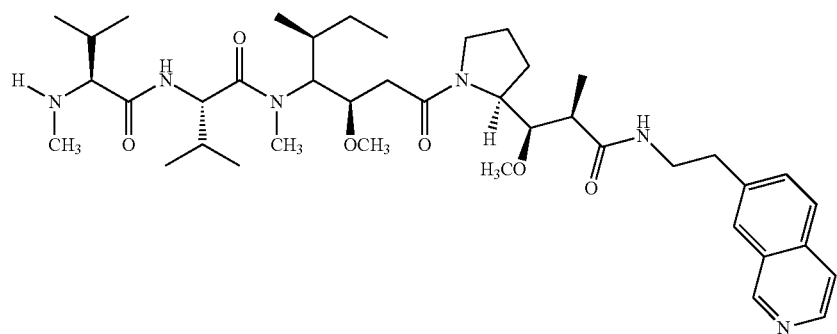

-continued
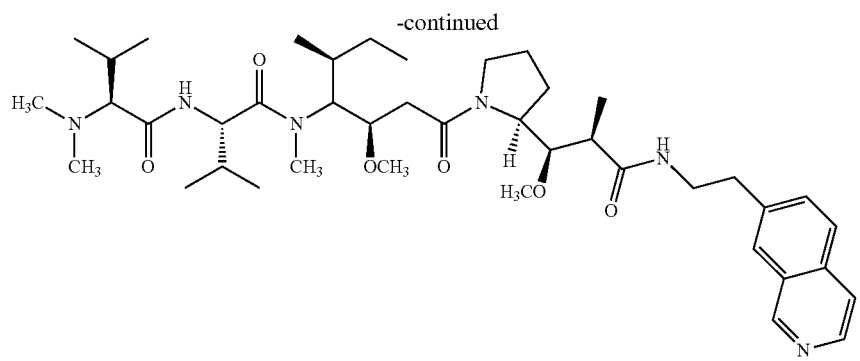
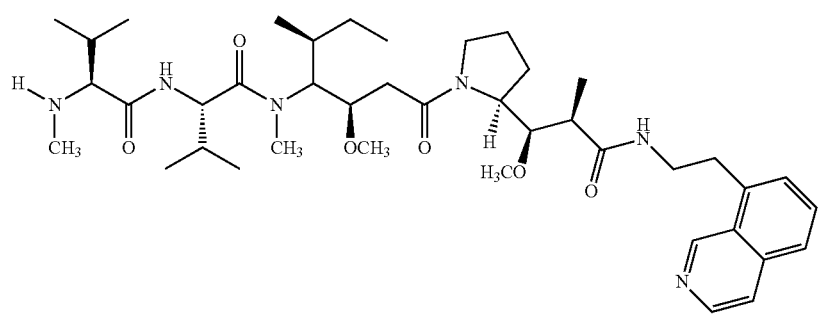
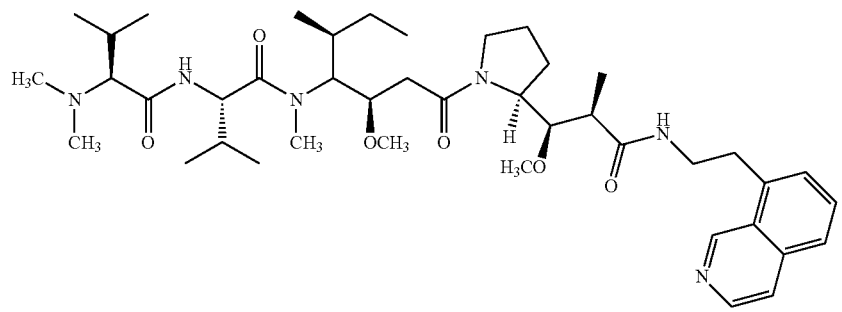
and
pharmaceutically acceptable salts thereof.
(132.) A compound, which is
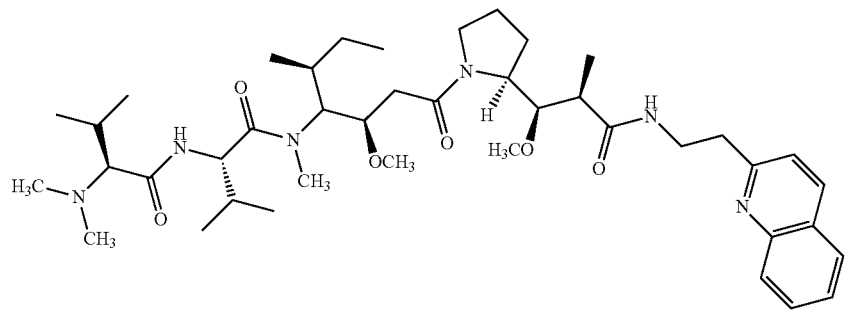 [SMILES: CC[C@H](C)C([C@@H](CC(=O)N1CCC[C@H]1[C@H](OC)[C@@H](C)C(=O)NCCc1ccc2ccccc2n1)OC)N(C)C(=O)[C@@H](NC(=O)[C@H](C(C)C)N(C)C)C(C)C]
and a pharmaceutically acceptable salt thereof.

(133.) A compound, which is
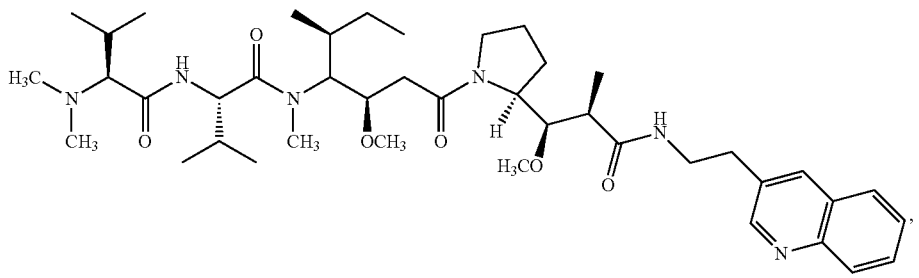 [SMILES: CC[C@H](C)C([C@@H](CC(=O)N1CCC[C@H]1[C@H](OC)[C@@H](C)C(=O)NCCc1cnc2ccccc2c1)OC)N(C)C(=O)[C@@H](NC(=O)[C@H](C(C)C)N(C)C)C(C)C]
and a pharmaceutically acceptable salt thereof.
(134.) A compound, which is
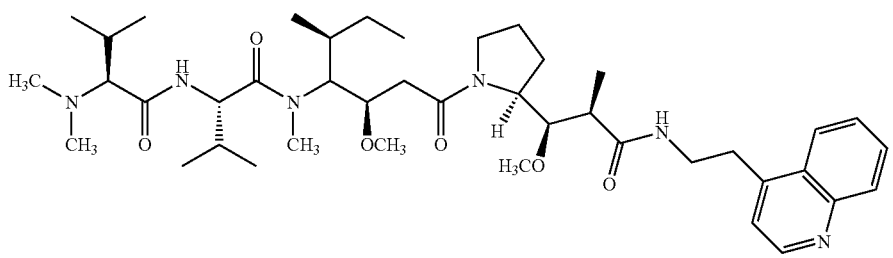 [SMILES: CC[C@H](C)C([C@@H](CC(=O)N1CCC[C@H]1[C@H](OC)[C@@H](C)C(=O)NCCc1ccnc2ccccc12)OC)N(C)C(=O)[C@@H](NC(=O)[C@H](C(C)C)N(C)C)C(C)C]
and a pharmaceutically acceptable salt thereof.
(135.) A compound, which is
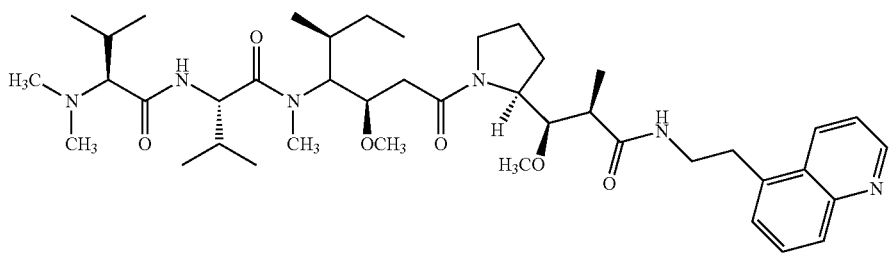 [SMILES: CC[C@H](C)C([C@@H](CC(=O)N1CCC[C@H]1[C@H](OC)[C@@H](C)C(=O)NCCc1cccc2ncccc12)OC)N(C)C(=O)[C@@H](NC(=O)[C@H](C(C)C)N(C)C)C(C)C]
and a pharmaceutically acceptable salt thereof.
(136.) A compound, which is
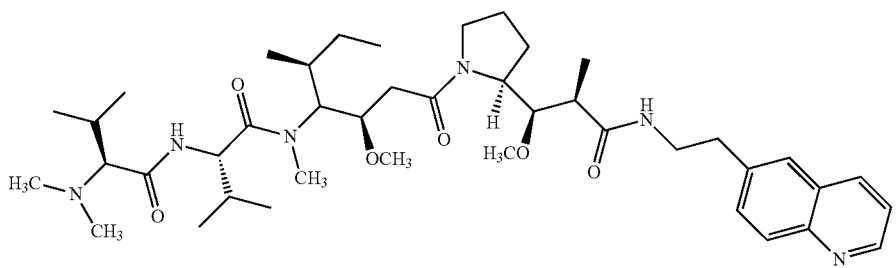 [SMILES: CC[C@H](C)C([C@@H](CC(=O)N1CCC[C@H]1[C@H](OC)[C@@H](C)C(=O)NCCc1ccc2ncccc2c1)OC)N(C)C(=O)[C@@H](NC(=O)[C@H](C(C)C)N(C)C)C(C)C]
and a pharmaceutically acceptable salt thereof.

(137.) A compound, which is

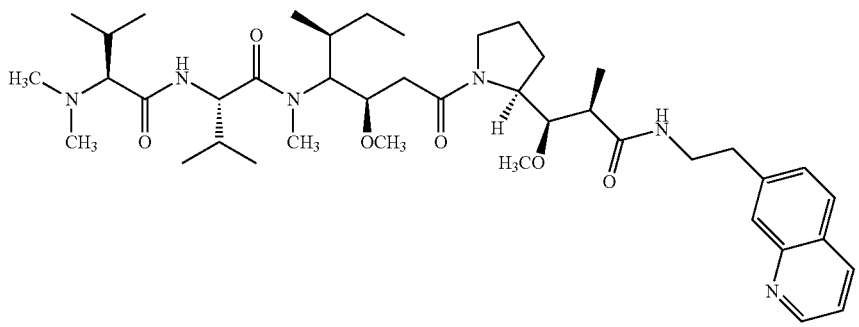 [SMILES: CC[C@H](C)C([C@@H](CC(=O)N1CCC[C@H]1[C@H](OC)[C@@H](C)C(=O)NCCc1ccc2cccnc2c1)OC)N(C)C(=O)[C@@H](NC(=O)[C@H](C(C)C)N(C)C)C(C)C]

and a pharmaceutically acceptable salt thereof.

(138.) A compound, which is

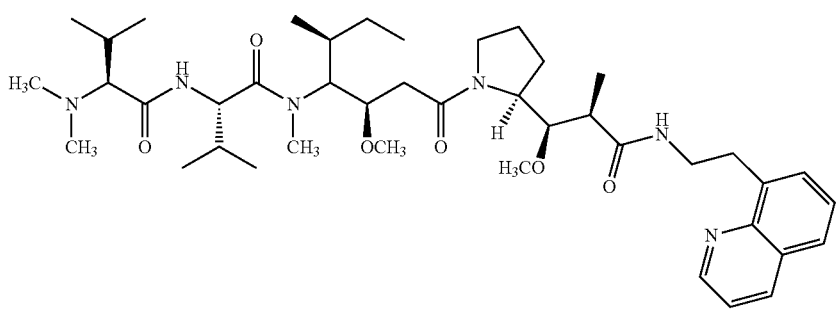 [SMILES: CC[C@H](C)C([C@@H](CC(=O)N1CCC[C@H]1[C@H](OC)[C@@H](C)C(=O)NCCc1cccc2cccnc12)OC)N(C)C(=O)[C@@H](NC(=O)[C@H](C(C)C)N(C)C)C(C)C]

and a pharmaceutically acceptable salt thereof.

(139.) A pharmaceutical composition comprising a combination of compounds of the above (1.) to (138.) or pharmaceutically acceptable salts thereof and a pharmaceutically acceptable carrier.

(140.) The pharmaceutical composition of the above (139.) or the above (140.), further comprising a therapeutically effective amount of a second therapeutic agent selected from the group consisting of a tubulin-forming inhibitor, a topoisomerase inhibitor, and a DNA binder.

(141.) A method for killing or inhibiting the proliferation of tumor cells or cancer cells comprising treating the tumor cells or cancer cells with a compound of any of the above (1.) to (138.), or a pharmaceutical composition of any one of the above (139.) to (141.), in an amount effective to kill or inhibit the proliferation of the tumor cells or cancer cells.

(142.) A method for treating cancer in a patient in need thereof comprising administering to the patient a compound of any of the above (1.) to (138.), or a pharmaceutical composition of any one of the above (139.) to (141.), wherein the compound or pharmaceutical composition is administered in an amount effective to treat cancer.

(143.) The method of the above (143.), further comprising administering an effective amount of a second therapeutic agent.

(144.) The method of the above (143.), wherein the cancer is selected from the group consisting of breast cancer, ovarian cancer, stomach cancer, endometrial cancer, salivary gland cancer, lung cancer, kidney cancer, colon cancer, colorectal cancer, thyroid cancer, pancreatic cancer, prostate cancer, bladder cancer and central nervous system cancer.

(145.) The method of the above (143.), wherein the cancer is selected from the group consisting of breast cancer, lung cancer, colon cancer, pancreatic cancer, prostate cancer and central nervous system cancer.

(146.) A method of determining inhibition of cellular proliferation by a compound, comprising contacting cells in a cell culture medium with the compound of any of the above (1.) to (138.) and measuring the cytotoxic activity of the compound, whereby proliferation of the cells is inhibited.

(147.) A method of inhibiting the growth of tumor cells that overexpress a tumor-associated antigen comprising administering to a patient the compound of any of the above (1.) to (138.) conjugated to an antibody that is specific for said tumor-associated antigen, and optionally a second therapeutic agent wherein the compound and the second therapeutic agent are each administered in amounts effective to inhibit the growth of tumor cells in the patient.

(148.) The method of the above (148.), wherein the compound sensitizes the tumor cells to said second therapeutic agent.

(149.) The method of the above (148.), wherein the compound induces cell death.

(150.) The method of the above (148.), wherein the compound induces apoptosis.

(151.) A use of the compound of any of the above (1.) to (138.) in the manufacture of a medicament for treating cancer.

(152.) An article of manufacture comprising the compound of any of the above (1.) to (138.), a container, and a package insert or label indicating that the compound can be used to treat cancer characterized by the overexpression of at least one tumor-associated antigen.

DEFINITIONS

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The phrase "pharmaceutically acceptable salt," as used herein, refers to pharmaceutically acceptable organic or inorganic salts of a compound of the disclosure. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The term "pharmaceutically acceptable carrier" refers to a diluent, adjuvant or excipient, with which a compound of the disclosure may be administered. Pharmaceutically acceptable carriers include any and all solvents, diluents, or other liquid vehicles, dispersions or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the disclosure such as by producing any undesirable biological effect or otherwise interacting in a deleterious manner with any other component(s) of the pharmaceutically acceptable composition, its use is contemplated to be within the scope of this disclosure. Examples of pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols, such a propylene glycol or polyethylene glycol; esters, such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "therapeutically effective amount" refers to an amount of a compound of the disclosure or a pharmaceutically acceptable salt thereof effective to treat a cancer in a patient. For purposes of this disclosure, the therapeutically effective amount of the compound may reduce the number of cancer cells; reduce the tumor size; reduce to some extent cancer cell infiltration into peripheral organs, tumor metastasis or tumor growth; and/or relieve to some extent one or more of the symptoms associated with the cancer.

The terms "treat" or "treatment" refer to therapeutic treatment and prophylactic measures to obtain a beneficial or desired result. For purposes of this disclosure, beneficial or desired results include, but are not limited to, alleviation of symptoms, diminishment of extent of disease, stabilized (i.e., not worsening) state of disease, delay or slowing of disease progression, amelioration or palliation of the disease state, remission (whether partial or total), whether detectable or undetectable and prevention of relapse. "Treatment" can also include prolonging survival as compared to expected survival if not receiving treatment. Those in need of treatment include those already having the condition or disorder as well as those prone to have the condition or disorder.

The terms "cancer" and "cancerous" refer to or describe the physiological condition or disorder in mammals that is typically characterized by unregulated cell growth. A "tumor" comprises one or more cancerous cells.

Exemplary cancers include, but not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, central nervous system cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute non-lymphocytic leukemia, acute undifferentiated leukemia, chronic myelocytic leukemia (CML), chronic lymphocytic leukemia (CLL), hairy cell leukemia, multiple myeloma, Hodgkin's disease, non-Hodgkin's lymphoma, Waldenstrom's macroglobulinemia, heavy chain disease and polycythemia vera.

The term "cytotoxic activity" refers to a cell-killing, a cytostatic or an anti-proliferative effect of a compound of the disclosure. Methods for measuring cytotoxic activity are well-known in the art.

Cytotoxic activity may be expressed as the $IC_{50}$ value, which is the concentration (molar or mass) per unit volume at which half the cells survive.

The term "patient," as used herein, includes, but is not limited to, a human, rat, mouse, guinea pig, monkey, pig, goat, cow, horse, dog, cat, bird and fowl. In some embodiments, the patient is a human.

The term "$(C_1-C_6)$ alkyl" refers to saturated linear or branched hydrocarbon structures having 1, 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of "$(C_1-C_6)$ alkyl groups include methyl, ethyl, n-propyl, iso-propyl, n-butyl, tert-butyl, n-pentyl, n-hexyl, and the like.

The term "$(C_1-C_3)$ alkyl" refers to saturated linear or branched hydrocarbon structures having 1, 2 or 3 carbon atoms. When an alkyl residue having a specific number of carbons is named, all geometric isomers having that number of carbons are intended to be encompassed; thus, for example, "propyl" includes n-propyl and iso-propyl. Examples of "$(C_1-C_3)$ alkyl groups include methyl, ethyl, n-propyl and iso-propyl.

The term "$(C_2-C_6)$ alkenyl" refers to a straight-chain or branched unsaturated hydrocarbon radical having 2, 3, 4, 5 or 6 carbon atoms and a double bond in any position, e.g., ethenyl, 1 propenyl, 2 propenyl (allyl), 1-butenyl, 2-butenyl, 3-butenyl, 1-methylethenyl, 1-methyl-1 propenyl, 2 methyl-2-propenyl, 2-methyl-1-propenyl, 1-methyl-2-propenyl, 1-hexenyl, 2-hexenyl, 3-hexenyl, 2-methyl-2-pentenyl, 4-methyl-2-pentenyl, 4-methyl-1-pentenyl, 3-methyl-1-pentenyl, and the like.

The term "$(C_2-C_6)$alkynyl" refers to a straight chain or branched hydrocarbon having 2, 3, 4, 5 or 6 carbon atoms and including at least one carbon-carbon triple bond. Examples of alkynyl include ethynyl, propynyl, 1-butynyl, 2-butynyl, 1-pentynyl, 2-pentynyl, 1-hexynyl, 2-hexynyl, 3-hexynyl, 4-methyl-2-pentynyl and the like.

The term "Protecting Group" refers to any group that is capable of reversibly protecting another functional group from undergoing an undesired reaction. Suitable oxygen and nitrogen protecting groups, as well as suitable conditions for protection and deprotection are well-known in the art and are described e.g., in T. W. Greene and P. G. M. Wuts, "Protective Groups in Organic Synthesis", Third edition, Wiley, New York 1999, and references cited therein. Representative hydroxy protecting groups include acetates (e.g., pivaloate and benzoate), benzyl ether, p-methoxybenzyl ether, trityl ether, tetrahydropyranyl ether, trialkylsilyl ethers (e.g., trimethylsilyl ether, triethylsilyl ether, triisopropyl silyl ether, t-butyldimethyl silyl ether, triphenylmethyl silyl ether), allyl ethers, methoxymethyl ether, 2-methoxyethoxymethyl ether, methanesulfonate and p-toluenesulfonate. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

The term "antibody" as used herein includes whole antibodies, monoclonal antibodies, polyclonal antibodies, monospecific antibodies, multispecific antibodies (e.g., bispecific antibodies), and antibody fragments that exhibit the desired biological activity. An antibody may be of any type or class (e.g., IgG, IgE, IgM, IgD, and IgA) or subclass (e.g., IgG1, IgG2, IgG3, IgG4, IgA1 and IgA2). The antibody may be derived from any suitable species. In some embodiments, the antibody is of human or murine origin.

An antibody may be, for example, human, humanized or chimeric.

The term "monoclonal antibodies" as used herein refers to antibodies produced by a single clone of cells or cell line and comprising identical antibody molecules. The term "polyclonal antibodies" refers to antibodies produced by more than one type of cell or cell line and comprising different antibody molecules.

A compound of the disclosure can contain one, two, or more asymmetric centers and thus can give rise to enantiomers, diastereomers, and other stereoisomeric forms. The disclosure encompasses compounds with all such possible forms, as well as their racemic and resolved forms or any mixture thereof, unless specifically otherwise indicated. When a compound of the disclosure contains an olefinic double bond, a C=N double bond, or any other center of geometric asymmetry, it is intended to include all "geometric isomers", e.g., both Z and E geometric isomers, unless specifically otherwise indicated. All "tautomers", e.g., amine-imine, enamine-enimine, enamine-imine, urea-isourea, ketone-enol, amide-imidic acid, lactam-lactim, are intended to be encompassed by the disclosure as well unless specifically otherwise indicated.

Compounds of Formula (I)

In one embodiment, the present disclosure provides a compound of formula (I),

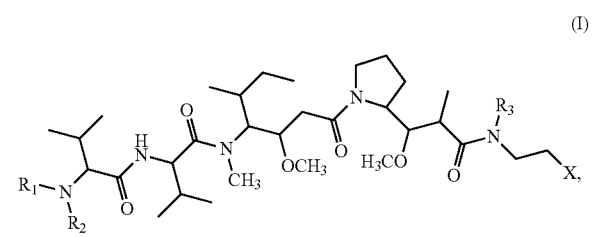

(I)

or a pharmaceutically acceptable salt thereof, wherein $R_1$ is selected from H, $(C_1-C_6)$ alkyl, $(C_2-C_6)$ alkenyl, $(C_2-C_6)$ alkynyl, a Protecting Group or a Linker Unit;

$R_2$ is selected from H, $(C_1-C_6)$ alkyl, $(C_2-C_6)$ alkenyl or $(C_2-C_6)$ alkynyl;

$R_3$ is H or $(C_1-C_6)$ alkyl; and

X is a bicyclic heterocyclic ring system selected from quinolinyl, isoquinolinyl, 1,5-naphthyridinyl, quinoxalinyl, quinazolinyl, cinnolinyl, 2,7-naphthyridinyl, 1,8-naphthyridinyl, 2,6-naphthyridinyl, phthalazinyl, 2H-chromenyl, 1H-1,5-benzodiazepinyl, 1,2,3-benzotriazinyl and 2,5-benzodiazocinyl, wherein the bicyclic heterocyclic ring system is unsubstituted or substituted with 1, 2 or 3 substituent(s) selected from $(C_1-C_6)$ alkoxy, methylene dioxy, hydroxyl, O-Protecting Group and O-Linker Unit.

In one embodiment, $R_1$ is H, $(C_1-C_6)$ alkyl or a Linker Unit. In another embodiment, $R_1$ is H or $(C_1-C_6)$ alkyl. In another embodiment, $R_1$ is H or a Linker Unit. In another embodiment, $R_1$ is $(C_1-C_6)$ alkyl or a Linker Unit. In another embodiment, $R_1$ is H, methyl or a Linker Unit. In another embodiment, $R_1$ is H or methyl. In another embodiment, $R_1$ is H or a Linker Unit. In another embodiment, $R_1$ is methyl or a Linker Unit. In another embodiment, $R_1$ is H. In another embodiment, $R_1$ is methyl. In another embodiment, $R_1$ is a Linker Unit.

In one embodiment, $R_2$ is H or $(C_1-C_6)$ alkyl. In another embodiment, $R_2$ is H or methyl. In another embodiment, $R_2$ is H. In another embodiment, $R_2$ is $(C_1-C_6)$ alkyl. In another embodiment, $R_2$ is methyl.

In one embodiment, $R_3$ is H or $(C_1-C_6)$ alkyl. In another embodiment, $R_3$ is H or methyl. In another embodiment, $R_3$ is H. In another embodiment, $R_3$ is $(C_1-C_3)$ alkyl. In another embodiment, $R_3$ is methyl.

In one embodiment, X is quinolinyl or isoquinolinyl. In another embodiment, X is quinolinyl. In another embodiment, X is isoquinolinyl. In another embodiment, X is 1,5-naphthyridinyl. In another embodiment, X is quinoxalinyl. In another embodiment, X is quinazolinyl. In another embodiment, X is cinnolinyl. In another embodiment, X is 2,7-naphthyridinyl. In another embodiment, X is 1,8-naphthyridinyl. In another embodiment, X is 2,6-naphthyridinyl. In another embodiment, X is phthalazinyl. In another embodiment, X is 2H-chromenyl. In another embodiment, X is 1H-1,5-benzodiazepinyl. In another embodiment, X is 1,2,3-benzotriazinyl. In another embodiment, X is 2,5-benzodiazocinyl. In each embodiment, X can be attached to the rest of the molecule at any available position on the bicyclic heterocyclic ring system.

In one embodiment, X is 2-quinolinyl, 3-quinolinyl, 4-quinolinyl, 5-quinolinyl, 6-quinolinyl, 7-quinolinyl or 8-quinolinyl. In another embodiment, X is 2-quinolinyl, 3-quinolinyl, 6-quinolinyl, 7-quinolinyl or 8-quinolinyl. In another embodiment, X is 2-quinolinyl, 3-quinolinyl, 6-quinolinyl, 7-quinolinyl or 8-quinolinyl. In another embodiment, X is 2-quinolinyl, 6-quinolinyl, 7-quinolinyl or 8-quinolinyl. In another embodiment, X is 2-quinolinyl. In another embodiment, X is 3-quinolinyl. In another embodiment, X is 4-quinolinyl. In another embodiment, X is 5-quinolinyl. In another embodiment, X is 6-quinolinyl. In another embodiment, X is 7-quinolinyl. In another embodiment, X is 8-quinolinyl.

In one embodiment, X is 1-isoquinolinyl, 3-isoquinolinyl, 4-isoquinolinyl, 5-isoquinolinyl, 6-isoquinolinyl, 7-isoquinolinyl or 8-isoquinolinyl. In another embodiment, X is 1-isoquinolinyl, 3-isoquinolinyl, 6-isoquinolinyl, 7-isoquinolinyl or 8-isoquinolinyl. In another embodiment, X is 1-isoquinolinyl, 3-isoquinolinyl, 6-isoquinolinyl, 7-isoquinolinyl or 8-isoquinolinyl. In another embodiment, X is 1-isoquinolinyl, 6-isoquinolinyl, 7-isoquinolinyl or 8-isoquinolinyl. In another embodiment, X is 1-isoquinolinyl. In another embodiment, X is 3-isoquinolinyl. In another embodiment, X is 4-isoquinolinyl. In another embodiment, X is 5-isoquinolinyl. In another embodiment, X is 6-isoquinolinyl. In another embodiment, X is 7-isoquinolinyl. In another embodiment, X is 8-isoquinolinyl.

In one embodiment, $R_1$ is H, $(C_1-C_6)$ alkyl or a Linker Unit and $R_2$ is H or $(C_1-C_6)$ alkyl. In another embodiment, $R_1$ is H or $(C_1-C_6)$ alkyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is $(C_1-C_6)$ alkyl or a Linker Unit and $R_2$ is H or $(C_1-C_6)$ alkyl. In another embodiment, $R_1$ is H, methyl or a Linker Unit and $R_2$ is H or $(C_1-C_6)$ alkyl. In another embodiment, $R_1$ is H or methyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is methyl or a Linker Unit and $R_2$ is H or $(C_1-C_6)$ alkyl. In another embodiment, $R_1$ is H and $R_2$ is H or $(C_1-C_6)$ alkyl. In another embodiment, $R_1$ is methyl and $R_2$ is H or $(C_1-C_6)$ alkyl. In another embodiment, $R_1$ is a Linker Unit and $R_2$ is H or $(C_1-C_6)$ alkyl.

In one embodiment, $R_1$ is H, $(C_1-C_6)$ alkyl or a Linker Unit and $R_2$ is H or methyl. In another embodiment, $R_1$ is H, $(C_1-C_6)$ alkyl or a Linker Unit and $R_2$ is H. In another embodiment, $R_1$ is H, $(C_1-C_6)$ alkyl or a Linker Unit and $R_2$ is $(C_1-C_6)$ alkyl. In another embodiment, $R_1$ is H, $(C_1-C_6)$ alkyl or a Linker Unit and $R_2$ is methyl.

In one embodiment, $R_1$ is methyl and $R_2$ is methyl. In another embodiment, $R_1$ is H and $R_2$ is methyl. In another embodiment, $R_1$ is H and $R_2$ is H. In another embodiment, $R_1$ is a Linker Unit and $R_2$ is methyl. In another embodiment, $R_1$ is a Linker Unit and $R_2$ is H.

In one embodiment, $R_1$ is H, $(C_1-C_6)$ alkyl or a Linker Unit and $R_3$ is H or $(C_1-C_3)$ alkyl. In another embodiment, $R_1$ is H or $(C_1-C_6)$ alkyl and $R_3$ is H or $(C_1-C_3)$ alkyl. In another embodiment, $R_1$ is H or a Linker Unit and $R_3$ is H or $(C_1-C_3)$ alkyl. In another embodiment, $R_1$ is $(C_1-C_6)$ alkyl or a Linker Unit and $R_3$ is H or $(C_1-C_3)$ alkyl. In another embodiment, $R_1$ is H, methyl or a Linker Unit and $R_3$ is H or $(C_1-C_3)$ alkyl. In another embodiment, $R_1$ is H or methyl and $R_3$ is H or $(C_1-C_3)$ alkyl. In another embodiment, $R_1$ is H or a Linker Unit and $R_3$ is H or $(C_1-C_3)$ alkyl. In another embodiment, $R_1$ is methyl or a Linker Unit and $R_3$ is H or $(C_1-C_3)$ alkyl. In another embodiment, $R_1$ is H and $R_3$ is H or $(C_1-C_3)$ alkyl. In another embodiment, $R_1$ is methyl and $R_3$ is H or $(C_1-C_3)$ alkyl. In another embodiment, $R_1$ is a Linker Unit and $R_3$ is H or $(C_1-C_3)$ alkyl.

In one embodiment, $R_1$ is H, $(C_1-C_6)$ alkyl or a Linker Unit and $R_3$ is H or methyl. In another embodiment, $R_1$ is H, $(C_1-C_6)$ alkyl or a Linker Unit and $R_3$ is H. In another embodiment, $R_1$ is H, $(C_1-C_6)$ alkyl or a Linker Unit and $R_3$ is $(C_1-C_3)$ alkyl. In another embodiment, $R_1$ is H, $(C_1-C_6)$ alkyl or a Linker Unit and $R_3$ is methyl.

In one embodiment, $R_1$ is methyl and $R_3$ is methyl. In another embodiment, $R_1$ is H and $R_3$ is methyl. In another embodiment, $R_1$ is H and $R_3$ is H. In another embodiment, $R_1$ is a Linker Unit and $R_3$ is methyl. In another embodiment, $R_1$ is a Linker Unit and $R_3$ is H.

In one embodiment, $R_2$ is H or $(C_1-C_6)$ alkyl and $R_3$ is H or $(C_1-C_3)$ alkyl. In another embodiment, $R_2$ is H and $R_3$ is H or $(C_1-C_3)$ alkyl. In another embodiment, $R_2$ is $(C_1-C_6)$ alkyl and $R_3$ is H or $(C_1-C_3)$ alkyl. In another embodiment, $R_2$ is H or methyl and $R_3$ is H or $(C_1-C_3)$ alkyl. In another embodiment, $R_2$ is methyl and $R_3$ is H or $(C_1-C_3)$ alkyl.

In one embodiment, $R_2$ is H or $(C_1-C_6)$ alkyl and $R_3$ is H. In another embodiment, $R_2$ is H or $(C_1-C_6)$ alkyl and $R_3$ is methyl. In another embodiment, $R_2$ is H and $R_3$ is H. In another embodiment, $R_2$ is $(C_1-C_6)$ alkyl and $R_3$ is H. In another embodiment, $R_2$ is methyl and $R_3$ is H. In another embodiment, $R_2$ is H and $R_3$ is $(C_1-C_3)$ alkyl. In another embodiment, $R_2$ is H and $R_3$ is methyl. In another embodiment, $R_2$ is $(C_1-C_6)$ alkyl and $R_3$ is $(C_1-C_3)$ alkyl. In another embodiment, $R_2$ is ($C_1$-$C_6$) alkyl and $R_3$ is methyl. In another embodiment, $R_2$ is methyl and $R_3$ is methyl.

In one embodiment, the compound of formula (I) may be conjugated to an antibody. The antibody may be conjugated to the compound of the formula (I) through the N-terminus or the C-terminus. In one embodiment, the antibody is conjugated to the antibody at the N-terminus. In another embodiment, the antibody is conjugated to the antibody at the C-terminus. In one embodiment, the compound of formula (I) is conjugated directly to an antibody. In another embodiment, the compound of formula (I) is conjugated to an antibody through a Linker Unit. The Linker Unit can operate to provide a suitable release of the compound of formula (I). The preparation of antibody drug conjugates is known to those of skill in the art.

In embodiments in which the compound of formula (I) is conjugated to an antibody through a Linker Unit, the Linker Unit may comprise a cleavable linker in one embodiment and a non-cleavable linker in another embodiment.

In embodiments in which $R_1$ comprises a cleavable linker, the cleavable linker may be cleaved by methods known in the art. In one embodiment, the cleavable linker may be cleaved by a method selected from the group consisting of glycosidase-induced cleavage, acid-induced cleavage, light-induced cleavage, peptidase-induced cleavage, esterase-induced cleavage, and disulfide bond cleavage. In one embodiment, the cleavage method is selected from the group consisting of glycosidase-induced cleavage, acid-induced cleavage, peptidase-induced cleavage, esterase-induced cleavage, and disulfide bond cleavage. In another embodiment, the cleavage method is selected from the group consisting of glycosidase-induced cleavage, peptidase-induced cleavage, and esterase-induced cleavage. In another embodiment, the cleavage method is selected from glycosidase-induced cleavage or peptidase-induced cleavage. In another embodiment, the cleavage method is selected from glycosidase-induced cleavage or esterase-induced cleavage. In another embodiment, the cleavage method is selected from peptidase-induced cleavage or esterase-induced cleavage.

In embodiments in which $R_1$ comprises a cleavable linker, the cleavable linker may comprise a glycosidic bond, a hydrazone, a cathepsin-B-cleavable peptide, a disulfide or an ester bond. In one embodiment, the cleavable linker comprises a glycosidic bond, a hydrazone, a cathepsin-B-cleavable peptide, or an ester bond. In one embodiment, the cleavable linker comprises a glycosidic bond, a hydrazone, or a cathepsin-B-cleavable peptide. In one embodiment, the cleavable linker comprises a glycosidic bond, a hydrazone, or an ester bond. In one embodiment, the cleavable linker comprises a glycosidic bond, a cathepsin-B-cleavable peptide, or an ester bond. In one embodiment, the cleavable linker comprises a hydrazone, a cathepsin-B-cleavable peptide, or an ester bond.

In one embodiment, the cleavable linker comprises a glycosidic bond. In one embodiment, the cleavable linker comprises glucuronide.

The compounds of the disclosure may be conjugated to any antibody, e.g., an antibody that binds to a tumor associated antigen. In one embodiment, the antibody used in the antibody drug conjugate of the disclosure is a monoclonal antibody. The antibody can be a chimeric antibody, a humanized antibody or an antibody fragment. In another embodiment, the antibody used in the antibody drug conjugate of the disclosure binds at least one of CD19, CD20, CD30, CD33, CD70, BCMA, Glypican-3, Liv-1 and Lewis Y antigens.

In one embodiment, the Linker Unit is a bifunctional moiety that can be used to conjugate a compound of formula (I) to an antibody. Such bifunctional moieties are known in the art and include, but are not limited to, alkyldiyl, an aryldiyl, a heteroaryldiyl, moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide. See, e.g., U.S. Pat. Nos. 6,214,345 and 7,745,394, the contents of both of which are incorporated by reference in their entireties.

In one embodiment, the Linker Unit is as described in U.S. Pat. Nos. 6,214,345 and 7,745,394 and has formula:

$A_a W_w Y_y$, wherein A is a Stretcher Unit,
a is 0 or 1,
each —W— is independently an Amino Acid Unit,
w is an integer ranging from 0 to 12,
Y is a Spacer Unit, and
y is 0, 1 or 2.

The Stretcher Unit (-A-), when present, is capable of linking an antibody to the Amino Acid Unit (—W—). The antibody has a functional group that can form a bond with a functional group of a Stretcher. Useful functional groups that can be present on an antibody, either naturally or via chemical manipulation include, but are not limited to, sulfhydryl (—SH), amino, hydroxyl, carboxy, the anomeric hydroxyl group of a carbohydrate, and carboxyl. In one aspect, the antibody functional groups are sulfhydryl and amino. Sulfhydryl groups can be generated by reduction of an intramolecular disulfide bond of an antibody. Alternatively, sulfhydryl groups can be generated by reaction of an amino group of a lysine moiety of an antibody using 2-iminothiolane (Traut's reagent) or another sulfhydryl generating reagent.

The Amino Acid Unit (—W—), when present, links the Stretcher Unit to the Spacer Unit if the Spacer Unit is present, links the Stretcher Unit to the compound of formula (I) if the Spacer Unit is absent, and links the antibody to the compound of formula (I) if the Stretcher Unit and Spacer Unit are absent.

$W_w$— is a dipeptide, tripeptide, tetrapeptide, pentapeptide, hexapeptide, heptapeptide, octapeptide, nonapeptide, decapeptide, undecapeptide or dodecapeptide unit. The Amino Acid may be any amino acid. In some embodiments, the Amino Acid Unit comprises natural amino acids. In other embodiments, the Amino Acid Unit comprises non-natural amino acids.

The Spacer Unit (—Y—), when present, links an Amino Acid Unit to the compound of formula (I) when an Amino Acid Unit is present. Alternately, the Spacer Unit links the Stretcher Unit to the compound of formula (I) when the Amino Acid Unit is absent. The Spacer Unit also links the compound of formula (I) to the antibody when both the Amino Acid Unit and Stretcher Unit are absent.

Suitable Spacer Units include, but are not limited to a glycine-glycine unit; a glycine unit; p-aminobenzyl alcohol (PAB) unit or aromatic compounds that are electronically similar to the PAB group such as 2-aminoimidazol-5-methanol derivatives (Hay et al. (1999) Bioorg. Med. Chem. Lett. 9:2237) and ortho or para-aminobenzylacetals; spacers that undergo cyclization upon amide bond hydrolysis, such as substituted and unsubstituted 4-aminobutyric acid amides (Rodrigues et al., Chemistry Biology, 1995, 2, 223), appropriately substituted bicyclo[2.2.1] and bicyclo[2.2.2] ring systems (Storm, et al., J. Amer. Chem. Soc., 1972, 94, 5815)

and 2-aminophenylpropionic acid amides (Amsberry, et al., J. Org. Chem., 1990, 55, 5867); and a branched bis(hydroxymethyl)styrene (BHMS) unit.

Examples of Linker Units, Stretching Units and Amino Acid Units are described in U.S. Pat. Nos. 6,214,345 and 7,745,394.

In some embodiments, $A_a$ is maleimidocaproyl (mc).

In some embodiments, $W_w$ is Valine-Citrulline (ValCit).

In some embodiments, $Y_y$ is p-aminobenzyloxycarbonyl (PABC).

In some embodiments, $A_a$ is maleimidocaproyl, $W_w$ is Valine-Citrulline and $Y_y$ is p-aminobenzyloxycarbonyl (mcValCitPABC).

In some embodiments, the Linker Unit is selected from maleimidocaproyl; mcValCitPABC-, MalPegXC2-, AmPegXC2-, mcValCitPABCAmPegXC2-, MalPegXC2ValCitPABC-, 2BrAcPegXC2, my-, mb-me-, MalC6-, PFPCOPe2XC2ValCitPABC-, PFPCOPegXC2AmPegYC2-, PFPCOPegXC2AlaAlaAsnPABC-, PFPCOPegXC2-, PFPCOPegXC2AmPegYC2PABC-, mcGly-, AzCOC2Ph4AmCOPeg2C2-, AzCOC2Ph4AmPeg1C1-, and AcLysValCitPABC-, each of which is described in U.S. Pat. No. 9,249,186.

The term "MalPegXC2-" refers to

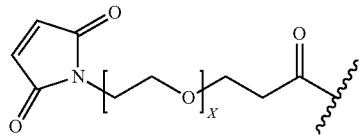

The term "AmPegXC2-" refers to

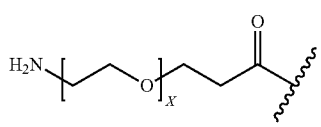

The term "mcValCitPABCAmPegXC2-" refers to

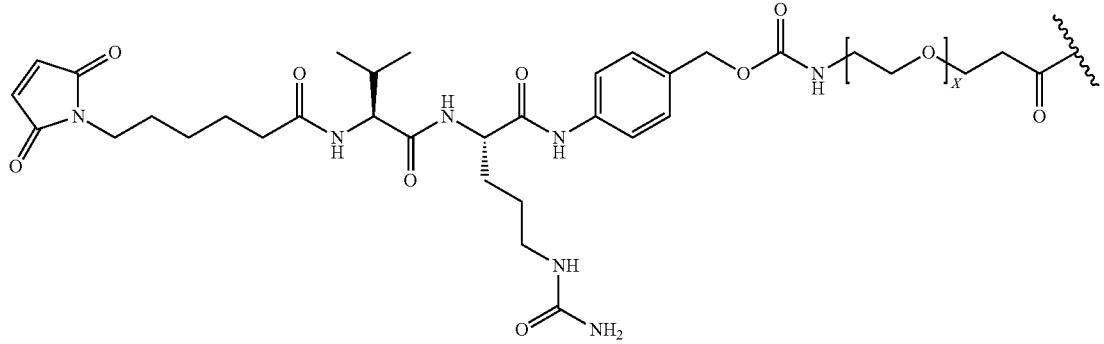

The term "MalPegXC2ValCitPABC-" refers to

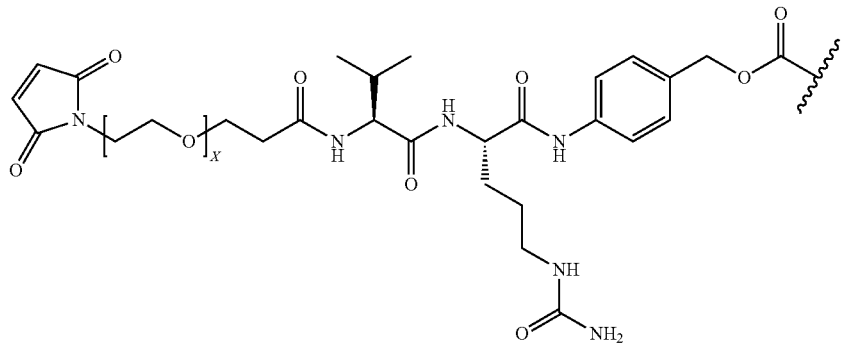

The term "2BrAcPegXC2" refers to

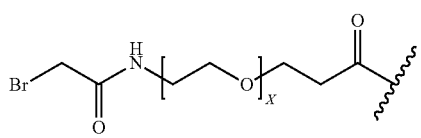

The term "mv-" refers to
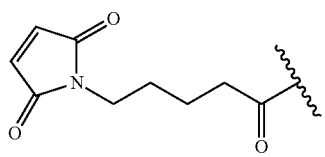
The term "mb" refers to
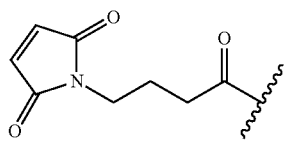
The term "me-" refers to
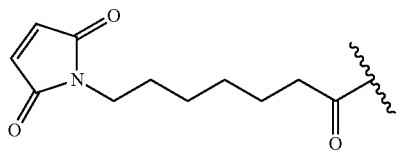
The term "MalC6-" refers to
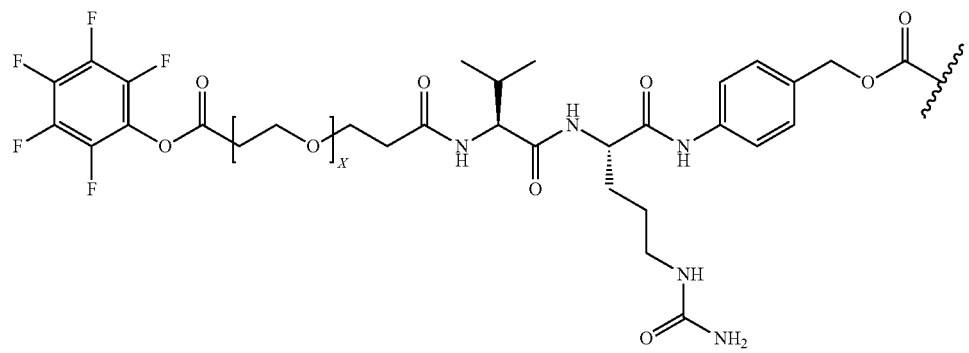
The term "PFPCOPe2XC2ValCitPABC-" refers to
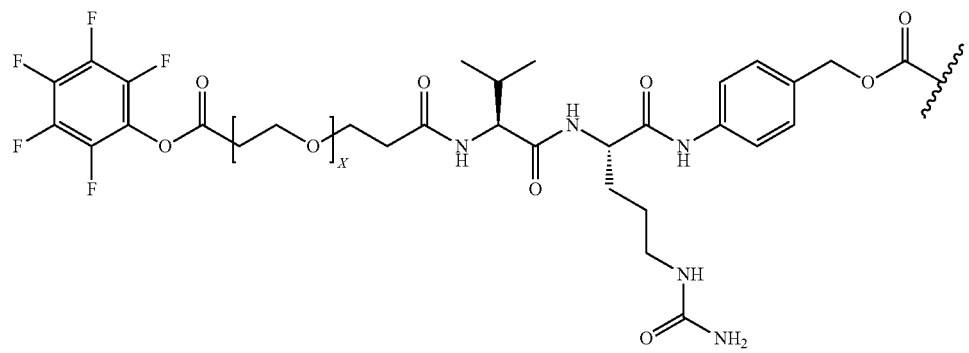
The term "PFPCOPegXC2AmPegYC2-" refers to
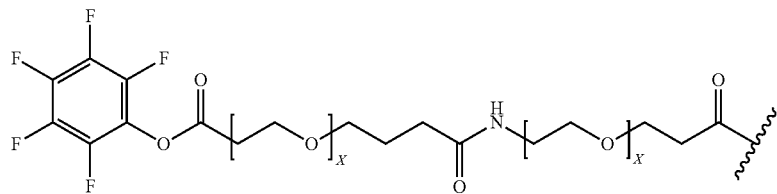
The term "PFPCOPegXC2AlaAlaAsnPABC-" refers to
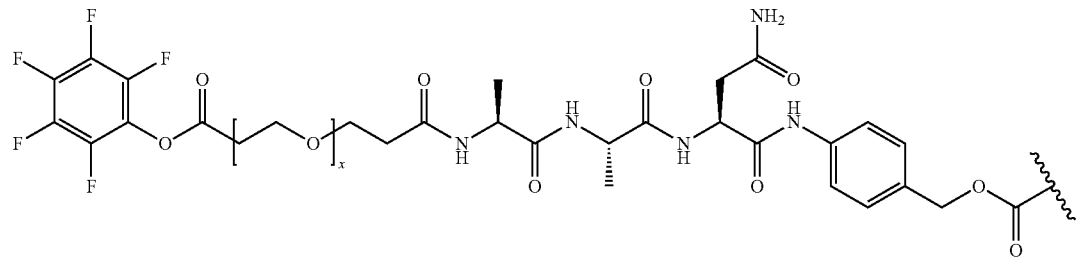

The term "PFPCOPegXC2-" refers to
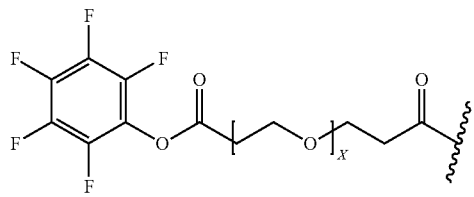
The term "PFPCOPegXC2AmPegYC2PABC-" refers to
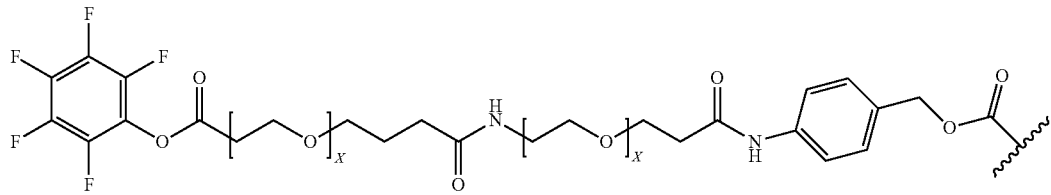
The term "mcGly-" refers to
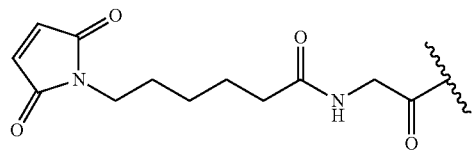
The term "AzCOC2Ph4AmCOPeg2C2-" refers to
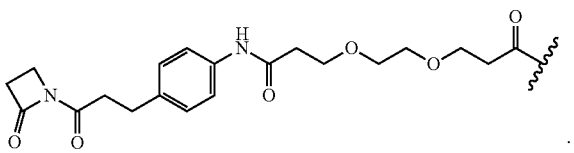 [SMILES: *C(=O)CCOCCOCCC(=O)Nc1ccc(CCC(=O)N2CCC2=O)cc1]
The term "AzCOC2Ph4AmPeglC1-" refers to
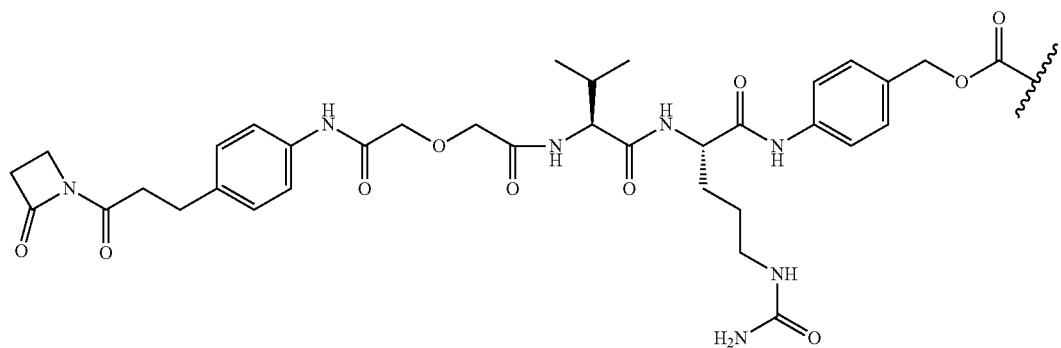
The term "AcLysValCitPABC-" refers to
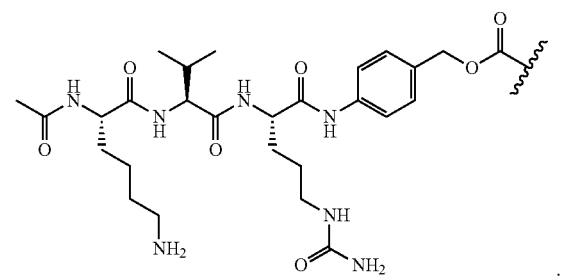 [SMILES: *C(=O)OCc1ccc(NC(=O)[C@H](CCCNC(N)=O)NC(=O)[C@@H](NC(=O)[C@H](CCCCN)NC(C)=O)C(C)C)cc1]

In another embodiment, the present disclosure provides a compound of formula (Ia),

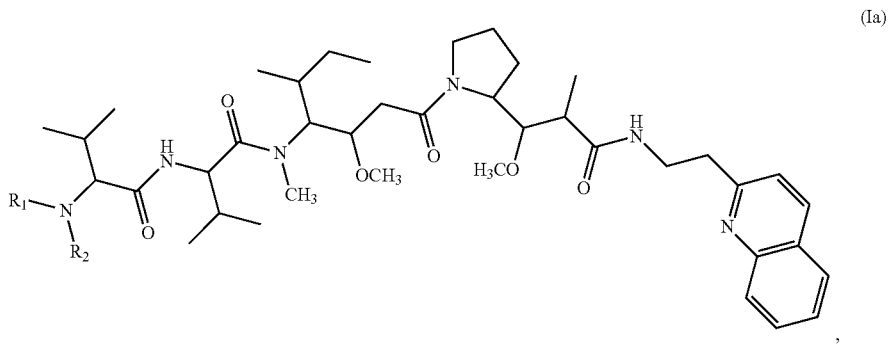

(Ia)

or a pharmaceutically acceptable salt thereof, wherein
$R_1$ is selected from H, $(C_1-C_6)$ alkyl, $(C_2-C_6)$ alkenyl, $(C_2-C_6)$ alkynyl, a Protecting Group or a Linker Unit; and
$R_2$ is selected from H, $(C_1-C_6)$ alkyl, $(C_2-C_6)$ alkenyl or $(C_2-C_6)$alkynyl.

In one embodiment, $R_1$ is H, $(C_1-C_6)$ alkyl or a Linker Unit. In another embodiment, $R_1$ is H or $(C_1-C_6)$ alkyl. In another embodiment, $R_1$ is H or a Linker Unit. In another embodiment, $R_1$ is $(C_1-C_6)$ alkyl or a Linker Unit. In another embodiment, $R_1$ is H, methyl or a Linker Unit. In another embodiment, $R_1$ is H or methyl. In another embodiment, $R_1$ is H or a Linker Unit. In another embodiment, $R_1$ is methyl or a Linker Unit. In another embodiment, $R_1$ is H. In another embodiment, $R_1$ is methyl. In another embodiment, $R_1$ is a Linker Unit.

In one embodiment, $R_2$ is H or $(C_1-C_6)$ alkyl. In another embodiment, $R_2$ is H or methyl. In another embodiment, $R_2$ is H. In another embodiment, $R_2$ is $(C_1-C_6)$ alkyl. In another embodiment, $R_2$ is methyl.

In one embodiment, $R_1$ is H, $(C_1-C_6)$ alkyl or a Linker Unit and $R_2$ is H or $(C_1-C_6)$ alkyl. In another embodiment, $R_1$ is H or $(C_1-C_6)$ alkyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is $(C_1-C_6)$ alkyl or a Linker Unit and $R_2$ is H or $(C_1-C_6)$ alkyl. In another embodiment, $R_1$ is H, methyl or a Linker Unit and $R_2$ is H or $(C_1-C_6)$ alkyl. In another embodiment, $R_1$ is H or methyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is methyl or a Linker Unit and $R_2$ is H or $(C_1-C_6)$ alkyl. In another embodiment, $R_1$ is H and $R_2$ is H or $(C_1-C_6)$ alkyl. In another embodiment, $R_1$ is methyl and $R_2$ is H or $(C_1-C_6)$ alkyl. In another embodiment, $R_1$ is a Linker Unit and $R_2$ is H or $(C_1-C_6)$ alkyl.

In one embodiment, $R_1$ is H, $(C_1-C_6)$ alkyl or a Linker Unit and $R_2$ is H or methyl. In another embodiment, $R_1$ is H, $(C_1-C_6)$ alkyl or a Linker Unit and $R_2$ is H. In another embodiment, $R_1$ is H, $(C_1-C_6)$ alkyl or a Linker Unit and $R_2$ is $(C_1-C_6)$ alkyl. In another embodiment, $R_1$ is H, $(C_1-C_6)$ alkyl or a Linker Unit and $R_2$ is methyl.

In one embodiment, $R_1$ is methyl and $R_2$ is methyl. In another embodiment, $R_1$ is H and $R_2$ is methyl. In another embodiment, $R_1$ is H and $R_2$ is H. In another embodiment, $R_1$ is a Linker Unit and $R_2$ is methyl. In another embodiment, $R_1$ is a Linker Unit and $R_2$ is H.

In one embodiment, the compound of formula (Ia) may be conjugated to an antibody, e.g., selected from the antibodies described above in connection with the compound of formula (I). The antibody may be conjugated to the compound of formula (Ia) in the manner described above in connection with the compound of formula (I).

In embodiments in which the compound of formula (Ia) is conjugated to an antibody through a Linker Unit, the Linker Unit may be selected from the Linker Units described above in connection with the compound of formula (I).

In another embodiment, the present disclosure provides a compound of formula (Ib),

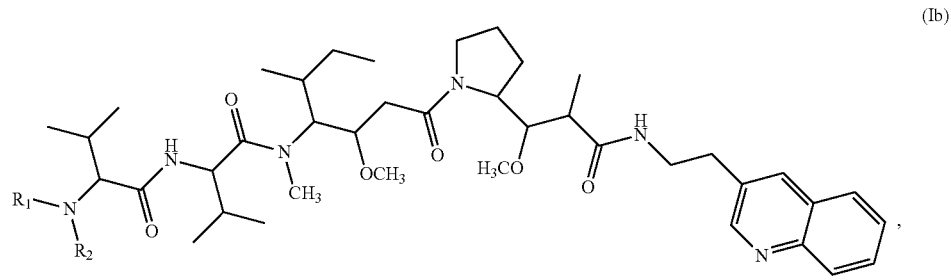

(Ib)

or a pharmaceutically acceptable salt thereof, wherein
$R_1$ is selected from H, $(C_1-C_6)$ alkyl, $(C_2-C_6)$ alkenyl, $(C_2-C_6)$ alkynyl, a Protecting Group or a Linker Unit; and
$R_2$ is selected from H, $(C_1-C_6)$ alkyl, $(C_2-C_6)$ alkenyl or $(C_2-C_6)$ alkynyl.

In one embodiment, $R_1$ is H, $(C_1-C_6)$ alkyl or a Linker Unit. In another embodiment, $R_1$ is H or $(C_1-C_6)$ alkyl. In another embodiment, $R_1$ is H or a Linker Unit. In another embodiment, $R_1$ is $(C_1-C_6)$ alkyl or a Linker Unit. In another embodiment, $R_1$ is H, methyl or a Linker Unit. In another embodiment, $R_1$ is H or methyl. In another embodiment, $R_1$ is H or a Linker Unit. In another embodiment, $R_1$ is methyl or a Linker Unit. In another embodiment, $R_1$ is H. In another embodiment, $R_1$ is methyl. In another embodiment, $R_1$ is a Linker Unit.

In one embodiment, $R_2$ is H or $(C_1-C_6)$ alkyl. In another embodiment, $R_2$ is H or methyl. In another embodiment, $R_2$ is H. In another embodiment, $R_2$ is $(C_1-C_6)$ alkyl. In another embodiment, $R_2$ is methyl.

In one embodiment, $R_1$ is H, $(C_1-C_6)$ alkyl or a Linker Unit and $R_2$ is H or $(C_1-C_6)$ alkyl. In another embodiment, $R_1$ is H or $(C_1-C_6)$ alkyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is $(C_1-C_6)$ alkyl or a Linker Unit and $R_2$ is H or $(C_1-C_6)$ alkyl. In another embodiment, $R_1$ is H, methyl or a Linker Unit and $R_2$ is H or $(C_1-C_6)$ alkyl. In another embodiment, $R_1$ is H or methyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is methyl or a Linker Unit and $R_2$ is H or $(C_1-C_6)$ alkyl. In another embodiment, $R_1$ is H and $R_2$ is H or $(C_1-C_6)$ alkyl. In another embodiment, $R_1$ is methyl and $R_2$ is H or $(C_1-C_6)$ alkyl. In another embodiment, $R_1$ is a Linker Unit and $R_2$ is H or $(C_1-C_6)$ alkyl.

In one embodiment, $R_1$ is H, $(C_1-C_6)$ alkyl or a Linker Unit and $R_2$ is H or methyl. In another embodiment, $R_1$ is H, $(C_1-C_6)$ alkyl or a Linker Unit and $R_2$ is H. In another embodiment, $R_1$ is H, $(C_1-C_6)$ alkyl or a Linker Unit and $R_2$ is $(C_1-C_6)$ alkyl. In another embodiment, $R_1$ is H, $(C_1-C_6)$ alkyl or a Linker Unit and $R_2$ is methyl.

In one embodiment, $R_1$ is methyl and $R_2$ is methyl. In another embodiment, $R_1$ is H and $R_2$ is methyl. In another embodiment, $R_1$ is H and $R_2$ is H. In another embodiment, $R_1$ is a Linker Unit and $R_2$ is methyl. In another embodiment, $R_1$ is a Linker Unit and $R_2$ is H.

In one embodiment, the compound of formula (Ib) may be conjugated to an antibody, e.g., selected from the antibodies described above in connection with the compound of formula (I). The antibody may be conjugated to the compound of formula (Ib) in the manner described above in connection with the compound of formula (I).

In embodiments in which the compound of formula (Ib) is conjugated to an antibody through a Linker Unit, the Linker Unit may be selected from the Linker Units described above in connection with the compound of formula (I).

In another embodiment, the present disclosure provides a compound of formula (Ic), or a pharmaceutically acceptable salt thereof, wherein
$R_1$ is selected from H, $(C_1-C_6)$ alkyl, $(C_2-C_6)$ alkenyl, $(C_2-C_6)$ alkynyl, a Protecting Group or a Linker Unit; and
$R_2$ is selected from H, $(C_1-C_6)$ alkyl, $(C_2-C_6)$ alkenyl or $(C_2-C_6)$ alkynyl.

In one embodiment, $R_1$ is H, $(C_1-C_6)$ alkyl or a Linker Unit. In another embodiment, $R_1$ is H or $(C_1-C_6)$ alkyl. In another embodiment, $R_1$ is H or a Linker Unit. In another embodiment, $R_1$ is $(C_1-C_6)$ alkyl or a Linker Unit. In another embodiment, $R_1$ is H, methyl or a Linker Unit. In another embodiment, $R_1$ is H or methyl. In another embodiment, $R_1$ is H or a Linker Unit. In another embodiment, $R_1$ is methyl or a Linker Unit. In another embodiment, $R_1$ is H. In another embodiment, $R_1$ is methyl. In another embodiment, $R_1$ is a Linker Unit.

In one embodiment, $R_2$ is H or $(C_1-C_6)$ alkyl. In another embodiment, $R_2$ is H or methyl. In another embodiment, $R_2$ is H. In another embodiment, $R_2$ is $(C_1-C_6)$ alkyl. In another embodiment, $R_2$ is methyl.

In one embodiment, $R_1$ is H, $(C_1-C_6)$ alkyl or a Linker Unit and $R_2$ is H or $(C_1-C_6)$ alkyl. In another embodiment, $R_1$ is H or $(C_1-C_6)$ alkyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is $(C_1-C_6)$ alkyl or a Linker Unit and $R_2$ is H or $(C_1-C_6)$ alkyl. In another embodiment, $R_1$ is H, methyl or a Linker Unit and $R_2$ is H or $(C_1-C_6)$ alkyl. In another embodiment, $R_1$ is H or methyl and $R_2$ is H or $(C_1-C_6)$ alkyl. In another embodiment, R is H or a Linker Unit and $R_2$ is H or $(C_1-C_6)$ alkyl. In another embodiment, $R_1$ is methyl or a Linker Unit and $R_2$ is H or $(C_1-C_6)$ alkyl. In another embodiment, $R_1$ is H and $R_2$ is H or $(C_1-C_6)$ alkyl. In another embodiment, $R_1$ is methyl and $R_2$ is H or $(C_1-C_6)$ alkyl. In another embodiment, $R_1$ is a Linker Unit and $R_2$ is H or $(C_1-C_6)$ alkyl.

In one embodiment, $R_1$ is H, $(C_1-C_6)$ alkyl or a Linker Unit and $R_2$ is H or methyl. In another embodiment, $R_1$ is H, $(C_1-C_6)$ alkyl or a Linker Unit and $R_2$ is H. In another embodiment, $R_1$ is H, $(C_1-C_6)$ alkyl or a Linker Unit and $R_2$ is $(C_1-C_6)$ alkyl. In another embodiment, $R_1$ is H, $(C_1-C_6)$ alkyl or a Linker Unit and $R_2$ is methyl.

In one embodiment, $R_1$ is methyl and $R_2$ is methyl. In another embodiment, $R_1$ is H and $R_2$ is methyl. In another embodiment, $R_1$ is H and $R_2$ is H. In another embodiment, $R_1$ is a Linker Unit and $R_2$ is methyl. In another embodiment, $R_1$ is a Linker Unit and $R_2$ is H.

In one embodiment, the compound of formula (Ic) may be conjugated to an antibody, e.g., selected from the antibodies described above in connection with the compound of formula (I). The antibody may be conjugated to the compound of formula (Ic) in the manner described above in connection with the compound of formula (I).

In embodiments in which the compound of formula (Ic) is conjugated to an antibody through a Linker Unit, the Linker Unit may be selected from the Linker Units described above in connection with the compound of formula (I).

In another embodiment, the present disclosure provides a compound of formula (Id),

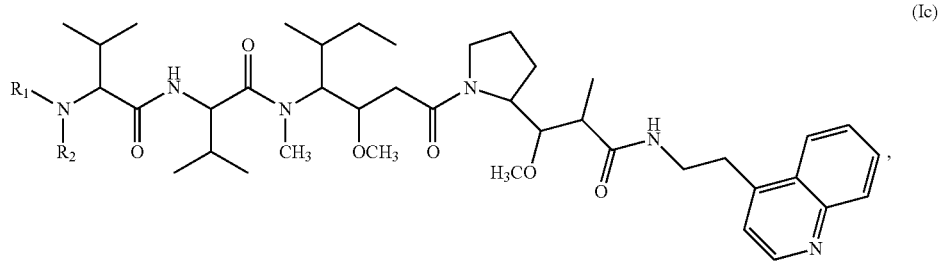

(Ic)

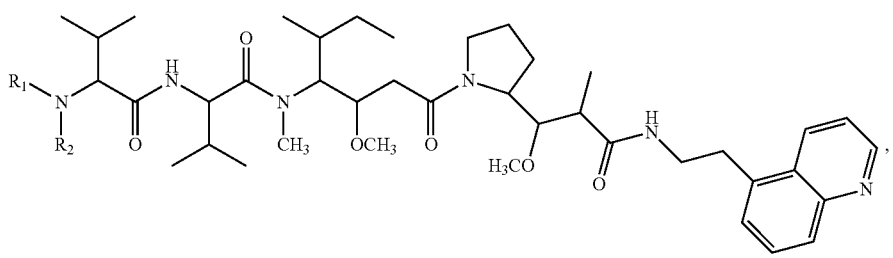

(Id)

or a pharmaceutically acceptable salt thereof, wherein
$R_1$ is selected from H, $(C_1-C_6)$ alkyl, $(C_2-C_6)$ alkenyl, $(C_2-C_6)$ alkynyl, a Protecting Group or a Linker Unit; and
$R_2$ is selected from H, $(C_1-C_6)$ alkyl, $(C_2-C_6)$ alkenyl or $(C_2-C_6)$ alkynyl.

In one embodiment, $R_1$ is H, $(C_1-C_6)$ alkyl or a Linker Unit. In another embodiment, $R_1$ is H or $(C_1-C_6)$ alkyl. In another embodiment, $R_1$ is H or a Linker Unit. In another embodiment, $R_1$ is $(C_1-C_6)$ alkyl or a Linker Unit. In another embodiment, $R_1$ is H, methyl or a Linker Unit. In another embodiment, $R_1$ is H or methyl. In another embodiment, $R_1$ is H or a Linker Unit. In another embodiment, $R_1$ is methyl or a Linker Unit. In another embodiment, $R_1$ is H. In another embodiment, $R_1$ is methyl. In another embodiment, $R_1$ is a Linker Unit.

In one embodiment, $R_2$ is H or $(C_1-C_6)$ alkyl. In another embodiment, $R_2$ is H or methyl. In another embodiment, $R_2$ is H. In another embodiment, $R_2$ is $(C_1-C_6)$ alkyl. In another embodiment, $R_2$ is methyl.

In one embodiment, $R_1$ is methyl and $R_2$ is methyl. In another embodiment, $R_1$ is H and $R_2$ is methyl. In another embodiment, $R_1$ is H and $R_2$ is H. In another embodiment, $R_1$ is a Linker Unit and $R_2$ is methyl. In another embodiment, $R_1$ is a Linker Unit and $R_2$ is H.

In one embodiment, the compound of formula (Id) may be conjugated to an antibody, e.g., selected from the antibodies described above in connection with the compound of formula (I). The antibody may be conjugated to the compound of formula (Id) in the manner described above in connection with the compound of formula (I).

In embodiments in which the compound of formula (Id) is conjugated to an antibody through a Linker Unit, the Linker Unit may be selected from the Linker Units described above in connection with the compound of formula (I).

In another embodiment, the present disclosure provides a compound of formula (Ie),

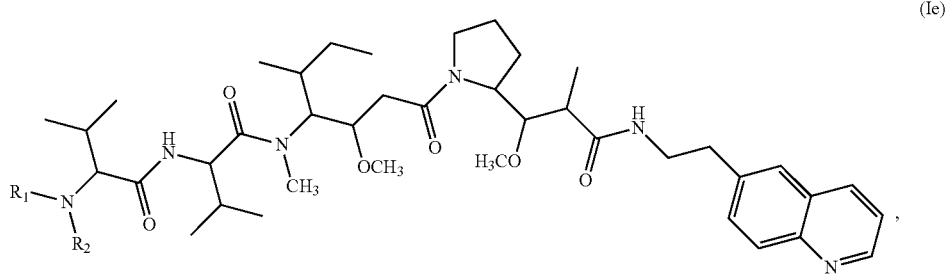

(Ie)

In one embodiment, $R_1$ is H, $(C_1-C_6)$ alkyl or a Linker Unit and $R_2$ is H or $(C_1-C_6)$ alkyl. In another embodiment, $R_1$ is H or $(C_1-C_6)$ alkyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is $(C_1-C_6)$ alkyl or a Linker Unit and $R_2$ is H or $(C_1-C_6)$ alkyl. In another embodiment, $R_1$ is H, methyl or a Linker Unit and $R_2$ is H or $(C_1-C_6)$ alkyl. In another embodiment, $R_1$ is H or methyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is methyl or a Linker Unit and $R_2$ is H or $(C_1-C_6)$ alkyl. In another embodiment, $R_1$ is H and $R_2$ is H or $(C_1-C_6)$ alkyl. In another embodiment, $R_1$ is methyl and $R_2$ is H or $(C_1-C_6)$ alkyl. In another embodiment, $R_1$ is a Linker Unit and $R_2$ is H or $(C_1-C_6)$ alkyl.

In one embodiment, $R_1$ is H, $(C_1-C_6)$ alkyl or a Linker Unit and $R_2$ is H or methyl. In another embodiment, $R_1$ is H, $(C_1-C_6)$ alkyl or a Linker Unit and $R_2$ is H. In another embodiment, $R_1$ is H, $(C_1-C_6)$ alkyl or a Linker Unit and $R_2$ is $(C_1-C_6)$ alkyl. In another embodiment, $R_1$ is H, $(C_1-C_6)$ alkyl or a Linker Unit and $R_2$ is methyl.

or a pharmaceutically acceptable salt thereof, wherein
$R_1$ is selected from H, $(C_1-C_6)$ alkyl, $(C_2-C_6)$ alkenyl, $(C_2-C_6)$ alkynyl, a Protecting Group or a Linker Unit; and
$R_2$ is selected from H, $(C_1-C_6)$ alkyl, $(C_2-C_6)$ alkenyl or $(C_2-C_6)$ alkynyl.

In one embodiment, $R_1$ is H, $(C_1-C_6)$ alkyl or a Linker Unit. In another embodiment, $R_1$ is H or $(C_1-C_6)$ alkyl. In another embodiment, $R_1$ is H or a Linker Unit. In another embodiment, $R_1$ is $(C_1-C_6)$ alkyl or a Linker Unit. In another embodiment, $R_1$ is H, methyl or a Linker Unit. In another embodiment, $R_1$ is H or methyl. In another embodiment, $R_1$ is H or a Linker Unit. In another embodiment, $R_1$ is methyl or a Linker Unit. In another embodiment, $R_1$ is H. In another embodiment, $R_1$ is methyl. In another embodiment, $R_1$ is a Linker Unit.

In one embodiment, $R_2$ is H or $(C_1-C_6)$ alkyl. In another embodiment, $R_2$ is H or methyl. In another embodiment, $R_2$ is H. In another embodiment, $R_2$ is $(C_1-C_6)$ alkyl. In another embodiment, $R_2$ is methyl.

In one embodiment, $R_1$ is H, $(C_1-C_6)$ alkyl or a Linker Unit and $R_2$ is H or $(C_1-C_6)$ alkyl. In another embodiment, $R_1$ is H or $(C_1-C_6)$ alkyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is $(C_1-C_6)$ alkyl or a Linker Unit and $R_2$ is H or $(C_1-C_6)$ alkyl. In another embodiment, $R_1$ is H, methyl or a Linker Unit and $R_2$ is H or $(C_1-C_6)$ alkyl. In another embodiment, $R_1$ is H or methyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is methyl or a Linker Unit and $R_2$ is H or $(C_1-C_6)$ alkyl. In another embodiment, $R_1$ is H and $R_2$ is H or $(C_1-C_6)$ alkyl. In another embodiment, $R_1$ is methyl and $R_2$ is H or $(C_1-C_6)$ alkyl. In another embodiment, $R_1$ is a Linker Unit and $R_2$ is H or $(C_1-C_6)$ alkyl.

In one embodiment, $R_1$ is H, $(C_1-C_6)$ alkyl or a Linker Unit and $R_2$ is H or methyl. In another embodiment, $R_1$ is H, $(C_1-C_6)$ alkyl or a Linker Unit and $R_2$ is H. In another embodiment, $R_1$ is H, $(C_1-C_6)$ alkyl or a Linker Unit and $R_2$ is $(C_1-C_6)$ alkyl. In another embodiment, $R_1$ is H, $(C_1-C_6)$ alkyl or a Linker Unit and $R_2$ is methyl.

In one embodiment, $R_1$ is methyl and $R_2$ is methyl. In another embodiment, $R_1$ is H and $R_2$ is methyl. In another embodiment, $R_1$ is H and $R_2$ is H. In another embodiment, $R_1$ is a Linker Unit and $R_2$ is methyl. In another embodiment, $R_1$ is a Linker Unit and $R_2$ is H.

In one embodiment, the compound of formula (Ie) may be conjugated to an antibody, e.g., selected from the antibodies described above in connection with the compound of formula (I). The antibody may be conjugated to the compound of formula (Ie) in the manner described above in connection with the compound of formula (I).

In embodiments in which the compound of formula (Ie) is conjugated to an antibody through a Linker Unit, the Linker Unit may be selected from the Linker Units described above in connection with the compound of formula (I).

In another embodiment, the present disclosure provides a compound of formula (If), is H or a Linker Unit. In another embodiment, $R_1$ is methyl or a Linker Unit. In another embodiment, $R_1$ is H. In another embodiment, $R_1$ is methyl. In another embodiment, $R_1$ is a Linker Unit.

In one embodiment, $R_2$ is H or $(C_1-C_6)$ alkyl. In another embodiment, $R_2$ is H or methyl. In another embodiment, $R_2$ is H. In another embodiment, $R_2$ is $(C_1-C_6)$ alkyl. In another embodiment, $R_2$ is methyl.

In one embodiment, $R_1$ is H, $(C_1-C_6)$ alkyl or a Linker Unit and $R_2$ is H or $(C_1-C_6)$ alkyl. In another embodiment, $R_1$ is H or $(C_1-C_6)$ alkyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is $(C_1-C_6)$ alkyl or a Linker Unit and $R_2$ is H or $(C_1-C_6)$ alkyl. In another embodiment, $R_1$ is H, methyl or a Linker Unit and $R_2$ is H or $(C_1-C_6)$ alkyl. In another embodiment, $R_1$ is H or methyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is methyl or a Linker Unit and $R_2$ is H or $(C_1-C_6)$ alkyl. In another embodiment, $R_1$ is H and $R_2$ is H or $(C_1-C_6)$ alkyl. In another embodiment, $R_1$ is methyl and $R_2$ is H or $(C_1-C_6)$ alkyl. In another embodiment, $R_1$ is a Linker Unit and $R_2$ is H or $(C_1-C_6)$ alkyl.

In one embodiment, $R_1$ is H, $(C_1-C_6)$ alkyl or a Linker Unit and $R_2$ is H or methyl. In another embodiment, $R_1$ is H, $(C_1-C_6)$ alkyl or a Linker Unit and $R_2$ is H. In another embodiment, $R_1$ is H, $(C_1-C_6)$ alkyl or a Linker Unit and $R_2$ is $(C_1-C_6)$ alkyl. In another embodiment, $R_1$ is H, $(C_1-C_6)$ alkyl or a Linker Unit and $R_2$ is methyl.

In one embodiment, $R_1$ is methyl and $R_2$ is methyl. In another embodiment, $R_1$ is H and $R_2$ is methyl. In another embodiment, $R_1$ is H and $R_2$ is H. In another embodiment, $R_1$ is a Linker Unit and $R_2$ is methyl. In another embodiment, $R_1$ is a Linker Unit and $R_2$ is H.

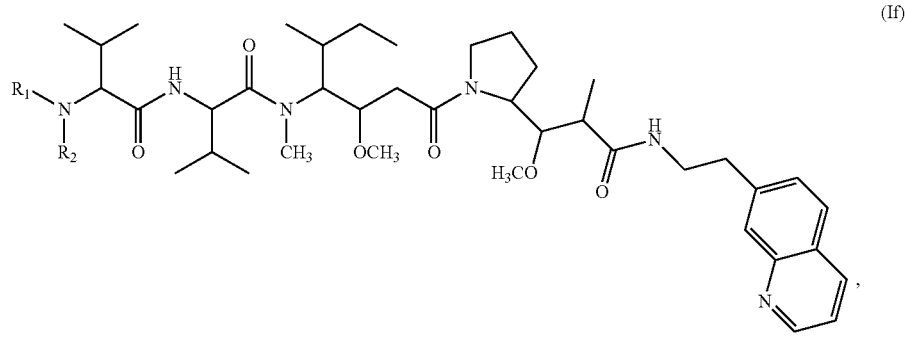

(If)

or a pharmaceutically acceptable salt thereof, wherein $R_1$ is selected from H, $(C_1-C_6)$ alkyl, $(C_2-C_6)$ alkenyl, $(C_2-C_6)$ alkynyl, a Protecting Group or a Linker Unit; and $R_2$ is selected from H, $(C_1-C_6)$ alkyl, $(C_2-C_6)$ alkenyl or $(C_2-C_6)$ alkynyl.

In one embodiment, $R_1$ is H, $(C_1-C_6)$ alkyl or a Linker Unit. In another embodiment, $R_1$ is H or $(C_1-C_6)$ alkyl. In another embodiment, $R_1$ is H or a Linker Unit. In another embodiment, $R_1$ is $(C_1-C_6)$ alkyl or a Linker Unit. In another embodiment, $R_1$ is $(C_1-C_6)$ alkyl. In another embodiment, $R_1$ is H, methyl or a Linker Unit. In another embodiment, $R_1$ is H or methyl. In another embodiment, $R_1$ In one embodiment, the compound of formula (If) may be conjugated to an antibody, e.g., selected from the antibodies described above in connection with the compound of formula (I). The antibody may be conjugated to the compound of formula (If) in the manner described above in connection with the compound of formula (I).

In embodiments in which the compound of formula (If) is conjugated to an antibody through a Linker Unit, the Linker Unit may be selected from the Linker Units described above in connection with the compound of formula (I).

In another embodiment, the present disclosure provides a compound of formula (Ig),

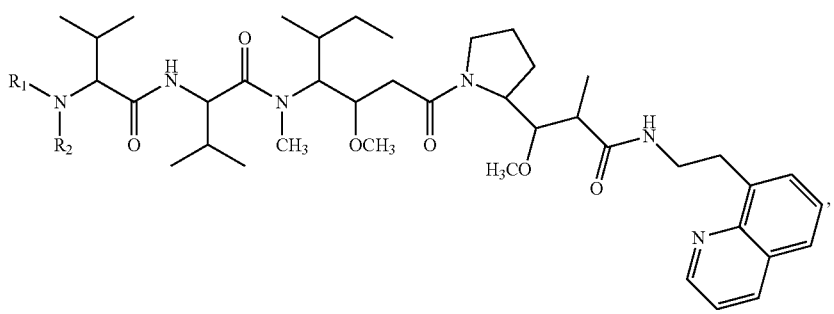

(Ig)

or a pharmaceutically acceptable salt thereof, wherein $R_1$ is selected from H, $(C_1-C_6)$ alkyl, $(C_2-C_6)$ alkenyl, $(C_2-C_6)$ alkynyl, a Protecting Group or a Linker Unit; and $R_2$ is selected from H, $(C_1-C_6)$ alkyl, $(C_2-C_6)$ alkenyl or $(C_2-C_6)$ alkynyl.

In one embodiment, $R_1$ is H, $(C_1-C_6)$ alkyl or a Linker Unit. In another embodiment, $R_1$ is H or $(C_1-C_6)$ alkyl. In another embodiment, $R_1$ is H or a Linker Unit. In another embodiment, $R_1$ is $(C_1-C_6)$ alkyl or a Linker Unit. In another embodiment, $R_1$ is H, methyl or a Linker Unit. In another embodiment, $R_1$ is H or methyl. In another embodiment, $R_1$ is H or a Linker Unit. In another embodiment, $R_1$ is methyl or a Linker Unit. In another embodiment, $R_1$ is H. In another embodiment, $R_1$ is methyl. In another embodiment, $R_1$ is a Linker Unit.

In one embodiment, $R_2$ is H or $(C_1-C_6)$ alkyl. In another embodiment, $R_2$ is H or methyl. In another embodiment, $R_2$ is H. In another embodiment, $R_2$ is $(C_1-C_6)$ alkyl. In another embodiment, $R_2$ is methyl.

In one embodiment, $R_1$ is H, $(C_1-C_6)$ alkyl or a Linker Unit and $R_2$ is H or $(C_1-C_6)$ alkyl. In another embodiment, $R_1$ is H or $(C_1-C_6)$ alkyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is $(C_1-C_6)$ alkyl or a Linker Unit and $R_2$ is H or $(C_1-C_6)$ alkyl. In another embodiment, $R_1$ is H, methyl or a Linker Unit and $R_2$ is H or $(C_1-C_6)$ alkyl. In another embodiment, $R_1$ is H or methyl and $R_2$ is H or $(C_1-C_6)$ alkyl. In another embodiment, $R_1$ is H or a Linker Unit and $R_2$ is H or $(C_1-C_6)$ alkyl. In another embodiment, $R_1$ is methyl or a Linker Unit and $R_2$ is H or $(C_1-C_6)$ alkyl. In another embodiment, $R_1$ is H and $R_2$ is H or $(C_1-C_6)$ alkyl. In another embodiment, $R_1$ is methyl and $R_2$ is H or $(C_1-C_6)$ alkyl. In another embodiment, $R_1$ is a Linker Unit and $R_2$ is H or $(C_1-C_6)$ alkyl.

In one embodiment, $R_1$ is H, $(C_1-C_6)$ alkyl or a Linker Unit and $R_2$ is H or methyl. In another embodiment, $R_1$ is H, $(C_1-C_6)$ alkyl or a Linker Unit and $R_2$ is H. In another embodiment, $R_1$ is H, $(C_1-C_6)$ alkyl or a Linker Unit and $R_2$ is $(C_1-C_6)$ alkyl. In another embodiment, $R_1$ is H, $(C_1-C_6)$ alkyl or a Linker Unit and $R_2$ is methyl.

In one embodiment, $R_1$ is methyl and $R_2$ is methyl. In another embodiment, $R_1$ is H and $R_2$ is methyl. In another embodiment, $R_1$ is H and $R_2$ is H. In another embodiment, $R_1$ is a Linker Unit and $R_2$ is methyl. In another embodiment, $R_1$ is a Linker Unit and $R_2$ is H.

In one embodiment, the compound of formula (Ig) may be conjugated to an antibody, e.g., selected from the antibodies described above in connection with the compound of formula (I). The antibody may be conjugated to the compound of formula (Ig) in the manner described above in connection with the compound of formula (I).

In embodiments in which the compound of formula (Ig) is conjugated to an antibody through a Linker Unit, the Linker Unit may be selected from the Linker Units described above in connection with the compound of formula (I).

Representative compounds of formula (I) include:

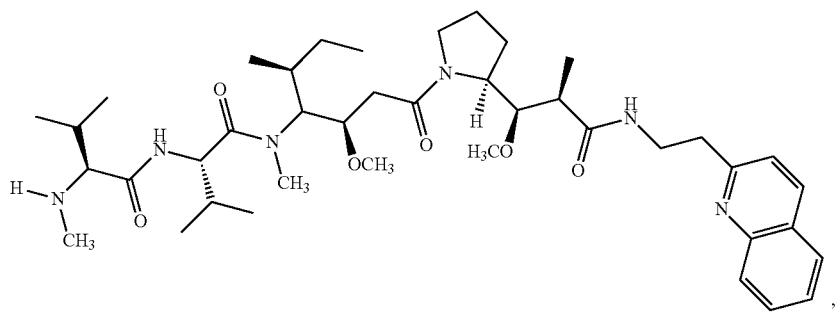

-continued
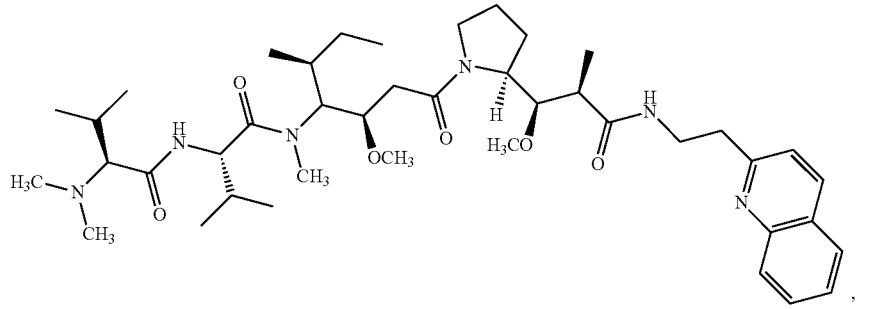
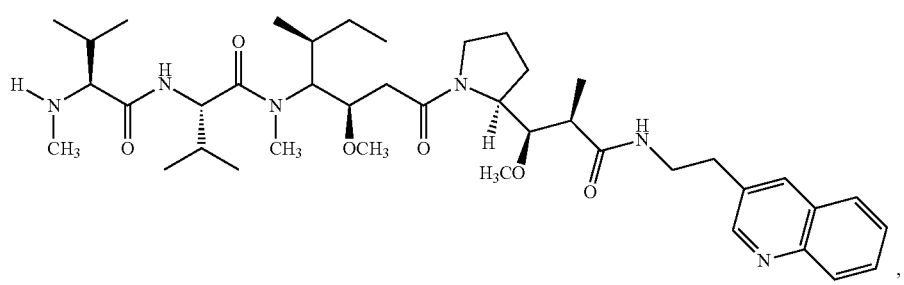
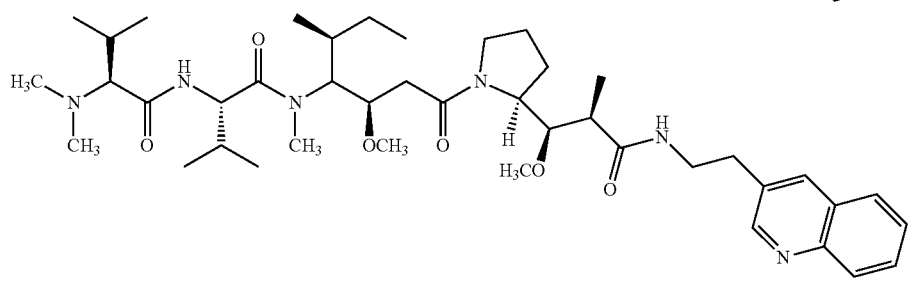
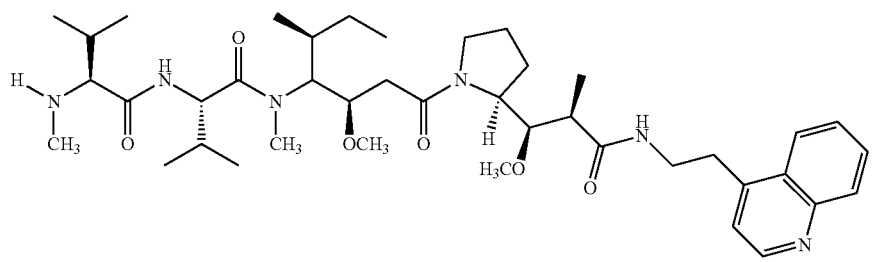
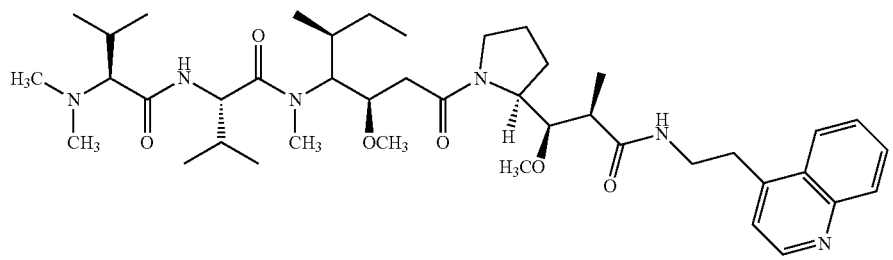
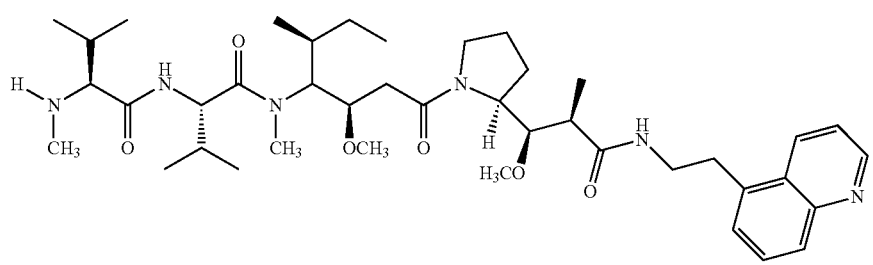

-continued
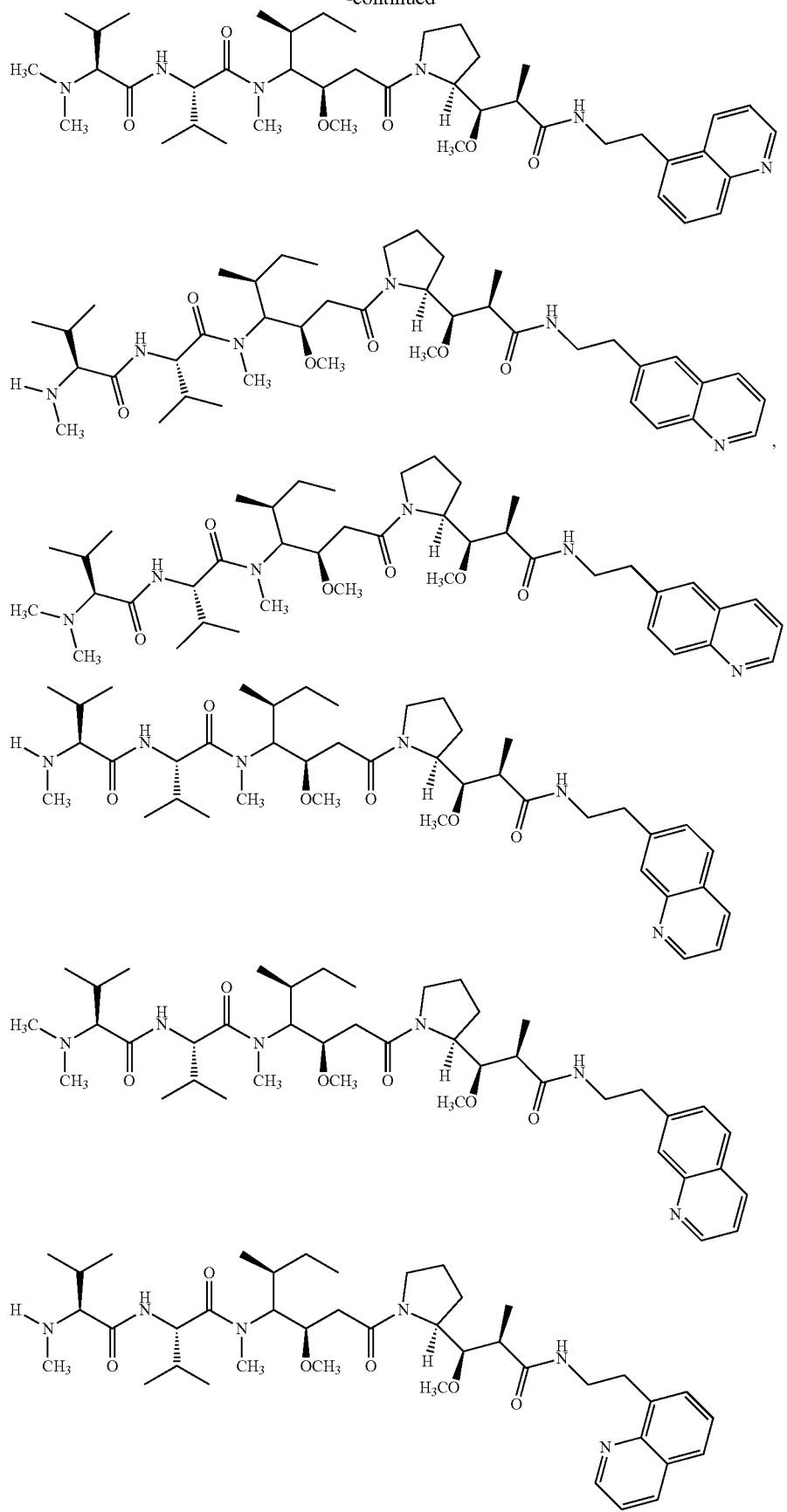

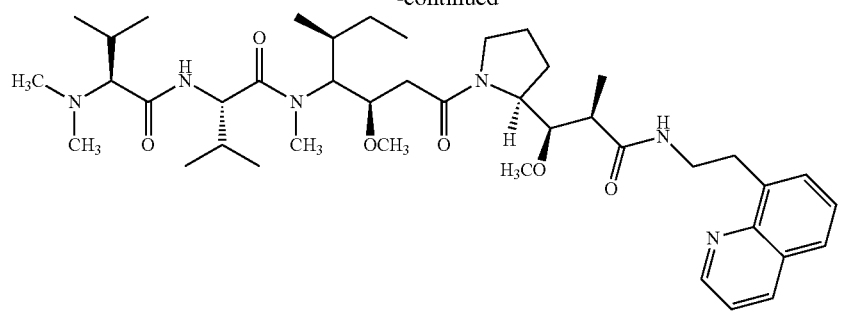
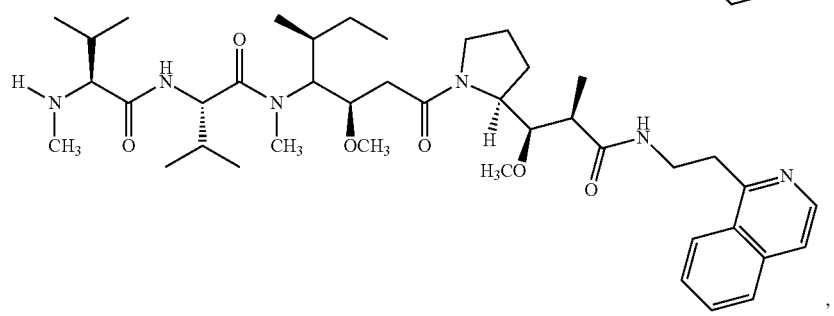
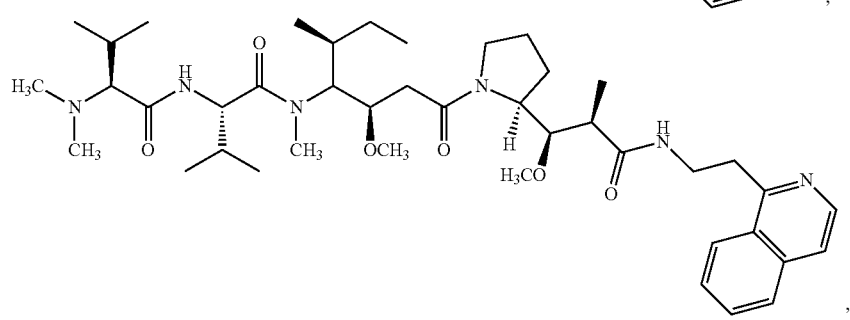
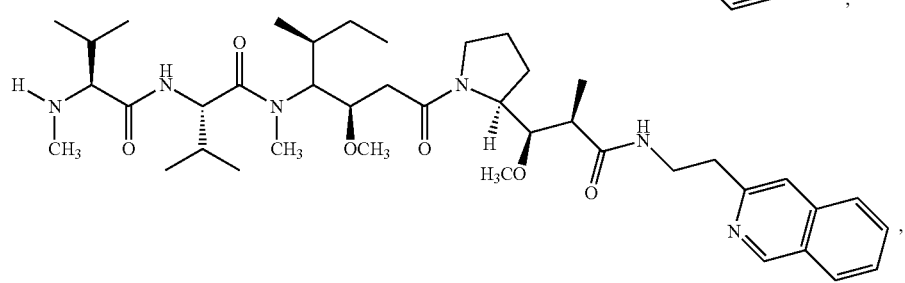
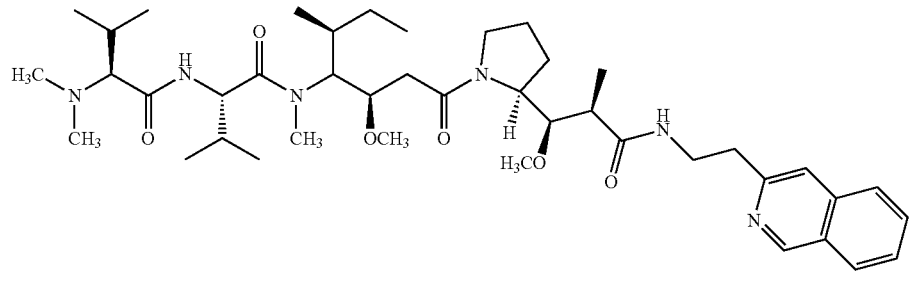
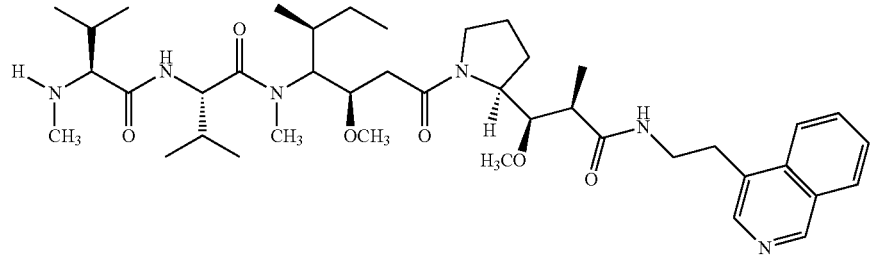

-continued
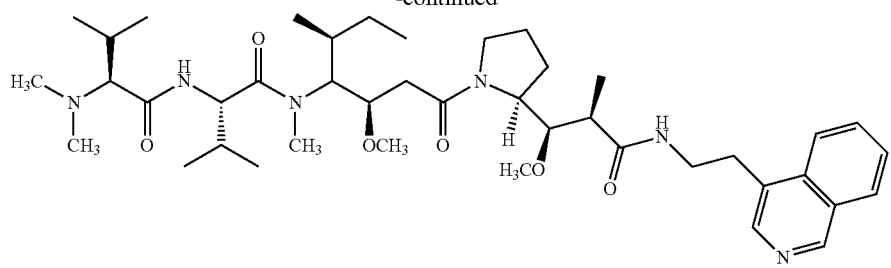
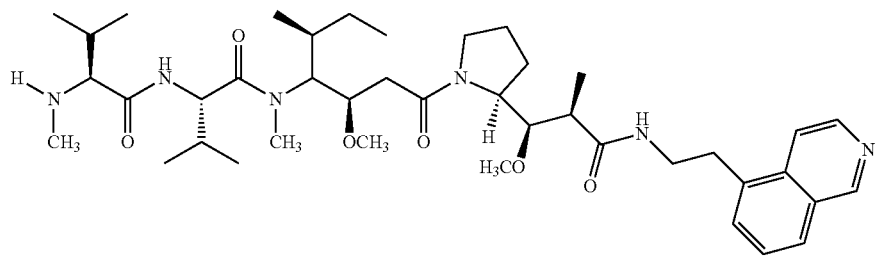
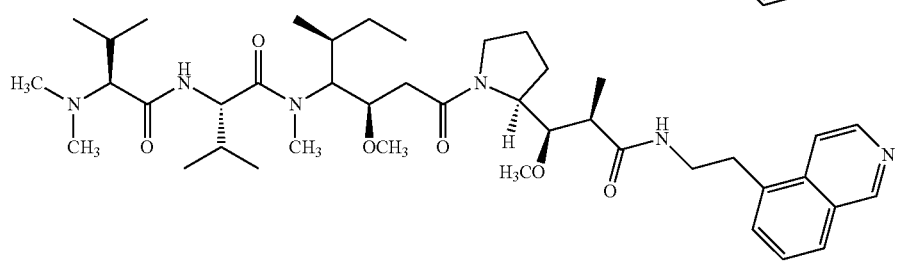
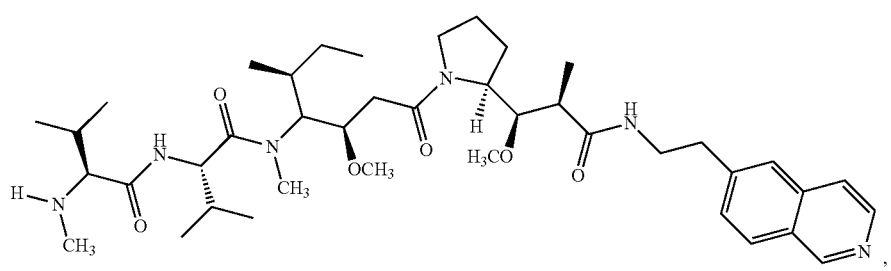
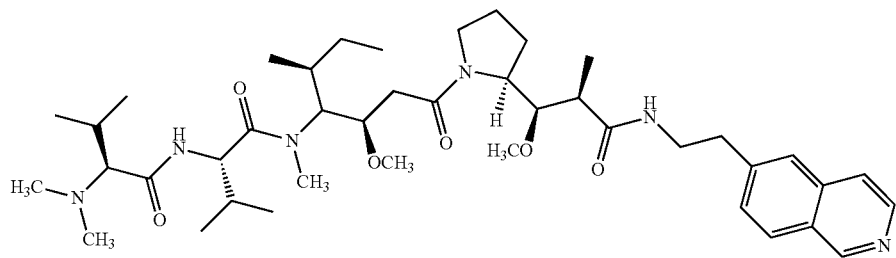
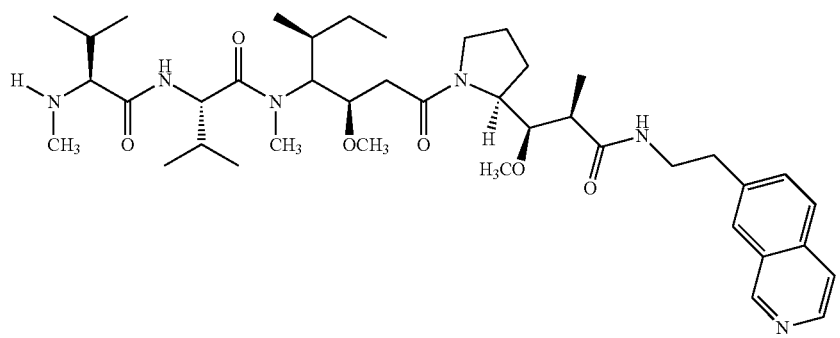

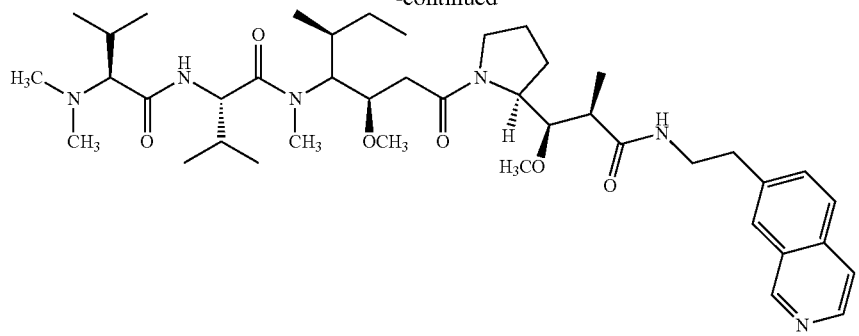
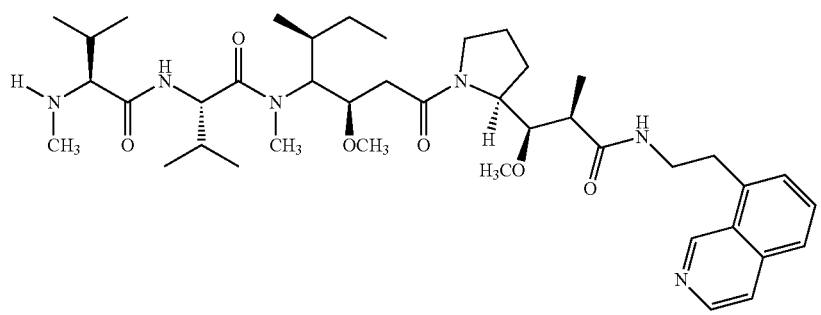
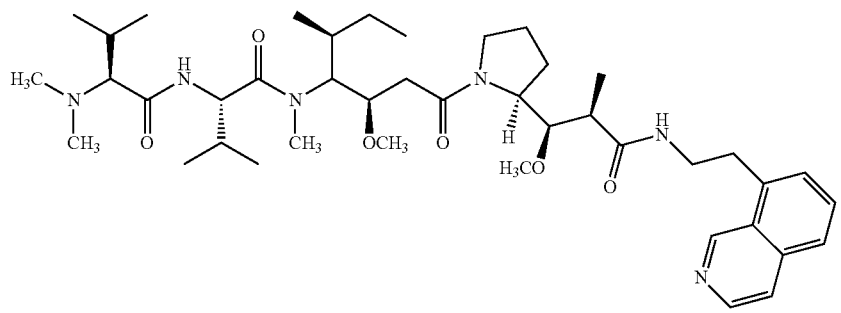
and pharmaceutically acceptable salts thereof.
In one embodiment, the compound is
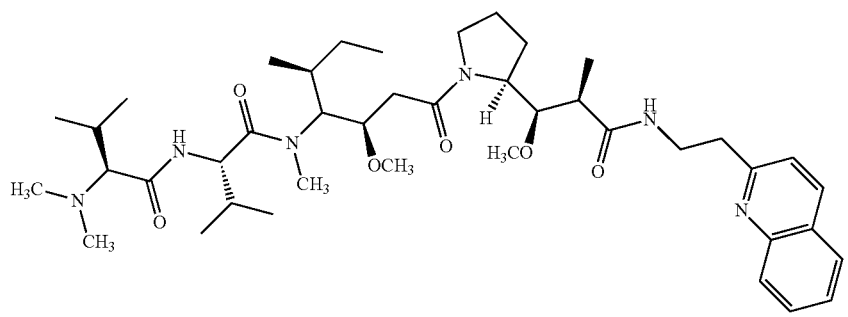 [SMILES: CC[C@H](C)C([C@@H](CC(=O)N1CCC[C@H]1[C@H](OC)[C@@H](C)C(=O)NCCc1ccc2ccccc2n1)OC)N(C)C(=O)[C@@H](NC(=O)[C@H](C(C)C)N(C)C)C(C)C]
or a pharmaceutically acceptable salt thereof.

In another embodiment, the compound is
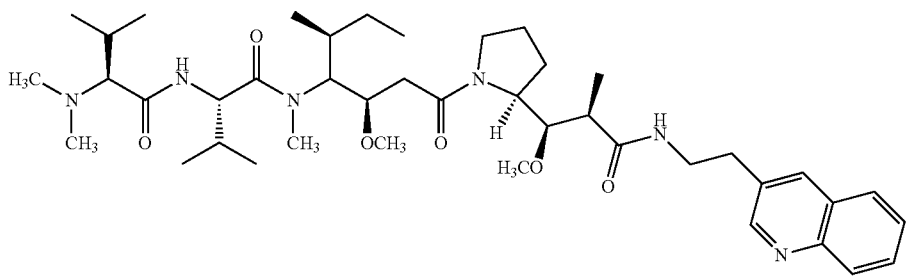 [SMILES: CC[C@H](C)C([C@@H](CC(=O)N1CCC[C@H]1[C@H](OC)[C@@H](C)C(=O)NCCc1cnc2ccccc2c1)OC)N(C)C(=O)[C@@H](NC(=O)[C@H](C(C)C)N(C)C)C(C)C]
or a pharmaceutically acceptable salt thereof.
In another embodiment, the compound is
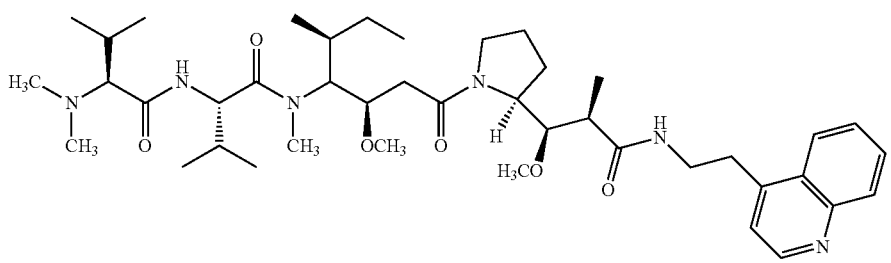 [SMILES: CC[C@H](C)C([C@@H](CC(=O)N1CCC[C@H]1[C@H](OC)[C@@H](C)C(=O)NCCc1ccnc2ccccc12)OC)N(C)C(=O)[C@@H](NC(=O)[C@H](C(C)C)N(C)C)C(C)C]
or a pharmaceutically acceptable salt thereof.
In another embodiment, the compound is
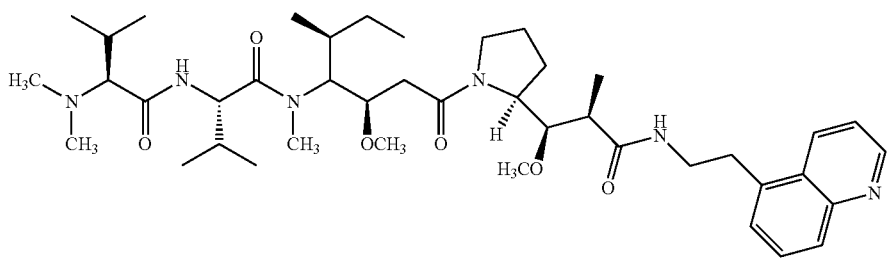 [SMILES: CC[C@H](C)C([C@@H](CC(=O)N1CCC[C@H]1[C@H](OC)[C@@H](C)C(=O)NCCc1cccc2ncccc12)OC)N(C)C(=O)[C@@H](NC(=O)[C@H](C(C)C)N(C)C)C(C)C]
or a pharmaceutically acceptable salt thereof.
In another embodiment, the compound is
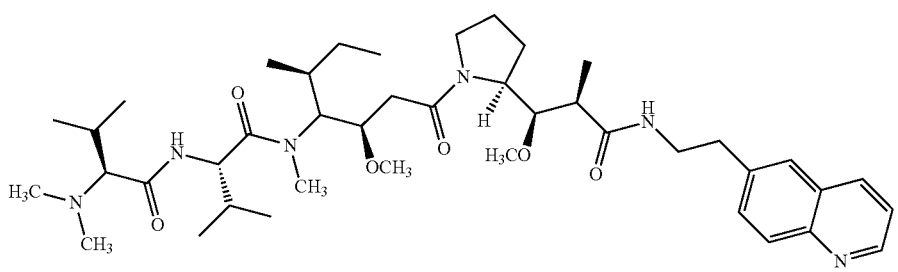 [SMILES: CC[C@H](C)C([C@@H](CC(=O)N1CCC[C@H]1[C@H](OC)[C@@H](C)C(=O)NCCc1ccc2ncccc2c1)OC)N(C)C(=O)[C@@H](NC(=O)[C@H](C(C)C)N(C)C)C(C)C]
or a pharmaceutically acceptable salt thereof.

In another embodiment, the compound is
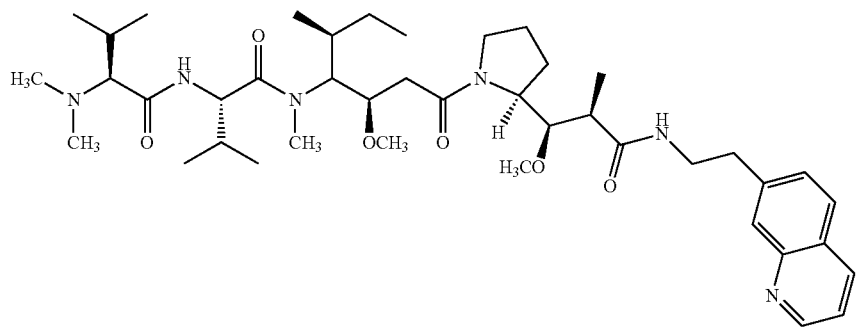 [SMILES: CC[C@H](C)C([C@@H](CC(=O)N1CCC[C@H]1[C@H](OC)[C@@H](C)C(=O)NCCc1ccc2cccnc2c1)OC)N(C)C(=O)[C@@H](NC(=O)[C@H](C(C)C)N(C)C)C(C)C]
or a pharmaceutically acceptable salt thereof.
In another embodiment, the compound is
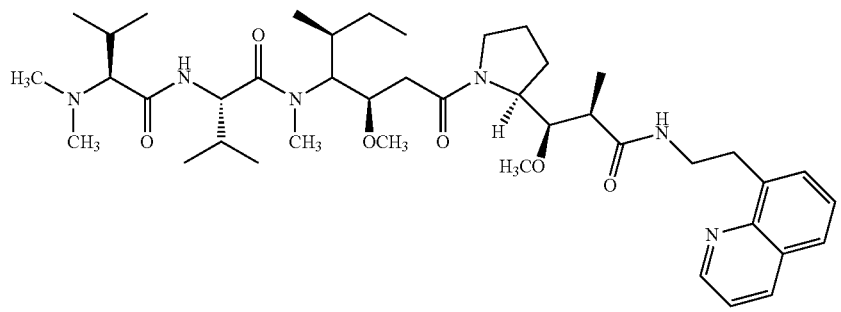 [SMILES: CC[C@H](C)C([C@@H](CC(=O)N1CCC[C@H]1[C@H](OC)[C@@H](C)C(=O)NCCc1cccc2cccnc12)OC)N(C)C(=O)[C@@H](NC(=O)[C@H](C(C)C)N(C)C)C(C)C]
or a pharmaceutically acceptable salt thereof.
In another embodiment, the compound is
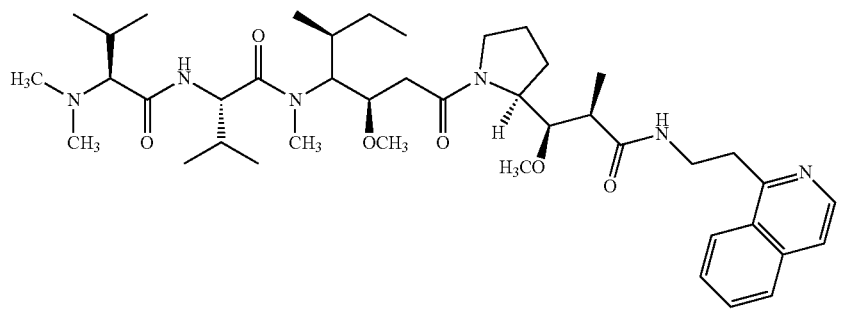 [SMILES: CC[C@H](C)C([C@@H](CC(=O)N1CCC[C@H]1[C@H](OC)[C@@H](C)C(=O)NCCc1nccc2ccccc12)OC)N(C)C(=O)[C@@H](NC(=O)[C@H](C(C)C)N(C)C)C(C)C]
or a pharmaceutically acceptable salt thereof.
In another embodiment, the compound is
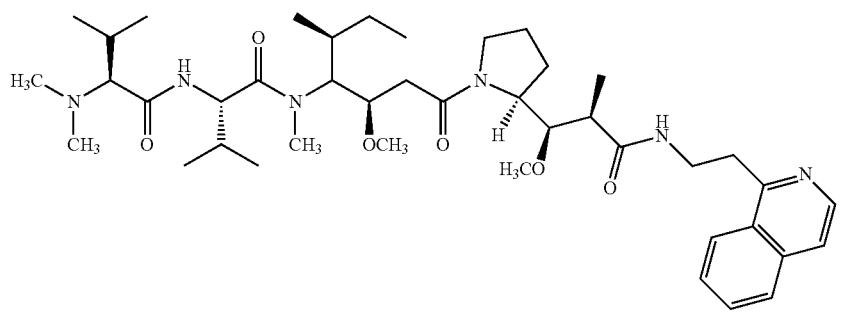 [SMILES: CC[C@H](C)C([C@@H](CC(=O)N1CCC[C@H]1[C@H](OC)[C@@H](C)C(=O)NCCc1nccc2ccccc12)OC)N(C)C(=O)[C@@H](NC(=O)[C@H](C(C)C)N(C)C)C(C)C]
or a pharmaceutically acceptable salt thereof.

In another embodiment, the compound is
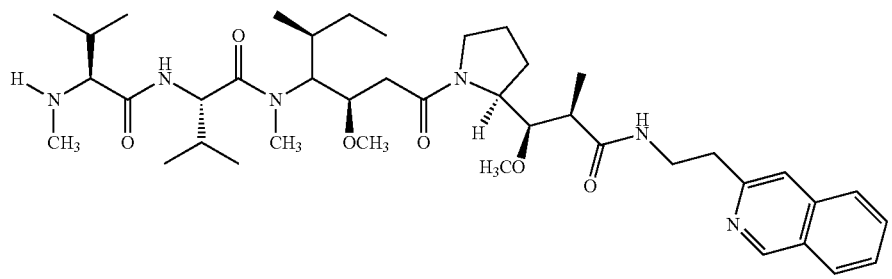 [SMILES: CC[C@H](C)C([C@@H](CC(=O)N1CCC[C@H]1[C@H](OC)[C@@H](C)C(=O)NCCc1cc2ccccc2cn1)OC)N(C)C(=O)[C@@H](NC(=O)[C@@H](NC)C(C)C)C(C)C]
or a pharmaceutically acceptable salt thereof.
In another embodiment, the compound is
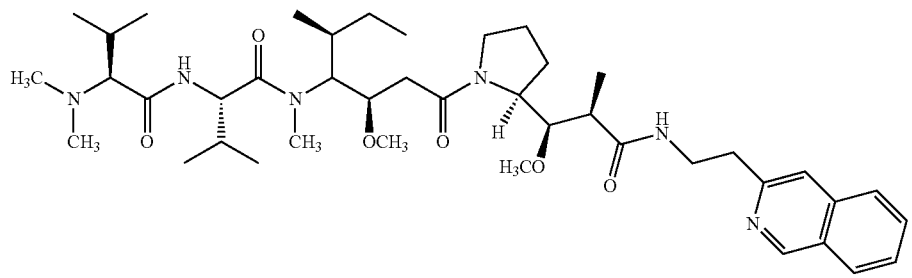 [SMILES: CC[C@H](C)C([C@@H](CC(=O)N1CCC[C@H]1[C@H](OC)[C@@H](C)C(=O)NCCc1cc2ccccc2cn1)OC)N(C)C(=O)[C@@H](NC(=O)[C@H](C(C)C)N(C)C)C(C)C]
or a pharmaceutically acceptable salt thereof.
In another embodiment, the compound is
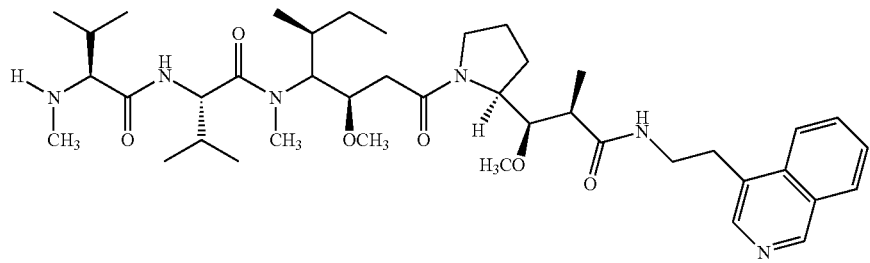 [SMILES: CC[C@H](C)C([C@@H](CC(=O)N1CCC[C@H]1[C@H](OC)[C@@H](C)C(=O)NCCc1cncc2ccccc12)OC)N(C)C(=O)[C@@H](NC(=O)[C@@H](NC)C(C)C)C(C)C]
or a pharmaceutically acceptable salt thereof.
In another embodiment, the compound is
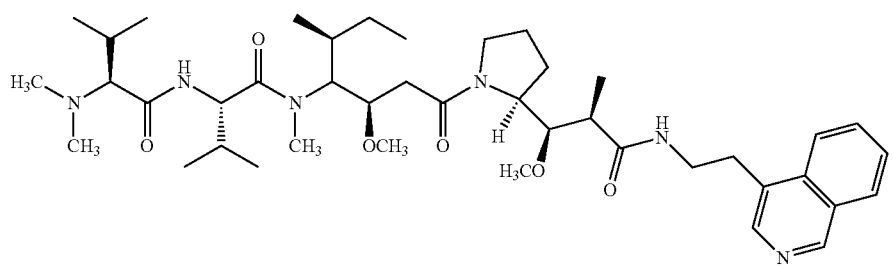 [SMILES: CC[C@H](C)C([C@@H](CC(=O)N1CCC[C@H]1[C@H](OC)[C@@H](C)C(=O)NCCc1cncc2ccccc12)OC)N(C)C(=O)[C@@H](NC(=O)[C@H](C(C)C)N(C)C)C(C)C]
or a pharmaceutically acceptable salt thereof.

In another embodiment, the compound is
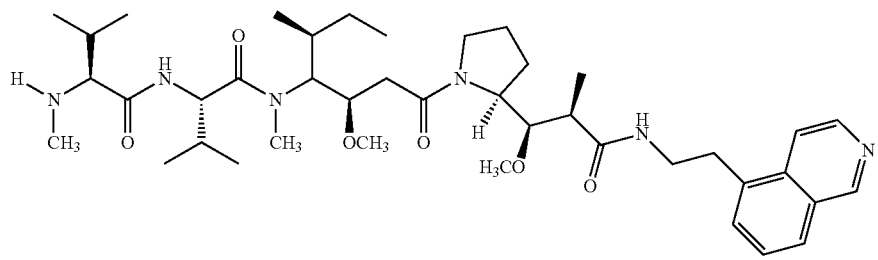 [SMILES: CC[C@H](C)C([C@@H](CC(=O)N1CCC[C@H]1[C@H](OC)[C@@H](C)C(=O)NCCc1cccc2cnccc12)OC)N(C)C(=O)[C@@H](NC(=O)[C@@H](NC)C(C)C)C(C)C]
or a pharmaceutically acceptable salt thereof.
In another embodiment, the compound is
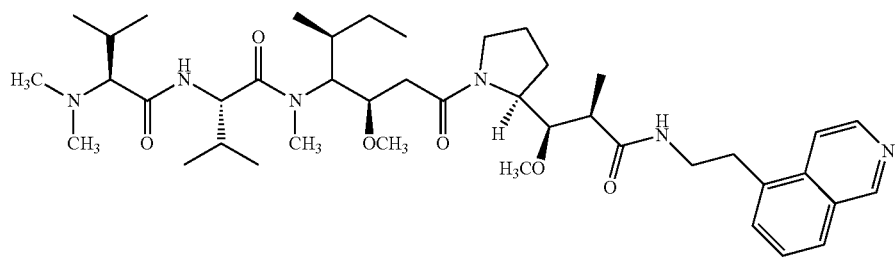 [SMILES: CC[C@H](C)C([C@@H](CC(=O)N1CCC[C@H]1[C@H](OC)[C@@H](C)C(=O)NCCc1cccc2cnccc12)OC)N(C)C(=O)[C@@H](NC(=O)[C@H](C(C)C)N(C)C)C(C)C]
or a pharmaceutically acceptable salt thereof.
In another embodiment, the compound is
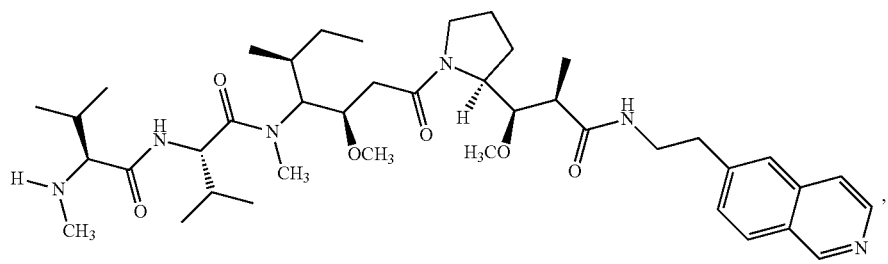 [SMILES: CC[C@H](C)C([C@@H](CC(=O)N1CCC[C@H]1[C@H](OC)[C@@H](C)C(=O)NCCc1ccc2cnccc2c1)OC)N(C)C(=O)[C@@H](NC(=O)[C@@H](NC)C(C)C)C(C)C]
or a pharmaceutically acceptable salt thereof.
In another embodiment, the compound is
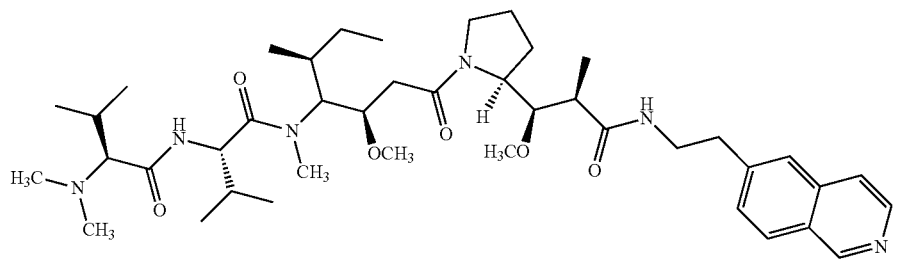 [SMILES: CC[C@H](C)C([C@@H](CC(=O)N1CCC[C@H]1[C@H](OC)[C@@H](C)C(=O)NCCc1ccc2cnccc2c1)OC)N(C)C(=O)[C@@H](NC(=O)[C@H](C(C)C)N(C)C)C(C)C]
or a pharmaceutically acceptable salt thereof.

In another embodiment, the compound is
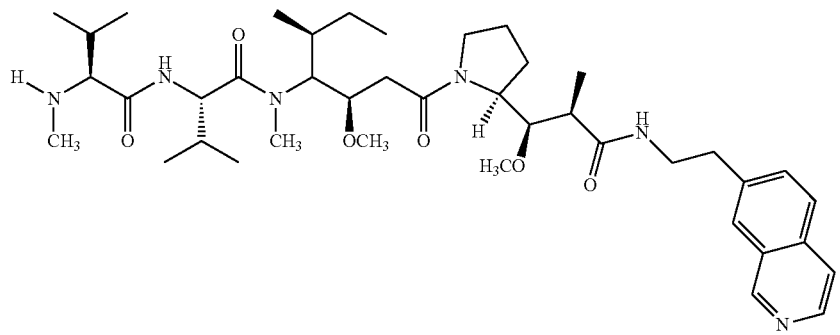 [SMILES: CC[C@H](C)C([C@@H](CC(=O)N1CCC[C@H]1[C@H](OC)[C@@H](C)C(=O)NCCc1ccc2ccncc2c1)OC)N(C)C(=O)[C@@H](NC(=O)[C@@H](NC)C(C)C)C(C)C]
or a pharmaceutically acceptable salt thereof.
In another embodiment, the compound is
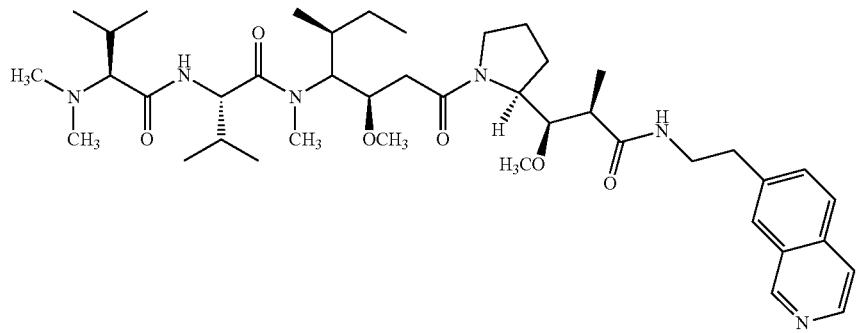 [SMILES: CC[C@H](C)C([C@@H](CC(=O)N1CCC[C@H]1[C@H](OC)[C@@H](C)C(=O)NCCc1ccc2ccncc2c1)OC)N(C)C(=O)[C@@H](NC(=O)[C@H](C(C)C)N(C)C)C(C)C]
or a pharmaceutically acceptable salt thereof.
In another embodiment, the compound is
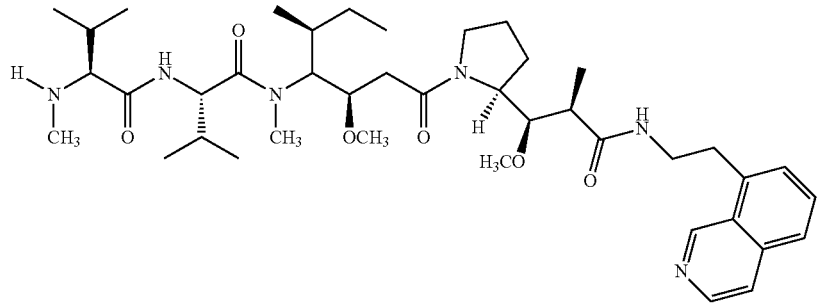 [SMILES: CC[C@H](C)C([C@@H](CC(=O)N1CCC[C@H]1[C@H](OC)[C@@H](C)C(=O)NCCc1cccc2ccncc12)OC)N(C)C(=O)[C@@H](NC(=O)[C@@H](NC)C(C)C)C(C)C]
or a pharmaceutically acceptable salt thereof.
In another embodiment, the compound is
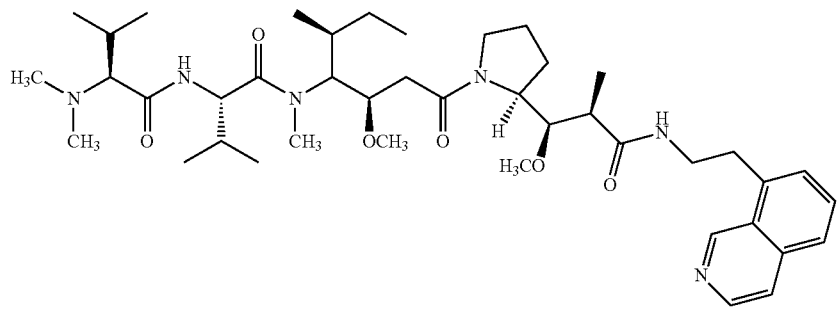
or a pharmaceutically acceptable salt thereof.

Additional representative compounds of formula (I) include:
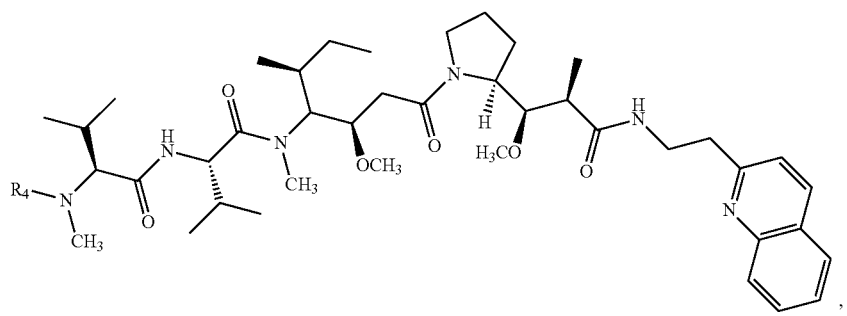,
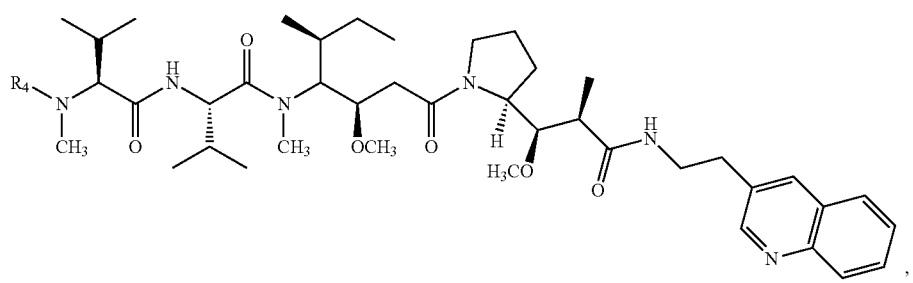,
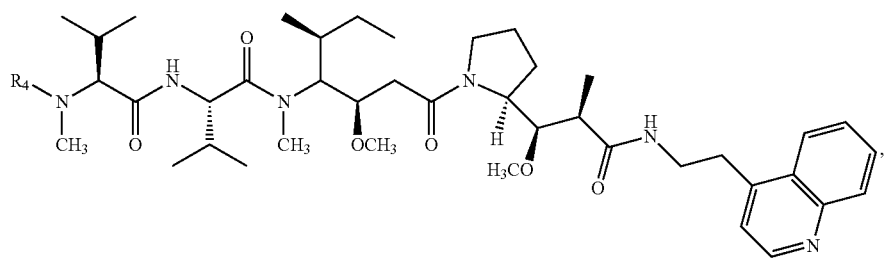,
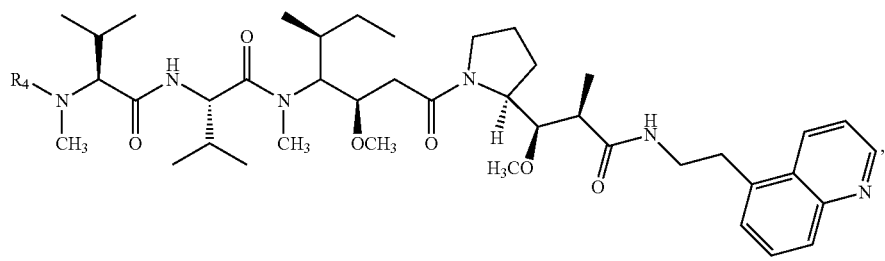,
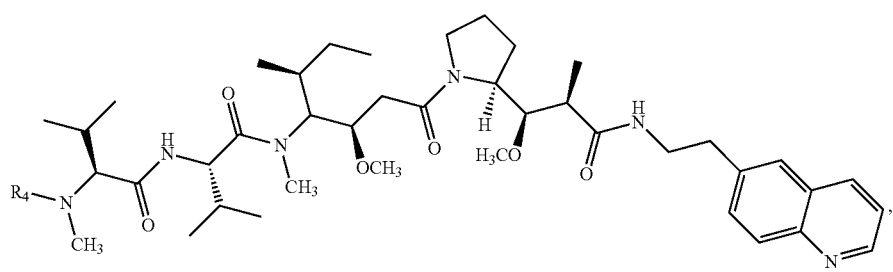,

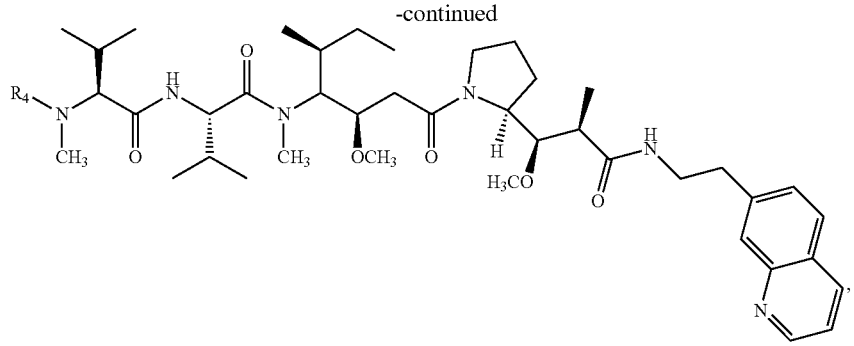
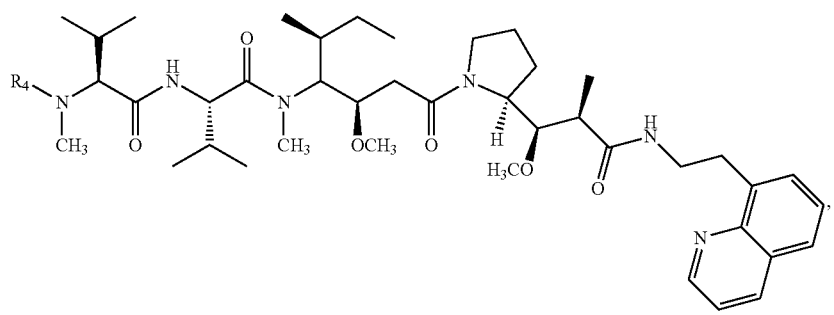
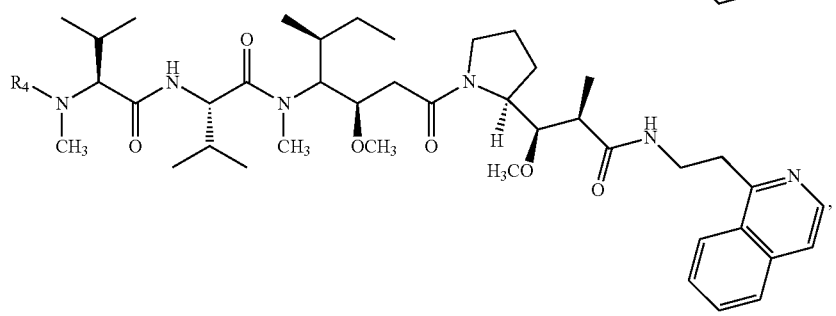
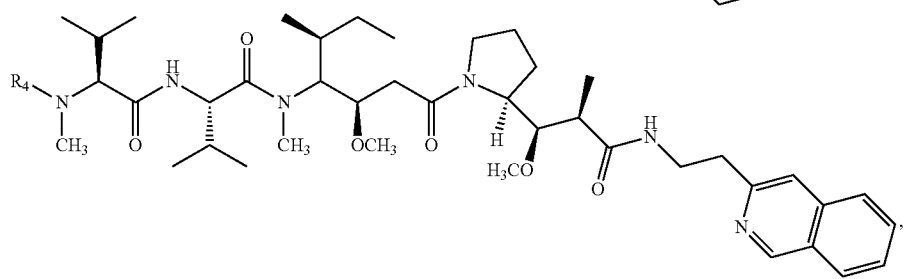
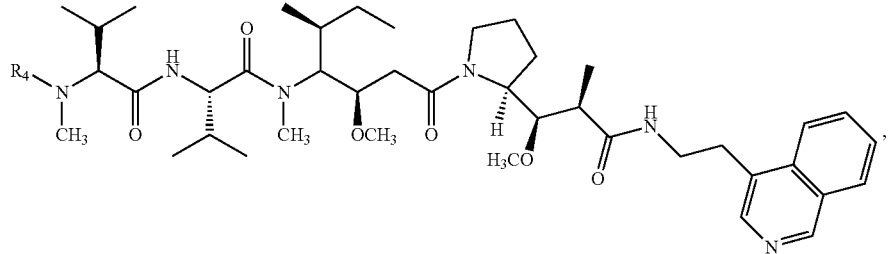
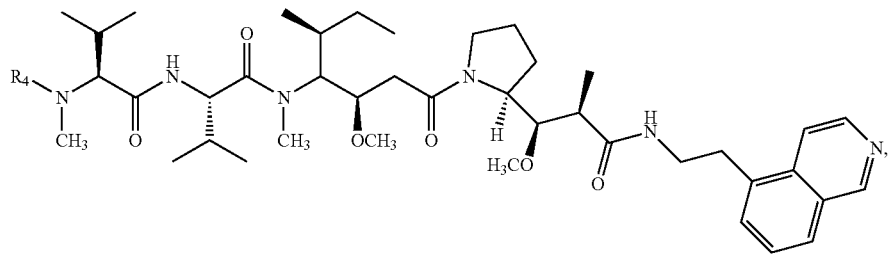

-continued

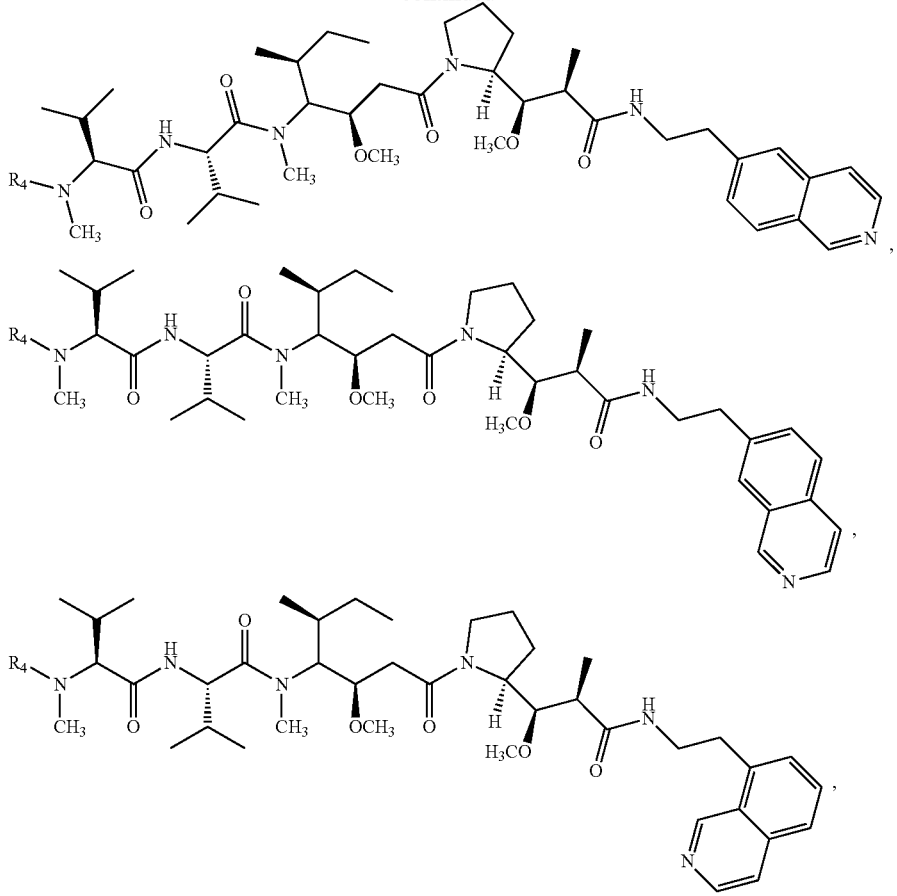

and pharmaceutically acceptable salts thereof, wherein $R_4$ is a Linker Unit having formula:

$A_aW_wY_y$, $A_a$ is maleimidocaproyl, $W_w$ is Valine-Citrulline and $Y_y$ is p-aminobenzyloxycarbonyl.

Pharmaceutical Compositions

According to another embodiment, the present disclosure provides a pharmaceutical composition comprising a compound described herein or a pharmaceutically acceptable salt thereof and a pharmaceutically acceptable carrier.

The pharmaceutical composition of the disclosure may be formulated for administration in solid or liquid form, including those adapted for administration by oral, nasal, parenteral, rectal, topical, ocular, inhalation and intra-tumor administration. Parenteral administration includes subcutaneous injections, intravenous, intramuscular or intrasternal injection or infusion techniques. In one embodiment, the compositions are administered parenterally. In another embodiment, the compositions are administered intravenously.

The pharmaceutical composition of the disclosure may be in the form of a liquid, e.g., a solution, emulsion or suspension, pellets, powders, sustained-release formulations, or any other form suitable for use. The pharmaceutical composition may comprise sterile diluents such as water, saline solution, preferably physiological saline, Ringer's solution, isotonic sodium chloride, fixed oils such as synthetic mono- or digylcerides, which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids; agents for the adjustment of tonicity such as sodium chloride or dextrose; surfactants; preservatives; wetting agents; dispersing agents; suspending agents; stabilizers; solubilizing agents; local anesthetics, e.g., lignocaine; or isotonic agent.

It should be understood that a specific dosage and treatment regimen for any particular patient will depend upon a variety of factors, including the type of patient (e.g., human), the activity of the specific compound employed, the composition employed, the manner of administration, the age, body weight, general health, sex, diet, time of administration, rate of excretion, drug combination, and the judgment of the treating physician and the nature and the severity of the particular disorder being treated. The amount of active ingredients will also depend upon the particular compound in the composition. The amount of active ingredient can be determined by standard clinical techniques. In addition, in vitro or in vivo assays can optionally be employed to help identify optimal dosage ranges.

Preferably, the compositions are formulated so that a dosage of between about 0.01 to about 20 mg/kg body weight/day of the compound of formula (I) can be administered to a patient receiving the composition. In one embodiment, the dosage administered to the patient is between about 0.01 mg/kg and about 10 mg/kg of the patient's body weight. In another embodiment, the dosage administered to the patient is between about 0.1 mg/kg and about 10 mg/kg of the patient's body weight. In yet another embodiment, the dosage administered to the patient is between about 0.1 mg/kg and about 5 mg/kg of the patient's body weight. In yet another embodiment, the dosage administered is between about 0.1 mg/kg and about 3 mg/kg of the patient's body weight. In yet another embodiment, the dosage administered is between about 1 mg/kg and about 3 mg/kg of the patient's body weight.

The pharmaceutical compositions comprise an effective amount of a compound described herein such that a suitable dosage will be obtained. Typically, this amount is at least about 0.01% of a compound by weight of the composition. In a preferred embodiment, pharmaceutical compositions are prepared so that a parenteral dosage unit contains from about 0.01% to about 2% by weight of the compound of the disclosure.

For intravenous administration, the pharmaceutical composition may comprise from about 0.01 to about 100 mg of a compound described herein per kg of the patient's body weight. In one aspect, the composition may include from about 1 to about 100 mg of a compound described herein per kg of the patient's body weight. In another aspect, the amount administered will be in the range from about 0.1 to about 25 mg of a compound described herein per kg of body weight.

The pharmaceutical compositions of the disclosure may optionally further comprise a second therapeutic agent in a therapeutically effective amount. The second therapeutic agent includes those that are known and those discovered to be effective in treating cancer. In some embodiments, the second therapeutic agent may be selected from the group consisting of a tubulin-forming inhibitor, a topoisomerase inhibitor, and a DNA binder.

Methods of Use

According to another embodiment, the present disclosure provides methods of using the compounds described herein or pharmaceutical compositions thereof. The compounds and compositions are useful for killing or inhibiting the proliferation of tumor cells or cancer cells. The compounds and compositions are also useful for treating cancer in a patient.

In some embodiments, the present disclosure provides methods of killing or inhibiting the proliferation of tumor cells or cancer cells. In some embodiments, the method comprises contacting the tumor cells or cancer cells with a compound described herein, or a pharmaceutically acceptable salt thereof, in an amount effective to kill or inhibit the proliferation of the tumor cells or cancer cells. In alternate embodiments, the method comprises contacting the tumor cells or cancer cells with a pharmaceutical composition comprising a compound of formula (I) in an amount effective to kill or inhibit the proliferation of the tumor cells or cancer cells.

In some embodiments, the method further comprises contacting the cells with an effective amount of a second therapeutic agent or a pharmaceutical composition thereof. In one embodiment, the second therapeutic agent is selected from the group consisting of a tubulin-forming inhibitor, a topoisomerase inhibitor, and a DNA binder.

The cells may be contacted with the compound described herein and the second therapeutic agent simultaneously in either the same or different compositions or sequentially in any order. The amounts of compound described herein and the second therapeutic agent and the relative timings of their contact will be selected in order to achieve the desired combined effect.

In another embodiment, the present disclosure provides a method of determining inhibition of cellular proliferation by a compound described herein. The method comprises contacting cells in a cell culture medium with the compound described herein and measuring the cytotoxic activity of the compound, whereby proliferation of the cells is inhibited. In some embodiments, the method further comprises culturing the cells for a period from about 6 hours to about 5 days.

Suitable cell lines are known to those skilled in the art and include those used for evaluating other anti-cancer drugs. Such cell lines include, but are not limited to, BXPC-3 (pancreas); MCF-7 (breast); SF-268 (CNS); NCI-H460 (lung); KM20L2 (colon); DU-145 (prostate); 786-0, (renal cell carcinoma); Caki-1 (renal cell carcinoma); L428 (Hodgkin's disease); UMRC-3 (renal cell carcinoma); LP-1 (human myeloma); and U251 (glioblastoma). In some embodiments, the cells are obtained from a patient having a disease to be treated (e.g., cancer) or from a relevant cell line.

In another embodiment, the present disclosure provides a method of measuring cell viability in the presence of a compound described herein. The method comprises contacting cells in a cell culture medium with the compound of described herein, culturing the cells for a period from about 6 hours to about 5 days, preferably 96 hours; and measuring cell viability. In some embodiments, the cells are obtained from a patient having a disease to be treated (e.g., cancer) or from a relevant cell line.

In another embodiment, the present disclosure provides a method for treating cancer in a patient. In some embodiments, the method comprises administering to the patient a compound described herein, or a pharmaceutically acceptable salt thereof, in an amount effective to treat cancer. In other embodiments, the method comprises administering to the patient a composition comprising a compound described herein in an amount effective to treat cancer.

In some embodiments, the patient receives an additional treatment, such as radiation therapy, surgery, and chemotherapy with another chemotherapeutic agent or combinations thereof. In some embodiments, the compound of the disclosure is administered concurrently with the chemotherapeutic agent or with radiation therapy or with surgery. In other embodiments, the chemotherapeutic agent or radiation therapy or surgery is administered or performed prior or subsequent to administration of a compound of the disclosure.

In some embodiments, the method for treating cancer further comprises administering to the patient an effective amount of a second therapeutic agent, e.g., a chemotherapeutic agent. Any one or a combination of the chemotherapeutic agents, such a standard of care chemotherapeutic agent(s), can be administered.

In some embodiments, the chemotherapeutic agent may be selected from the group consisting of a tubulin-forming inhibitor, a topoisomerase inhibitor, and a DNA binder.

The compound described herein and the chemotherapeutic agent may be administered simultaneously in either the same or different pharmaceutical composition or sequentially in any order. The amounts of compound described herein and the chemotherapeutic agent and the relative timings of their administration will be selected in order to achieve the desired combined effect.

In another embodiment, the present disclosure provides a method of inhibiting the growth of tumor cells that overexpress a tumor-associated antigen in a patient. In some embodiments, the method comprises administering to the patient a compound described herein conjugated to an antibody that is specific for said tumor-associated antigen, wherein the compound described herein is administered in amount effective to inhibit growth of tumor cells in the patient. In alternate embodiments, the method comprises administering to the patient a pharmaceutical composition comprising a compound described herein conjugated to an antibody that is specific for said tumor-associated antigen, wherein the compound described herein is administered in amount effective to inhibit growth of tumor cells in the patient. The method may optionally further comprises administering to the patient a chemotherapeutic agent, or a pharmaceutical composition thereof, in an amount effective to inhibit the growth of tumor cells in the patient.

In some embodiments, the compound sensitizes the tumor cells to the chemotherapeutic agent.

In some embodiments, the compound induces cell death. In other embodiments, the compound induces apoptosis.

In some embodiments, the tumor cells are associated with a cancer selected from the group consisting of breast, ovarian, stomach, endometrial, salivary gland, lung, kidney, colon, colorectal, thyroid, pancreatic, prostate, central nervous system and bladder cancer.

In some embodiments, the compound described herein is conjugated to an antibody selected from the group consisting of CD19, CD20, CD30, CD33, CD70, BCMA, Glypican-3, Liv-1 and Lewis Y.

Any compound or pharmaceutical composition described herein may be used in the methods of the present disclosure.

In some of the above methods, the compound described herein is administered to a patient in a composition comprising a pharmaceutically acceptable carrier. In some of these embodiments, the composition is administered intravenously. In certain embodiments, the compound is formulated in a unit dosage injectable form.

In preferred embodiments of each of the above methods, the patient is a human.

In an additional embodiment, the present disclosure provides the use of a compound of described herein in the manufacture of a medicament for the treatment of any of the above mentioned cancers. It will be appreciated that a compound described herein and one or more chemotherapeutic agents may be used in the manufacture of the medicament.

In additional embodiments, the present disclosure provides an article of manufacture comprising a compound described herein, a container, and a package insert or label indicating that the compound can be used to treat cancer characterized by the overexpression of at least one tumor-associated antigen.

The term "package insert" is used to refer to instructions customarily included in commercial packages of therapeutic products, that contain information about the indication(s), usage, dosage, administration, contraindications and/or warnings concerning the use of such therapeutic products.

In order that this invention be more fully understood, the following examples are set forth. These examples are for the purpose of illustration only and are not to be construed as limiting the scope of the invention in any way.

EXAMPLES

The compounds of this disclosure may be prepared by methods known to those skilled in the art, or the methods set forth below. By following the methods below, additional compounds of the disclosure can be prepared by modifying the choice of starting materials, reagents and reaction conditions as known to those skilled in the art.

General Experimental Procedures

Both N-Boc-Dolaproine and Dov-Val-Dil.TFA were synthesized as described earlier.[6,7] 2-(1'-amino-2'-ethyl)-quinoline dihydrochloride and 6-quinoline acetic acid were purchased from J&W Pharmlab LLC and Astatech, Inc respectively, and were used as received. 3-quinoline acetic acid and 7-quinoline acetic acid were purchased from Princeton Bimolecular Research, Inc. and 8-(1'-amino-2'-ethyl)-quinoline was purchased from Fisher Scientific and all used as received. 4-(1'-amino-2'-ethyl)-quinoline dihydrochloride and 5-(1'-amino-2'-ethyl)-quinoline dihydrochloride were purchased from Enamine Ltd. Other reagents and anhydrous solvents were purchased from Acros Organics (Fisher Scientific), Sigma-Aldrich Chemical Company and were used as received. For thin-layer chromatography, Analtech silica gel GHLF Uniplates were used and visualized with shortwave UV irradiation and an iodine chamber. For column chromatography, silica gel (230-400 mesh ASTM) from E. Merck (Darmstadt, Germany) was used. Melting points are uncorrected and were determined with a Fischer-Johns melting point apparatus.

Optical rotations were measured by use of a Perkin-Elmer 241 polarimeter, and the $[\alpha]_D$ values are given in $10^{-1}$ deg cm$^2$ g$^{-1}$. The $^1$H, $^{13}$C spectra were recorded on Varian Unity INOVA 400 and 500 instruments with deuterated solvents. High-resolution mass spectra were obtained with a Jeol JMS-LCmate mass spectrometer.

Example 1. Synthesis of Quinstatin 2

Scheme 1 depicts the synthesis of Quinstatin 2 (3).

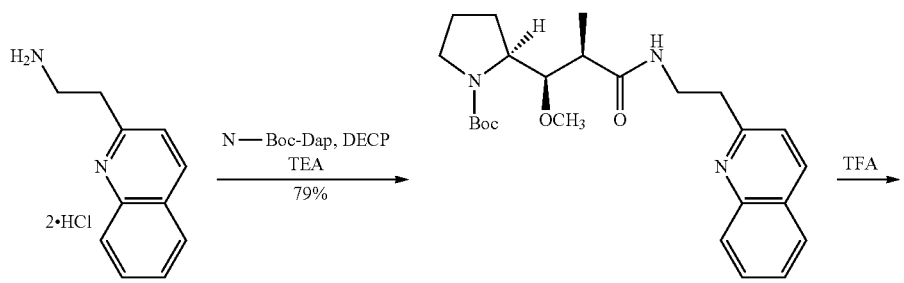

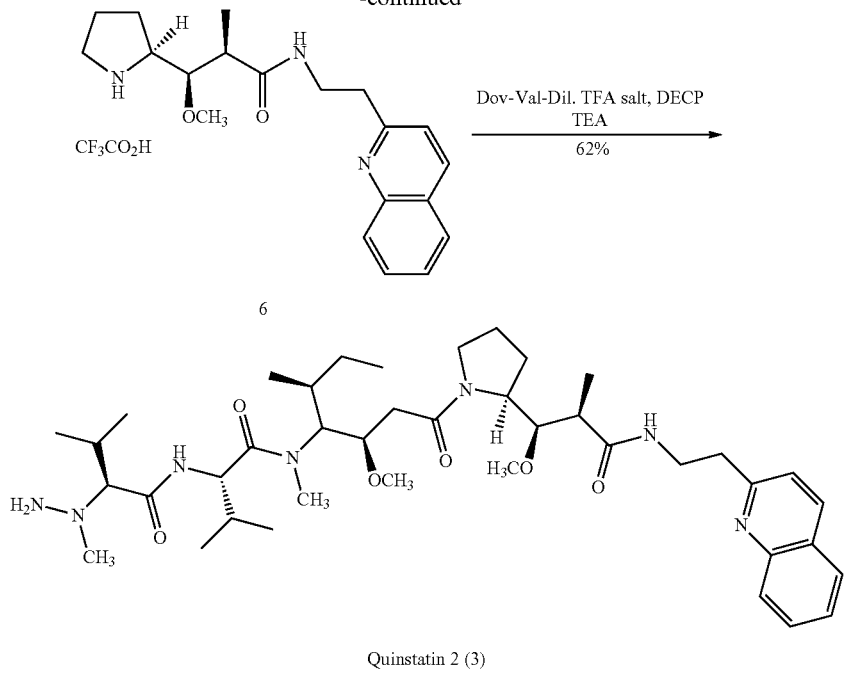

Quinstatin 2 (3)

2-(1'-Boc-Dap-amino-2'-ethyl)-quinoline (5)

To a stirred solution of Boc-Dap[6] (0.06 g, 0.21 mmol) and 2-(1'-amino-2'-ethyl)-quinoline dihydrochloride (0.08 g, 0.32 mmol) in anhydrous DCM (1 mL) at 0° C. under $N_2$ was added TEA (0.2 mL, 1.42 mmol) and diethylcyanophosphonate (DECP) (0.1 mL, 0.6 mmol). The reaction mixture was stirred at 0° C. with warming to room temperature for 6 h, and then concentrated under reduced pressure to an orange colored residue which was purified by chromatography on a silica gel column. Gradient elution with hexanes 100% to 7:2 hexanes—acetone gave the product as a yellow residue under reduced pressure. The product was further separated on a silica gel column, and eluting with 7:2 hexanes:acetone gave an off-white waxy solid, 112 mg (79%); TLC $R_f$ 0.5 (3:4 hexanes-acetone); Doubling of signals observed in the $^1H$ and $^{13}C$ NMR data indicating conformational isomers in almost 1:1 ratio due to cis-trans isomerism at the Dap bond[7]; $^1H$ NMR (CDCl$_3$, 400 MHz) δ 8.01 (1H, d, J=8 Hz), 7.95 (1H, d, J=8 Hz), 7.72 (1H, d, J=8 Hz), 7.63 (1H, t, J=8 HZ), 7.43 (1H, t, J=8 Hz), 7.23 (1H, d, J=8 Hz), 6.99, 6.85 (1H, brs, 2×1H), 3.83-3.56 (4H, m), 3.46-3.34 (1H, m), 3.28 (4H, m), 3.18-3.01 (m, 2H), 2.36-2.15 (m, 1H), 1.83-1.47 (m, 4H), 1.37, 1.41 (s, 9H, t-Bu), 1.12-1.09 (m, 3H). $^{13}C$ NMR (CDCl$_3$, 400 MHz) (two conformers were observed) 174.1, 173.6, 160.1 154.6, 154.3, 147.6, 136.5, 129.6, 128.7, 127.6, 126.8, 126.1, 121.7, 83.9, 82.3, 79.6, 79.0, 60.7, 60.5, 58.7, 46.8, 46.5, 44.2, 43.9, 38.3, 38.1, 37.5, 37.3, 28.5, 25.7, 25.3, 252, 24.4, 23.9, 14.1, 14.05. HRAPCIMS m/z 442.2707 [M+H]$^+$ (calcd for $C_{25}H_{36}N_3O_4$ 442.2706).

2-(1'-Boc-Dap-amino-2'-ethyl)-quinoline trifluoroacetate (6)

To a stirred solution of compound 5 (0.070 g, 0.16 mmol) in DCM (4 mL) at 0° C. under $N_2$ was added trifluoroacetic acid (TFA) (1 mL) and stirring was continued for 1.5 h at 0° C. The reaction was stopped and concentrated under reduced pressure to remove DCM and excess TFA to yield a yellow oil. This material was used without further purification in the next reaction.

2-(1'-Dov-Val-Dil-Dap-2'-ethyl)-quinoline (3, Quinstatin 2)

Amide 6 and Dov-Val-Dil.TFA[7] (90 mg, 0.16 mmol) were dissolved in anhydrous DCM (5 mL) and the solution was stirred under $N_2$ and cooled to 0° C. TEA (0.12 mL, 0.86 mmol) and DECP (0.035 mL, 0.21 mmol) were added, and the mixture was stirred under $N_2$ for 18 h with warming to room temperature. The reaction mixture was concentrated under reduced pressure and separated on a silica gel column. Elution with DCM:MeOH (95:5) gave the product as a colorless foam: yield 74 mg (62%); TLC $R_f$ 0.3 (CH$_2$Cl$_2$: CH$_3$OH 7%); $[α]_{22}^D$—8.2 (c 0.27, CHCl$_3$); Conformational isomers are present[3a] (~2:1) and doubling of signals were observed in both the proton and carbon NMR spectra for 3; $^1H$ NMR (CDCl$_3$, 400 MHz) major conformer δ 8.08 (1H, d, J=8.8 Hz), 8.02 (1H, d, J=8.4 Hz), 7.79 (1H, d, J=7.0 Hz), 7.70 (1H, t, J=8.0 Hz), 7.51 (1H, t, J=6.8 Hz), 7.33 (1H, d, J=9.0 Hz), 7.16 (1H, m), 6.88 (1H, m), 4.80 (1H, d, J=6.9 Hz), 4.78 (1H, d, J=6.9 Hz), 4.12-4.04 (2H, m), 3.89-3.74 (3H, m), 3.33 (3H, s), 3.27 (3H, s), 3.21 (1H, t, J=6.8 Hz), 3.17 (1H, s), 3.01 (3H, s), 2.48-2.29 (3H, m), 2.25 (6H, s), 2.13-1.84 (7H, m), 1.73 (1H, m), 1.43-1.32 (1H, m), 1.25-1.20 (m, 3H), 1.06-0.8 (21H, m); $^{13}C$ NMR (CDCl$_3$, 400 MHz) two conformers, 174.0, 173.5, 173.3, 171.6, 170.1, 169.9, 160.3, 159.9, 147.7, 147.6, 36.7, 136.3, 129.7, 129.4, 128.8, 128.7, 127.6, 1275, 126.8, 126.8, 126.2, 125.9, 121.7, 121.6, 86.0, 82.0, 78.2, 76.5, 76.4, 61.5, 60.3, 59.0, 58.1, 57.7, 53.73, 53.68, 53.5, 47.5, 46.5, 44.9, 44.0, 42.8, 38.5, 37.9, 37.8, 37.4, 33.1, 30.9, 27.6, 25.9, 25.7, 24.9, 24.7, 23.4, 20.1, 17.8, 17.7, 15.8, 15.2, 14.3, 10.7, 10.3 ppm. HRAPCIMS m/z 753.5292 [M+H]+(calcd for $C_{42}H_{69}N_6O_6$, 753.5279).

Example 2. Synthesis of Quinstatin 3

3-(1'-Hydroxyl-2'-ethyl)-quinoline

To a stirred solution containing 3-quinoline acetic acid (0.03 g, 0.16 mmol) in anhydrous tetrahydrofuran (THF) (2 mL) at 0° C. was added dropwise LiAlH$_4$ (1 M solution in THF, 0.2 mL, 0.3 mmol, 1.25 equiv.).

The reaction mixture was stirred at 0° C. for 1 h, dampened with the successive addition of water (8 μL), 15% NaOH (8 μL) and again water (24 μL), prior to being stirred for 45 min at 0-5° C. and drying (Na$_2$SO$_4$). The solution was filtered to remove the precipitated solids and the filtrate was concentrated under reduced pressure to give a yellow oil which solidified on standing to a waxy solid (15.8 mg, 57%); TLC R 0.17 (DCM-MeOH 3%); $^1$H NMR (CDCl$_3$, 400 MHz) δ 8.71 (1H, s), 8.01 (1H, d, J=7.5 Hz), 7.96 (1H, s), 7.70 (1H, d, J=8.4 Hz), 7.62 (1H, t, J=7.5 Hz), 7.48 (1H, t, J=7.5 Hz), 3.97 (2H, t, J=6.4 Hz), 3.01 (2H, t, J=6.4 Hz); 13C NMR (CDCl$_3$, 100 MHz) 151.9, 146.6, 135.5, 131.8, 128.9, 128.8, 128.0, 127.4, 126.7, 62.9, 36.5.

3-(1'-Bromo-2'-ethyl)quinoline

A stirred solution of 3-(1'-Hydroxyl-2'-ethyl)-quinoline (0.15 g, 0.86 mmol) in anhydrous benzene (20.0 mL) were gently heated to effect solution and cooled to 0° C. Phosphorous tribromide (0.2 ml, 2.4 g, 2.1 mmol, 2.4 equiv.) in benzene (1.5 mL) was added and the mixture heated to 60° C. for 45 min, then cooled to 0° C. Saturated aq. NaHCO$_3$ (6 mL) was added until neutral pH. The mixture was extracted with ethyl acetate (3×10 ml) and the combined organic extracts were washed with water, dried (Na$_2$SO$_4$) and concentrated to give a yellow residue which was separated using silica gel column chromatography (sgc) and a gradient elution of CH$_2$Cl$_2$ 100%→CH$_2$Cl$_2$—CH$_3$OH 4%, to yield the product as a yellow oil (68 mg, 34% yield); R$_f$=0.54 (CH$_2$Cl$_2$:CH$_3$OH 4%); $^1$H NMR (CDCl$_3$, 400 MHz) δ 8.79 (1H, s), 8.09 (1H, d, J=8.8 Hz), 8.00 (1H, s), 7.80 (1H, d, J=8.0 Hz) 7.63 (1H, t, J=7.8 Hz) 7.54 (1H, t, J=8 Hz), 3.66 (2H, t, J=7.8 Hz), 3.36 (2H, t, J=7.2 Hz). $^{13}$C NMR (CDCl$_3$, 400 MHz) 151.6 (×2), 135.4, 131.7, 129.5, 129.4, 128.1, 127.7, 127.1, 36.6, 32.5 PPM.

3-(1'-azido-2'-ethyl)quinoline

To a stirred solution containing 3-(1'-Bromo-2'-ethyl)quinoline (0.023 g, 0.1 mmol) in anhydrous DMF (0.5 mL) was added NaN$_3$ (15 mg, 0.23 mmol, 2.3 equiv.). The reaction mixture was heated to 90° C. for 30 min, cooled and diluted with ethyl acetate (3 mL), washed with water (3 mL), brine (3 mL), dried (MgSO$_4$), and concentrated to give the azide as a brown oil, 15.5 mg, 79% yield; R$_f$=0.50 (CH$_2$Cl$_2$: CH$_3$OH 3%); $^1$H NMR (CDCl$_3$, 400 MHz) δ 8.79 (1H, s) 8.13 (1H, d, J=8 Hz), 8.07 (1H, d, J=8 Hz), 7.67 (1H, s), 7.59 (1H, d, J=8.8 Hz), 7.41 (1H, dd, J=8, 4 Hz), 3.63 (2H, t, J=7 Hz), 3.09 (1H, t, J=7 Hz); 13C NMR (CDCl$_3$, 100 Hz) 150.2, 147.4, 137.8, 136.4, 135.7, 130.6, 129.8, 127.1, 121.3, 52.2, 35.3 PPM.

3-(1'-amine-2'-ethyl)quinoline

To a stirred solution of the preceding azide (0.015 g, 0.075 mmol) in anhydrous THF (1 mL) cooled to 0° C. under N$_2$, was added dropwise LiAlH$_4$ (1M solution in THF, 0.1 mL, 0.1 mmol, 1.3 equiv.). Stirring at 0° C. was continued for 45 min. The reaction was completed by the dropwise addition of H$_2$O (4 μL), 15% NaOH (4 μL), and H$_2$O (12 μL) successively, and stirring was continued for 30 min. The mixture was diluted with ethyl acetate (5 mL) dried (Na$_2$SO$_4$), and the product solution filtered. The filter cake was washed with ethyl acetate (5 mL), the organic layers combined, concentrated and dried under reduced pressure to give a yellow oil (11 mg, 84%); $^1$H NMR (CDCl$_3$, 400 MHz) indicated a mixture of the desired amine along with a dihydroquinoline based on the observed upfield shift of the aromatic ring signals in the proton spectrum. The material was carried forward as this mixture to coupling with Boc-Dap.

3-(1'-Boc-Dap-2'-ethyl)-quinoline

To a solution of the preceding amine mixture (0.04 g, 0.23 mmol) in anhydrous DCM (1 mL) was added a solution of Boc-Dap[6] (0.06 g, 0.22 mmol) in anhydrous DCM (1 mL) and the resulting mixture cooled to 0° C. Triethylamine (0.2 ml, 1.43 mmol) and DECP (0.12 mL, 0.8 mmol) were added and the solution stirred at 0° C. with warming to room temperature for 6 h. Concentration under reduced pressure led to a dark orange oil which was separated by sgc. Elution with a gradient 100% Hexane-1: 1-2:3 hexanes-acetone yielded a dark orange oil, 100 mg. Purification was achieved using flash sg chromatography and a gradient elution of Hexane 100%→Hexane-Acetone 1:4. The early fractions were combined to give an oil (56 mg) which on 1H NMR analysis was found to be Boc-dap starting material contaminated with DEPC reagent. The product was obtained as a foam (20 mg, 21% yield); $^1$H NMR (CDCl$_3$, 400 MHz): δ 8.77 (1H, s), 8.06 (1H, d, J=8.6 Hz), 7.98 (1H, bs), 7.74 (1H, d, J=8 Hz), 7.66 (1H, t, J=7.44 Hz), 7.52 (1H, t, J=7.44 Hz), 6.59 (1H, bs), 5.85 (1H, bs), 3.81-3.41 (4H, m), 3.34 (3H, s), 3.20-3.3.08 (2H, m), 3.06-2.99 (2H, m), 2.28 (1H, m), 1.83-1.70 (2H, m), 1.64-1.54 (2H, m), 1.50-1.38 (9H, m), 1.22-1.13 (3H, m). (+)HRAPCIMS m/z 442.2707 [M+H]$^+$ (calcd for C$_{25}$H$_{36}$N$_3$O$_4$ 442.2706).

3-(1'-Dap-amino-2'-ethyl)-quinoline Trifluoroacetate salt

To a stirred solution of amide (0.02 g, 0.04 mmol) in anhydrous DCM (1.5 mL) at 0° C. under N$_2$ was added TFA (0.3 mL, 0.2 g, 1.76 mmol, 44 equiv.). The solution was stirred for 1.5 h at 0° C., and then concentrated and dried under reduced pressure to give a residue which was used immediately in the next reaction. 3-(1'-Dov-Val-Dil-Dap-2'-ethyl)-quinoline (Quinstatin 3). To a stirred solution of the preceding TFA salt (0.015 g, 0.04 mmol) and Dov-Val-Dil TFA[7] (0.025 g, 0.04 mmol) in anhydrous DCM (3 mL) at 0° C. under N$_2$ was added TEA (0.03 mL) followed by DECP (0.011 mL) and the solution stirred at 0° C. for 3 h. The solvent was removed at room temperature under reduced pressure to give a yellow oil which was separated by chromatography on a silica gel column eluting with a gradient of DCM-MeOH 4% to DCM-MeOH 12% which gave the product in the final fractions as an oil, 30 mg, containing contaminants which were removed by extracting the product into dichloromethane and washing with water, dried (Na$_2$SO$_4$), and concentrated to an off-white glass solid (powder when scratched) 10 mg (29% yield); TLC R$_f$=0.14 (Hexane-Acetone 1:1); $^1$H NMR (CDCl$_3$, 400 MHz) δ 8.75 (1H, bs), 8.03 (1H, d, J=8 Hz), 7.98 (1H, s), 7.74 (1H, d, J=8 Hz), 7.63 (1H, t, J=8 Hz), 7.50 (1H, t, J=7.6 Hz), 6.90 (1H, bs), 4.73 (1H, t, J=8 Hz), 3.95 (1H, m), 3.84 (1H, m), 3.78 (1H, d, J=9 Hz), 3.75-3.47 (2H, m), 3.38-3.18 (2H, m), 3.38

(3H, s), 3.21 (3H, s), 3.14-3.0 (3H, m), 2.97 (3H, s), 2.64-2.47 (6H, bs), 2.28 (2H, m), 2.17-1.79 (3H, m), 1.64 (2H, m), 1.35-1.11 (6H, m), 1.07-0.74 (21H, m); (+)HRAP-CIMS m/z 753.5282 [M+H]+ (calcd for $C_{42}H_{69}N_6O_6$, 753.5279).

Example 3. Synthesis of Quinstatin 6

Scheme 2 depicts the Synthesis of Quinstatin 6 (4).

product mixture was stirred for 45 min at 0° C. then dried ($Na_2SO_4$). The solids were removed by filtration and the organic filtrate was concentrated and dried further under reduced pressure to alcohol 7, a yellow oil, 72 mg, 86% yield. $^1$H NMR ($CDCl_3$, 400 MHz) δ 8.82 (dd, 1H, J=1.6, 4.3 Hz), 8.08 (d, 1H, J=8 Hz), 8.00 (d, 1H, J=8 Hz), 7.64 (bs, 1H), 7.58 (dd, 1H, J=8, 1.8 Hz), 7.36 (dd, 1H, J=8.8, 4.4 Hz), 3.98 (t, 2H, J=6.5 Hz), 3.06 (t, 1H, J=6.5 Hz). $^{13}$C-NMR

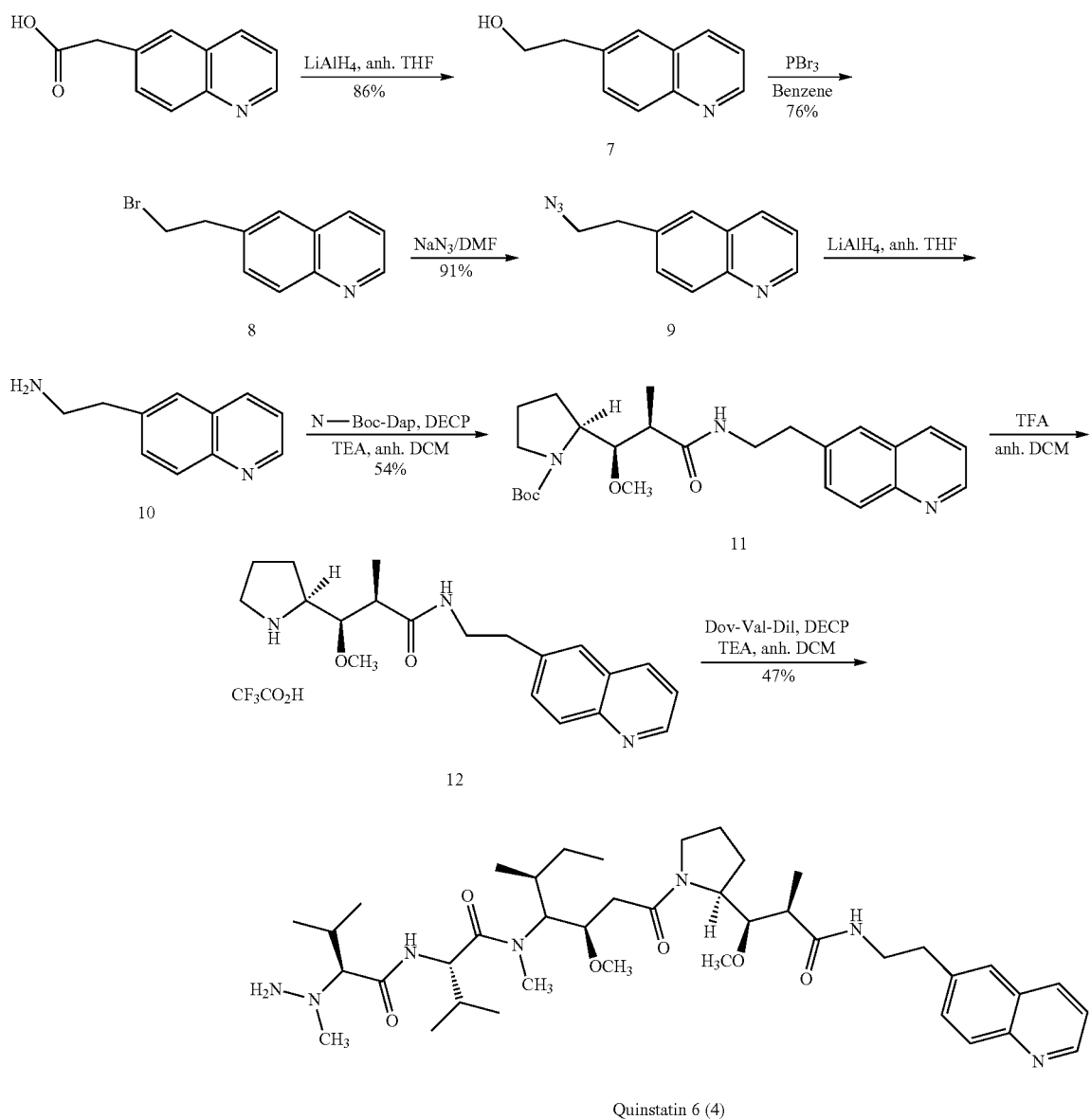

Quinstatin 6 (4)

2-(Quinolin-6-yl)ethan-1-ol (7)

2-(Quinolin-6-yl)Acetic acid (0.09 g, 0.48 mmol) in anhydrous THF (9 mL) was stirred at 0° C. (ice bath). A 1M solution of $LiAlH_4$ in THF (0.6 mL, 0.6 mmol, 1.25 equiv.) was added dropwise.[8] The reaction mixture was then stirred for 1 h at 0° C. and terminated with the addition of $H_2O$ (0.02 mL), 15% NaOH (0.02 mL) and $H_2O$ (0.06 mL). The ($CDCl_3$, 100 MHz) 150.3, 147.4, 137.5, 135.9, 131.3, 129.7, 127.4, 125.7, 121.4, 63.4, 39.4 PPM.

6-(2-Bromoethyl)quinoline (8):[9]

To a stirred solution of alcohol 7 (0.12 g, 0.67 mmol) in anhydrous benzene (2.0 mL) at 0° C. was added a solution of phosphorous tribromide (0.9 ml, 5.6 mmol, 8 equiv.) in benzene (1.0 mL). The mixture was heated to 60° C. for 45 min, then cooled to room temperature and sat. aq. NaHCO$_3$ (100 mL) was added until a neutral pH was achieved. The mixture was then extracted with ethyl acetate (3×20 ml) and the combined organic extracts were washed with water, dried (Na$_2$SO$_4$) and concentrated to give the bromide as a yellow oil, 0.12 mg, 76% yield. $^1$H NMR (CDCl$_3$, 400 MHz) δ 8.90 (s, 1H), 8.13 (d, 1H, J=8.4 Hz), 8.08 (d, 1H, J=8.4 Hz), 7.66 (s, 1H), 7.58 (d, 1H, J=8.4 Hz), 7.39 (m, 1H), 3.65 (t, 2H, J=7.2 Hz), 3.34 (t, 1H, J=7.2 Hz). $^{13}$C NMR (CDCl$_3$, 400 MHz) 150.2, 147.4, 137.2, 135.7×2, 130.5, 129.8, 127.1, 121.3, 39.1, 32.5 PPM.

6-(2-Azidoethyl)quinoline (9)

To a stirred solution of bromide 8 (0.12 g, 0.5 mmol) in anhydrous DMF (3 mL) was added NaN$_3$ (120 mg, 1.84 mmol, 3.7 equiv.) and the reaction mixture heated to 90° C. for 30 min. and after cooling the reaction mixture, it was diluted with ethyl acetate (30 mL), washed with water (30 mL), followed by brine (30 mL), dried (MgSO$_4$) and concentrated to give the azide as a brown oil, 91 mg, 91% yield. $^1$H NMR (CDCl$_3$, 400 MHz) δ 8.91 (s, 1H), 8.13 (d, 1H, 8 Hz), 8.07 (d, 1H, J=8 Hz), 7.67 (s, 1H), 7.59 (d, 1H, J=8.8 Hz), 7.41 (dd, 1H, J=8, 4 Hz), 3.63 (t, 2H, J=7 Hz), 3.09 (t, 1H, J=7 Hz). $^{13}$C-NMR (CDCl$_3$, 100 Hz) 150.2, 147.4, 137.8, 136.4, 135.7, 130.6, 129.8, 127.1, 121.3, 52.2, 35.3 PPM.

2-(Quinolin-6-yl)ethan-1-amine (10)

To a stirred solution of azide 9 (0.089 g, 0.45 mmol) in anhydrous THF (3 mL) cooled to 0° C. under N$_2$ was added dropwise a 1M solution of LiAlH$_4$ in THF (0.75 mL, 0.75 mmol, 1.65 equiv.). Stirring at 0° C. was continued for 45 min. The reaction was completed by the dropwise addition of H$_2$O (30 μL), 15% NaOH (30 μL), and H$_2$O (90 μL) successively and stirring was continued for 20 min. The mixture was diluted with ethyl acetate (10 mL) dried (Na$_2$SO$_4$), and the solution filtered. The filter cake was washed with ethyl acetate (5 mL), the organic layers combined, concentrated and dried under reduced pressure to give amine 8 as a yellow oil (quantitative yield). $^1$H NMR (CDCl$_3$, 500 MHz) 8.88 (m, 1H), 8.11 (d, 1H, J=8.3 Hz), 8.06 (d, 1H, J=8.7 Hz), 7.63 (s, 1H), 7.59 (d, 1H, J=8.5 Hz), 7.39 (dd, 1H, J=8, 4 Hz), 3.09 (t, 2H, J=7 Hz), 2.95 (t, 2H, J=7 Hz), 1.81 (bs, 2H) PPM. $^{13}$C-NMR (CDCl$_3$, 120 Hz) 149.9, 147.3, 137.6, 135.6, 131.0, 129.6, 126.9, 121.2, 43.2, 39.9 PPM.

Boc-Dap-2(quinolin-6-yl)ethylamine) (11):$^3$c

To a solution of the amine 10 (0.083 g, 0.5 mmol) in anhydrous DCM (3 mL) was added a solution of Boc-Dap (0.153 g, 0.5 mmol) in anhydrous DCM (1 mL) and the resulting mixture cooled to 0° C. Triethylamine (0.3 ml, 2.1 mmol) and DECP (0.2 mL, 1.2 mmol) were added and the solution stirred at 0° C. for 2 h, then concentrated under reduced pressure to a dark orange oil which was separated on a silica gel column. Elution with a gradient 3:2-1:1-*2:3 of hexanes:acetone gave the desired amide as a colorless oil: 111 mg, 54% yield; TLC R$_f$0.5 (hexanes:acetone 1:1); H NMR (CDCl$_3$, 400 MHz) δ 8.88 (s, 1H), 8.10-8.04 (m, 2H), 7.65-7.58 (m, 2H), 7.39 (m, 1H), 6.42, 5.73 (bs, NH), 3.85-3.42 (m, 4H), 3.35 (s, 3H), 3.37-3.27 (m, 1H), 3.19-3.10 (m, 1H), 3.09-3.01 (m, 2H), 2.40-2.21 (m, 1H), 1.84- 1.71 (m, 3H), 1.53-1.42 (m, 10H), 1.19 (nm, 3H) ppm. HRMS APCI (+) m/z 442.2695 (M+H)$^+$ (100), (calcd. for C$_{25}$H$_{36}$N$_3$O$_4$, 442.2706).

Dap-2-(quinolin-6-yl)ethylamine Trifluoroacetate (12)

To a stirred solution of amine 11 (0.1 g, 0.23 mmol) in anhydrous DCM at 0° C. under N$_2$ was added TFA (1 mL). The solution was stirred for 2 h at 0° C., and then concentrated under reduced pressure to give a residue which was taken up in toluene and reconcentrated (×2). The oily TFA salt was dried under reduced pressure to a consistent weight (2 h, 96 mg) and used immediately in the next reaction.

Dov-Val-Dil-Dap-2-(quinolin-6-yl)ethylamine (Quinstatin 6) (4)

To a stirred solution of TFA salt 13 (0.96 mg) and Dov-Val-Dil TFA (0.114 g, 0.21 mmol) in anhydrous. DCM (3 mL) at 0° C. under N$_2$ was added TEA (0.12 mL, 0.86 mmol) followed by DECP (0.035 mL, 0.2 mmol) and the solution stirred at 0° C. for 2 h. The solvent was removed at room temperature under reduced pressure to give a yellow oil which was separated by chromatography on a short silica gel column (7×3 cm) and eluting slowly with hexanes: acetone 1:1 to give Quinstatin 6 as a yellow foamy solid, 78 mg (47%); TLC R$_f$0.23 (DCM:MeOH 6%); [α]$_{22}^D$—6.5 (c 0.34, CHCl$_3$) H NMR (CDCl$_3$, 400 MHz) 8.88 (dd, 1H, J=4.4, 1.6 Hz), 8.10 (d, 1H, J=8 Hz), 8.03 (d, 1H, J=8.8 Hz), 7.66 (s, 1H), 7.61 (dd, 1H, J=8, 2 Hz), 7.39 (dd, 1H, J=8.0, 4.0 Hz), 6.88 (d, 1H, J=10 Hz), 6.72 (broad t, 1H, J=4.4 Hz), 4.79 (dd, 1H, J=10, 6.8 Hz), 4.09-4.03 (m, 1H), 3.98 (m, 1H), 3.82 (dd, 1H, J=8.8 Hz, 1.6 Hz), 3.71 (m, 1H), 3.59 (m, 1H), 3.43-3.35 (m, 2H), 3.33 (s, 3H), 3.28 (s, 3H), 3.07 (t, 2H, J=8 Hz), 3.03 (s, 3H), 2.49-2.43 (m, 1H), 2.40-2.31 (m, 2H), 2.28-2.24 (m, 7H), 2.14-1.84 (m, 5H), 1.66 (m, 2H), 1.39-1.26 (m, 2H), 1.24-1.14 (m, 4H), 1.06-0.92 (m, 15H), 0.85-0.82 (m, 4H) ppm. $^{13}$C-NMR (CDCl$_3$, 400 MHz) 174.5, 172.0, 170.7, 170.3, 150.2, 147.6, 138.1, 135.9, 131.4, 129.7, 128.6, 127.3, 121.5, 81.9, 78.8, 76.7, 60.9, 59.7, 58.2, 54.1, 47.9, 44.8, 43.1, 40.7, 37.6, 35.6, 33.3, 31.3, 27.9, 26.0, 25.1, 20.1, 19.8, 18.4, 18.1, 16.1, 15.3, 10.9 ppm. HRMS (APCI$^+$) m/z 753.5279 [M+H]$^+$ (calcd for C$_{42}$H$_{69}$N$_6$O$_6$, 753.5279).

Example 4. Quinstatin7

The general experimental procedure summarized above for the synthesis of the 1'-ethylamine intermediate from the corresponding 3 and 6-quinoline acetic acids was employed for preparation of the amine intermediate required for the synthesis of Quinstatin 7.

7-(1'-hydroxyl-2'-ethyl)-quinoline

Yellow oil which solidified on standing to a waxy solid, yield 86%; TLC R$_f$ 0.25 (CH$_2$Cl$_2$—CH$_3$OH 3%); $^1$H NMR (CDCl$_3$, 400 MHz) δ 8.81 (1H, dd, J=4.6, 1.7 Hz), 8.09 (1H, d, J=8.5 Hz), 7.93 (1H, s), 7.73 (1H, d, J=8.8 Hz), 7.42 (1H, dd, J=8.8, 0.16 Hz), 7.32 (1H, dd, J=8.5, 4.6 Hz), 3.99 (2H, t, J=6.0 Hz), 3.07 (2H, t, J=6.0 Hz); $^{13}$C NMR (CDCl$_3$, 100 MHz) 150.3, 140.7, 135.9 (×2C), 128.4, 127.8, 126.9, 120.6, 63.2, 39.4.

7-(1'-Bromo-2'-ethyl)-quinoline

Colorless oil (66% yield); TLC R$_f$=0.6 DCM-MeOH 3%; $^1$H NMR (CDCl$_3$ 400 MHz) δ 8.89 (1H, dd, J=4.0, 1.2 Hz), 8.81 (1H, d, J=8.7 Hz), 7.98 (1H, s), 7.79 (1H, d, J=8.7 Hz), 7.41 (2H, m), 3.65 (2H, t, J=7.9 Hz), 3.36 (2H, t, J=7.6 Hz). 13C NMR (CDCl$_3$, 400 MHz) 149.9, 147.3, 141.1, 136.8, 128.1, 128.06, 127.8, 127.2, 120.9, 39.2, 32.2 PPM.

7-(1'-azido-2'-ethyl)-quinoline

Brown oil, quantitative yield; $^1$H NMR (CDCl$_3$, 400 MHz) 8.88 (1H, dd, J=4.0, 1.6 Hz), 8.11 (1H, d, J=8 Hz), 7.93 (1H, s), 7.76 (1H, d, J=8 Hz), 7.40 (1H, dd, J=8.8, 2 Hz), 7.35 (1H, dd, J=8, 4 Hz), 3.61 (2H, t, J=7.4 Hz), 3.09 (2H, t, J=7.1 Hz); 13C NMR (CDCl$_3$, 100 MHz) 150.9, 148.5, 139.9, 136.0, 128.9, 128.3, 128.0, 127.3, 121.1, 52.3, 35.7 PPM. 7-(1'-amino-2'-ethyl)-quinoline. Yellow residue, (91% yield); $^1$H NMR (CDCl$_3$, 400 MHz) δ 8.86 (1H, dd, J=4.4, 1.8 Hz), 8.11 (1H, dd, J=8, 1.2 Hz), 7.9 (1H, s), 7.74 (1H, d, J=8 Hz), 7.39 (1H, dd, J=8, 1.5 Hz), 7.34 (1H, dd, J=8, 4.4 Hz), 3.08 (2H, t, J=6.8 Hz), 2.96 (2H, t, J=6.8 Hz), 1.63 (bs, NH2).

7-(1'-Boc-Dap-amino-2'-ethyl)-quinoline

To a solution of the preceding amine (0.06 g, 0.35 mmol) in anhydrous DCM was added a solution of Boc-Dap$^6$ (0.1 g, 0.35 mmol) in anhydrous DCM (1 mL) and the resulting mixture cooled 0° C. Triethylamine (0.2 mL, 1.43 mmol, 4 equiv.) and DEPC (0.185 mL, 0.199 g, 1.22 mmol, 3.5 equiv.) were added. The mixture was stirred at 0° C. for 8 h, then overnight at room temperature for 24 h. The reaction mixture was next concentrated to a dark brown solid, and extracted with water, dried (Na$_2$SO$_4$) and concentrated. Purification on sg flash using DCM-MeOH 5% gave the product as a yellow oil, 65 mg (43% yield based on Boc-Dap); TLC R$_f$0.4 (DCM-MeOH 5%); $^1$H NMR (CDCl$_3$, 400 MHz) δ 8.82 (1H, bs), 8.08 (1H, bd, J=9 Hz), 7.87 (1H, s), 7.71 (1H, d, J=8 Hz), 7.39 (1H, m), 7.31 (1H, m), 6.51, 5.99 (1H, bs, NH), 3.77 (1H, m), 3.70 (1H, m), 3.66-3.52 (3H, m), 3.43-3.35 (1H, m), 3.29 (3H, s) 3.16-2.96 (2H, m), 2.33-2.15 (1H, m), 1.84-1.64 (2H, m), 1.63-1.51 (2H, m), 1.43, 1.39 (9H, s), 1.16-1.08 (3H, m); (+)HRAPCIMS m/z 442.2696 [M+H]$^+$ (calcd for C$_{25}$H$_{36}$N$_3$O$_4$, 442.2706).

7-(1'-Boc-Dap-amino-2'-ethyl)-quinoline Trifluoroacetate salt

A solution of the preceding ethylamide (0.06 g, 0.136 mmol) in dry DCM was stirred and cooled to 0° C. under N$_2$. TFA (0.15 mL) was added and the solution stirred at 0° C. for 3 h. The solvent was removed under reduced pressure using toluene as an azeotrope, to yield a residue which was further dried under high vacuum for 16 h. The salt was used as is in the next step.

7-(1'-Dov-Val-Dil-Dap-2'-ethyl)-quinoline (Quinstatin 7)

The preceding TFA salt (0.06 g) and Dov-Val-Dil-TFA$^7$ (0.078 g, 0.143 mmol, 1 equiv.) were taken up in anhydrous DCM and stirred at 0° C. TEA (0.1 mL, 0.72 mmol, 5 equiv.) and DEPC (0.022 mL, 1.43 mmol) were added in succession and the solution was stirred under argon for 4 h at 0° C. The solvent was removed under reduced pressure and the residue chromatographed using flash sg, eluting with DCM-MeOH 5%; Column size: 20 cm×2 cm; 25 g silica gel. The product was obtained as a light yellow powder, 65 mg (61% yield based on the TFA salt precursor); TLC R$_f$=0.27 (DCM-MeOH 5%). [α]$_{23}^D$—4.5 (c 0.2, CH$_3$OH); $^1$H (CDCl$_3$, 400 MHz) δ 8.82 (1H, bs), 8.07 (1H, d, J=8 Hz), 7.85 (1H, s), 7.71 (1H, d, J=8.8 Hz), 7.41 (1H, d, J=8.3 Hz), 7.31 (1H, dd, J=8, 4.7 Hz), 6.88 (1H, d, J=8.64 Hz), 6.71 (1H, m), 4.73 (1H, dd, J=9.6, 6.8 Hz), 4.02 (1H, m), 3.95 (1H, m), 3.78 (1H, dd, J=8.7, 1.6 Hz), 3.71-3.48 (3H, m), 3.33-3.28 (2H, m), 3.27 (3H, s), 3.22 (3H, s), 3.02 (2H, t, J=7.6 Hz), 2.97 (3H, bs), 2.40 (1H, d, J=7.1 Hz), 2.34-2.26 (2H, m), 2.20 (6H, s), 2.09-1.71 (5H, m), 1.62 (3H, m), 1.30 (1H, m), 1.16 (3H, d, J=7.2 Hz), 0.99-0.84 (16H, m), 0.76 (3H, t, J=7.9 Hz); $^{13}$C-NMR (CDCl$_3$, 100 MHz) 174.2, 171.7, 170.3, 170.0, 150.3, 148.3, 141.0, 135.7, 128.7, 128.0, 127.8, 126.8, 120.6, 81.7, 78.3, 76.4, 61.8, 60.5, 59.3, 58.2, 57.9, 53.7, 53.4, 47.6, 46.7, 44.4, 42.8, 42.7, 40.2, 37.4, 35.7, 33.0, 30.9, 27.6, 25.7, 24.8, 20.1, 17.7 (×2), 15.8, 14.8, 10.7; (+)HRAPCIMS m/z 753.5292 [M+H]$^+$ (calcd for C$_{42}$H$_{69}$N$_6$O$_6$, 753.5279).

Example 5. Quinstatin 8

8-(1'-Boc-Dap-2'-ethyl)-quinoline 8-(1'-amino-2'-ethyl)-quinoline (0.1 mL, 0.7 mmol) was added to a solution of Boc-Dap$^6$ (0.2 g, 0.7 mmol) in anhydrous DCM (3 mL) and the reaction mixture was stirred at 0° C. Next, TEA (0.4 mL, 2.8 mmol, 4 equiv.) and DEPC (0.3 mL, 0.2 g, 2.0 mmol, 3 equiv.) were added. The reaction mixture was stirred at 0° C. for 6 h, and overnight at room temperature for 16 h, then concentrated to a dark brown solid which was separated by sg flash chromatography using DCM-MeOH 5%; Column size (33 cm×2 cm). Fractions were combined according to TLC data. The product was obtained as a brown oil (quantitative); $^1$H (400 MHz, CDCl$_3$) δ 8.83 (1H, dd, J=4.3, 1.7 Hz), 8.08 (1H, m), 7.63 (1H, m), 7.52 (1H, d, J=6.8 Hz), 7.39 (1H, t, J=7.6 Hz), 7.33 (1H, m), 6.90 (1H, m), 3.70 (1H, m), 3.57 (3H, m), 3.46-3.32 (3H, m), 3.24 (3H, s, OCH$_3$), 3.07 (1H, m), 2.21-1.99 (1H, m), 1.66 (2H, m), 1.53-1.22 (11H, m), 1.14 (1H, m), 1.02 (2H, m); HRMS (APCI$^+$) 442.2703 (M+H)$^+$ calcd. for C$_{25}$H$_{36}$N$_3$O$_4$, 442.2706, 8-(1'-Dap-amino-2'-ethyl)-quinoline Trifluoroacetate salt A solution of the preceding amide (0.3 g, 0.68 mmol) in dry DCM (10 mL) was stirred at 0° C. under N$_2$. TFA (1.0 mL, 1.49 g, 13 mmol, 19 equiv.) was added and the reaction mixture stirred at 0° C. for 3 h and monitored by TLC, DCM-MeOH 5%. The solvent was removed under reduced pressure and using toluene as an azeotrope, then dried using high vacuum for 16 h to yield a brown oil used without further purification in the next step.

8-(1'-Dov-Val-Dil-Dap-2'-ethyl)-quinoline (Quinstatin 8)

The preceding TFA salt (0.3 g, 0.66 mmol) was dissolved in dry DCM (10 mL) and stirred at 0° C. Dov-Val-Dil-TFA$^7$ (0.37 g, 0.66 mmol, 1 equiv.) was added followed by TEA (0.5 mL, 3.6 mmol, 5 equiv.) and DEPC (0.11 mL, 7.15 mmol, 11 equiv.). The reaction mixture was stirred under N$_2$ for 4 h at 0° C. Solvent was removed under reduced pressure and the residue was dried under high vacuum. Chromatographic separation was achieved using flash sg, eluting with DCM-MeOH 5%; Column size: 20 cm×4 cm; to give the desired product as a light yellow powder 320 mg; TLC R$_f$=0.4 (DCM-MeOH 5%); [α]$_{23}^D$—12.2 (c 0.5, CH$_3$OH);

$^1$H (CDCl$_3$, 400 MHz), Doubling of signals in the proton and carbon spectra indicating the presence of two isomers, a pattern observed in dolastatin 10 and discovered to be due to conformational isomers arising from cis-trans isomerism at the Dil-Dap bond,[3b] δ 8.89 (1H, m), 8.16, 8.12 (1H, d, J=8 Hz), 7.70, 7.66 (1H, d, J=8 Hz), 7.57 (1H, d, J=6.8 Hz), 7.48, 7.44 (1H, d, J=8 Hz), 7.46-7.36 (1H, m), 6.96 (1H, bt, J=4.4 Hz), 6.86 (1H, d, J=8.8 Hz), 4.85, 4.74 (1H, dd, J=6.4, 9.6 Hz), 4.0 (1H, m), 3.80 (1H, dd, J=7.6, 2.9 Hz), 3.72-3.56 (3H, m), 3.53-3.35 (4H, m), 3.30 (3H, s, OCH$_3$), 3.27 (3H, s, OCH$_3$), 3.26, 3.25 (3H, s), 3.08 (1H, s), 2.96 (2H, bs), 2.50-2.32 (2H, m), 2.23-2.20 (6H, bs), 2.08-1.77 (5H, m), 1.69-1.51 (3H, m), 1.31 (1H, m), 1.10 (2H, d, J=7 Hz), 1.04 (1H, m), 1.0-0.83 (15H, m), 0.77 (3H, t, J=7.6 Hz); $^{13}$C-NMR (CDCl$_3$, 100 MHz) 173.9, 171.6, 170.3, 170.0, 149.4, 147.2, 138.4, 136.9, 136.6, 130.4, 130.1, 128.5, 128.4, 127.0, 126.8, 126.7, 126.5, 121.1, 120.9, 86.1, 82.1, 76.4, 61.6, 60.3, 59.0, 58.9, 58.0, 57.9, 53.7, 47.5, 46.4, 44.1, 42.9, 41.7, 41.1, 37.5, 35.7, 33.1, 30.9, 30.86, 30.7, 27.6, 25.7, 25.6, 25.0, 24.7, 23.4, 20.2, 19.8, 17.8, 17.7, 15.2, 14.1, 10.8, 10.2; (+)HRAPCIMS m/z 753.5285 (M+H)$^+$ (calcd for C$_{42}$H$_{69}$N$_6$O$_6$, 753.5279).

Example 6. Inhibition of Human Cancer Cell Growth

Cancer Cell Line Procedures.

Inhibition of human cancer cell growth was assessed using the National Cancer Institute's standard sulforhodamine B assay as previously described.[10] In summary, cells in a 5% fetal bovine serum/RPMI1640 medium were inoculated in 96-well plates and incubated for 24 hrs. Next, serial dilutions of the compounds were added. After 48 h, the plates were fixed with trichloroacetic acid, stained with sulforhodamine B, and read with an automated microplate reader. A growth inhibition of 50% (GI$_{50}$ or the drug concentration causing a 50% reduction in the net protein increase) was calculated from optical density data with Immunosoft® software.

Table 1 summarizes a series of cancer cell line growth inhibition experiments performed in parallel with very revealing and important results. Very noteworthy is the usual cancer biology equivalence of auristatin E and desmethyl-auristatin E as well as the ten to one hundred times increase in inhibition provided by Quinstatin 2 as compared to auristatin AQ.[3a] In one of these experiments Quinstatin 8 delivered inhibitions at the dolastatin 10 level, but not consistently.

REFERENCES

The following references are hereby incorporated by reference in their entireties:

(1) (a) For Antineoplastic Agents Part 602 refer to: Pettit, G. R.; Xu, J-P.; Chapuis, J-C.; Melody, N.; *J Nat. Prod*, in press. (b) Pettit G. R.; Kamano, Y.; Hearld, C. L., Tuinman, A. A.; Boettner, F. E.; Kizu, H.; Schmidt, J. M.; Baczynsyi, L.; Tomer, K. B.; Botems, R. J. *J. Am. Chem. Soc.*, 1987, 109, 6883-6885. (c) Pettit G. R.; Kamano, Y.; Dufresne, C.; Cerny, R. L.; Hearld, C. L., Schmidt, J. M. *J. Org. Chem.*, 1989, 54, 6005-6006. (d) Pettit G. R.; Smith, T.; Arce, P. M.; Flahive, E. J; Anderson, C. R.; Chapuis, J-C.; Xu, J-P.; Groy, T. L.; Belcher, P. E.; Macdonald, C. B. *J. Nat. Prod*, 2015, 78, 476-485. (1e) Pettit, G. R.; In *Progress in the Chemistry of Organic Natural Products 70: The Dolastatins*; Herz, W.; Kirby, G. W.; Moore, R. E.; Steglich, W.; Tamm, Ch.; Eds.; Springer-Verlag, 1997.

(2) (a) Pettit, G. R. In *International Oncology Updates: Marine anticancer compounds in the era of targeted therapies*; Chabner, B.; Cortés-Funes, H., Eds.; Permanyer Publications: Barcelona, 2009, 19-49. (b) Pettit, G. R.; In *ACS Symposium Series 796*: Anticancer Agents: Frontiers in Cancer Chemotherapy; Ojima, I.; Vite, G. D.; Altmann, K. H., Eds.; American Chemical Society, Washington, D C, 2001. (c) Bai, R.; Edler, M. C.; Bonate, P. L.; Copeland, T. D.; Pettit, G. R.; Luduen̄ a, R. F.; Hamel, E. *Mol Pharmacol*, 2009, 75, 218-226.

(3) (a) Pettit, G. R.; Hogan, F.; Toms, S. *J Nat. Prod.* 2011, 74, 962-968. (b) Pettit G. R., Srirangam, J. K., Barkoczy, J.; Williams, M. D.; Boyd, M. R.; Hamel, E.; Pettit, R. K.;

TABLE 1

Human Cancer Cell Lines (GI$_{50}$ µg/mL [nM]), Growth Inhibition Results from Comparison Experiments.

| Compound | Cell line[a] | | | | | |
|---|---|---|---|---|---|---|
| | BXPC-3 | MCF-7 | SF-268 | NCI-H460 | KM20L2 | DU-145 |
| Dolastatin 10[1a] (1) | 0.000040 [0.051] | 0.0000042 [0.005] | 0.0000043 [0.006] | 0.00018 [0.229] | 0.0000080 [0.010] | 0.0000052 [0.007] |
| Quinstatin 2 (3) | 0.0093 [12.35] | 0.00031 [0.412] | 0.00023 [0.306] | 0.0051 [6.777] | 0.00033 [0.438] | 0.00031 [0.412] |
| Quinstatin 3 | 0.021 [27.9] | 0.00023 [0.31] | 0.00029 [0.38] | 0.031 [41.2] | 0.00040 [0.53] | 0.00020 [0.26] |
| Quinstatin 6 (4) | 0.0020 [2.657] | 0.00040 [0.532] | 0.00030 [0.399] | 0.0043 [5.714] | 0.00039 [0.518] | 0.00030 [0.399] |
| Quinstatin 7 | 0.0031 [4.12] | 0.000030 [0.039] | 0.000024 [0.032] | 0.011 [14.61] | 0.000041 [0.054] | 0.000030 [0.040] |
| Quinstatin 8 | 0.00050 [0.425] | 0.000040 [0.053] | 0.000023 [0.030] | 0.00090 [1.19] | 0.000040 [0.053] | 0.000040 [0.053] |
| Auristatin E[3a](2a) | >0.001 [>1.37] | 0.00017 [0.232] | 0.00036 [0.492] | 0.00039 [0.533] | 0.00036 [0.492] | 0.00031 [0.424] |
| Desmethylauristatin E[5](2b) | >0.001 [>1.39] | 0.00029 [0.404] | 0.00031 [0.432] | 0.00049 [0.683] | 0.00043 [0.599] | 0.00030 [0.418] |

[a]Cancer cell lines in order: pancreas (BXPC-3); breast (MCF-7); CNS (SF-268); lung (NCI-H460); colon (KM20L2); prostate (DU-145).

Hogan, F., Bai, R.; Chapuis, J-C.; McAllister, S.; Schmidt, J. M. *Anti-Cancer Drug Design,* 1998, 13, 243-277. (c) Pettit, G. R.; Srirangam, J. K.; Barkoczy, J.; Williams, M. D.; Durkin, K. P. M.; Boyd, M. R.; Bai, R.; Hamel, E.; Schmidt, J. M.; Chapuis, J-C. *Anti-Cancer Drug Design,* 1995, 10, 529-544.

(4) (a) Maderna, A.; Leverett, C. *Mol. Pharmaceutics,* 2015, 12, 1798-1812. (b) Sievers, E. L.; Senter, P. D. *Annu. Rev. Med.* 2013, 64, 15-29. (c) Okeley, N. M., Stephen C. Alley, S. C., Senter, P. D. *Hematol. Oncol. Clin. N. Am.* 2014, 28, 13-25. (d) Younes, A.; Gopal, A. K.; Smith, S. E.; Ansell, S. M.; Rosenblatt, J. D.; Savage, K. J.; Ramchandren, R.; Bartlett, N. L.; Cheson, B. D.; de Vos, S.; Forero-Torres, A.; Moskowitz, C. H.; Connors, J. M.; Engert, A.; Larsen, E. K.; Kennedy, D. A.; Sievers, E. L.; Chen, R. *J. Clin. Onco,* 2012, 30, 2183-3018. (e) Kung Suterland, M. S.; Sanderson, R. J.; Gordon, K. A.; Andreyka, J.; Cerveny, C. G.; Yu, C.; Lewis, T. S.; Meyer, D. L.; Zabinski, R. F.; Doronina, S. O.; Senter, P. D., Law, C-L.; Wahl, A. F. *J. Biol. Chem,* 2006, 281, 10540-10547.

(5) Doronina, S. O.; Toki, B. E.; Torgov, M. Y.; Mendelsohn, B. A.; Cerveny, C. G.; Chace, D. F.; DeBlanc, R. L.; Gearing, R. P.; Bovee, T. D.; Siegall, C. B., Francisco, J. A.; Wahl, A. F.; Meyer, D. L.; Senter, P. D.; *Nat. Biotech.,* 2003, 21(7), 778-784.

(6) Pettit, G. R.; Singh, S. B.; Herald, D. L.; Lloyd-Williams, P.; Kantoci, D.; Burkett, D. D.; Barkoczy, J.; Hogan, F.; Wardlaw, T. R. *J. Org. Chem.* 1994, 59, 6287-6295. (b) Pettit, G. R.; Grealish, M. P. *J. Org. Chem.* 2001, 66, 8640-8642. (c) Mordant, C.; Reymond, S.; Tone, H.; Lavergne, D.; Touati, R.; Ben Hassine, B.; Ratovelomanana-Vidal, V; Genet, J-P. *Tetrahedron* 2007, 63, 6115-6123.

(7) Pettit, G. R.; Srirangam, J. K.; Singh, S. B.; Williams, M. D.; Herald, D. L.; Barkoczy, J.; Kantoci, D.; Hogan, F. *J. Chem. Soc., Perkin Trans.* 1, 1996, 859-863.

(8) Micovic, V. M.; Mihailovic, M. L. *J. Org. Chem.,* 1953, 18, 1190-1200 b. Newman, M. S., Fukunaga, T. *J. Am. Chem. Soc.,* 1960, 82, 693-696.

(9) (a) Albrecht, B. K.; Bellon, S.; Booker, S.; Cheng, A. C.; D'Amico, D.; D'Angelo, N.' Kim, T-S.; Liu, L.; Norman, M. H.; Siegmun, A. C.; Stec, M.; Xi, N.; Yang, K.; *Amgen Inc., USA,* 2008, WO 2008103277 (b) Baba, A.; Kawamura, N., Makino, H.; Ohta, Y.; Taketomi, S.; Sohda, T. *J. Med. Chem.,* 1996, 39, 5176-5182.

(10) Monks, A.; Scudiero, D.; Skehan, P.; Shoemaker, R.; Paull, K.; Vistica, D.; Hose, C.; Langley, J.; Cronise, P.; Viagro-Wolff, A.; Gray-Goodrich, M.; Campbell, H.; Mayo, J.; Boyd, M. *J. Natl. Cancer Inst.* 1991, 83, 757-766.

U.S. Pat. Nos. 5,654,399 and 5,767,237;

United States Patent Application Publication 2013/0190248; and

PCT Publication WO 0/41789.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present invention is not limited to the specific embodiments illustrated herein, but is limited only by the following claims.

What is claimed is:

1. A compound of formula (I),

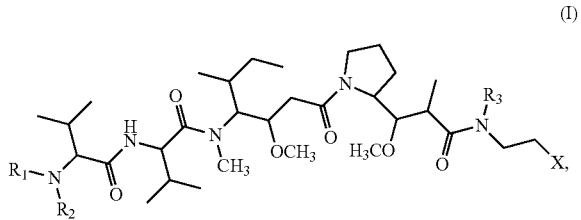

or a pharmaceutically acceptable salt thereof, wherein $R_1$ is selected from H, $(C_1-C_6)$ alkyl, $(C_2-C_6)$ alkenyl, $(C_2-C_6)$ alkynyl, a Protecting Group or a Linker Unit;

$R_2$ is selected from H, $(C_1-C_6)$ alkyl, $(C_2-C_6)$ alkenyl or $(C_2-C_6)$ alkynyl;

$R_3$ is H or $(C_1-C_6)$ alkyl; and

X is a bicyclic heterocyclic ring system selected from quinolinyl, isoquinolinyl, 1,5-naphthyridinyl, quinoxalinyl, quinazolinyl, cinnolinyl, 2,7-naphthyridinyl, 1,8-naphthyridinyl, 2,6-naphthyridinyl, phthalazinyl, 2H-chromenyl, 1H-1,5-benzodiazepinyl, 1,2,3-benzotriazinyl and 2,5-benzodiazocinyl, wherein the bicyclic heterocyclic ring system is unsubstituted or substituted with 1, 2 or 3 substituent(s) selected from $(C_1-C_6)$ alkoxy, methylene dioxy, hydroxyl, O-Protecting Group and O-Linker Unit.

2. The compound of claim 1, wherein the compound has formula (Ia):

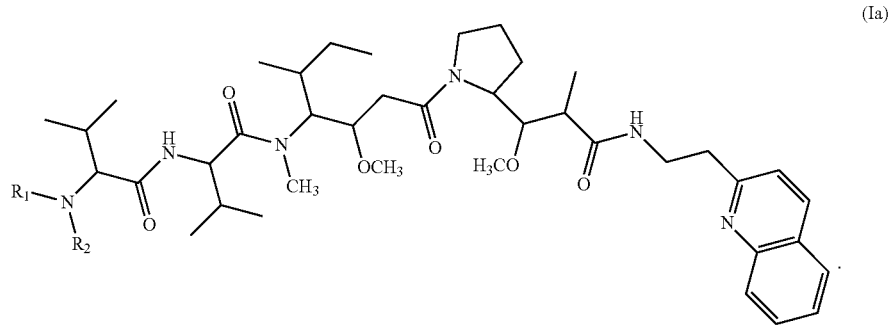

3. The compound of claim 1, wherein the compound has formula (Ib):
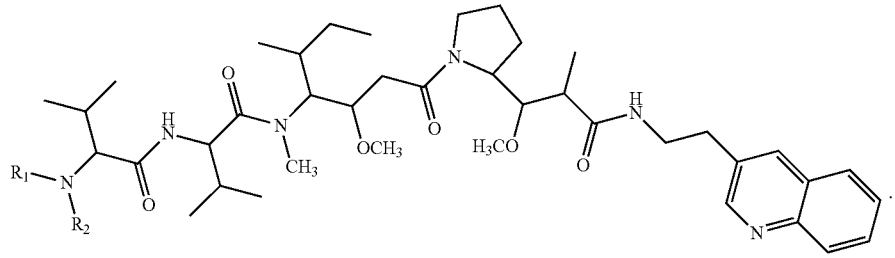
(Ib)
4. The compound of claim 1, wherein the compound has formula (Ic):
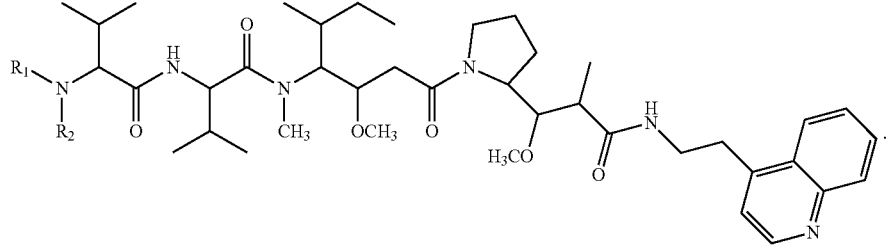
(Ic)
5. The compound of claim 1, wherein the compound has formula (Id):
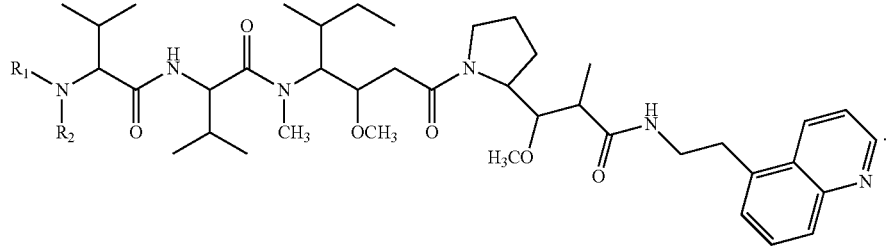
(Id)
6. The compound of claim 1, wherein the compound has formula (Ie):
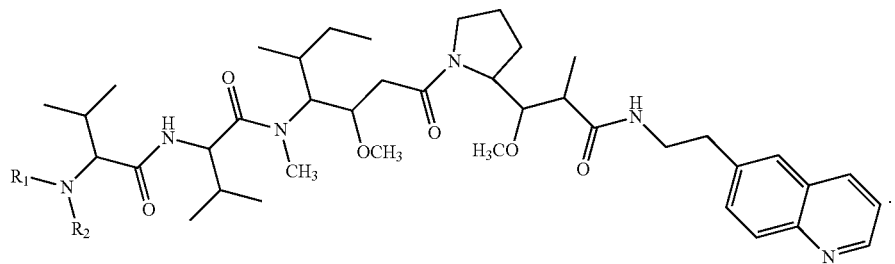
(Ie)

7. The compound of claim 1, wherein the compound has formula (If):

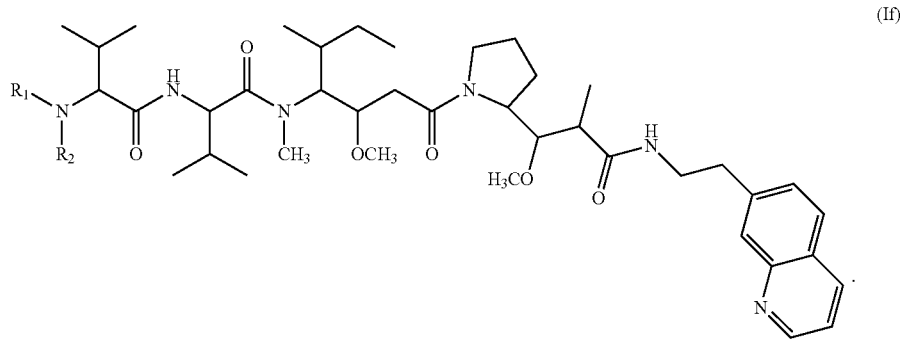

(If)

8. The compound of claim 1, wherein the compound has formula (Ig):

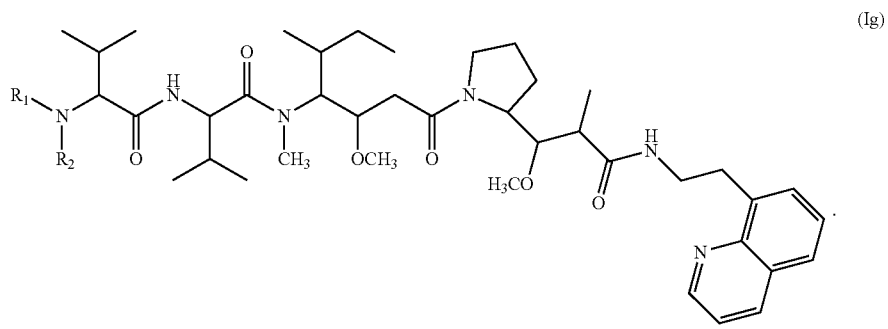

(Ig)

9. The compound of claim 1, wherein $R_1$ is H, ($C_1$-$C_6$) alkyl or a Linker Unit.

10. The compound of claim 1, wherein $R_2$ is H or ($C_1$-$C_6$) alkyl.

11. The compound of claim 1, wherein the Linker Unit has formula:

$A_a W_w Y_y$, wherein $A_a$ is maleimidocaproyl, $W_w$ is Valine-Citrulline and $Y_y$ is p-aminobenzyloxycarbonyl.

12. A compound selected from the group consisting of:

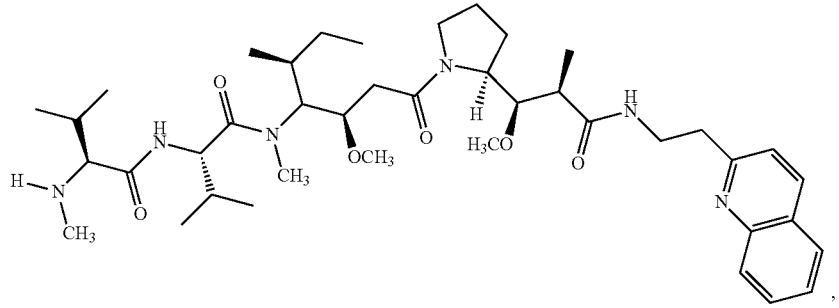

,

-continued
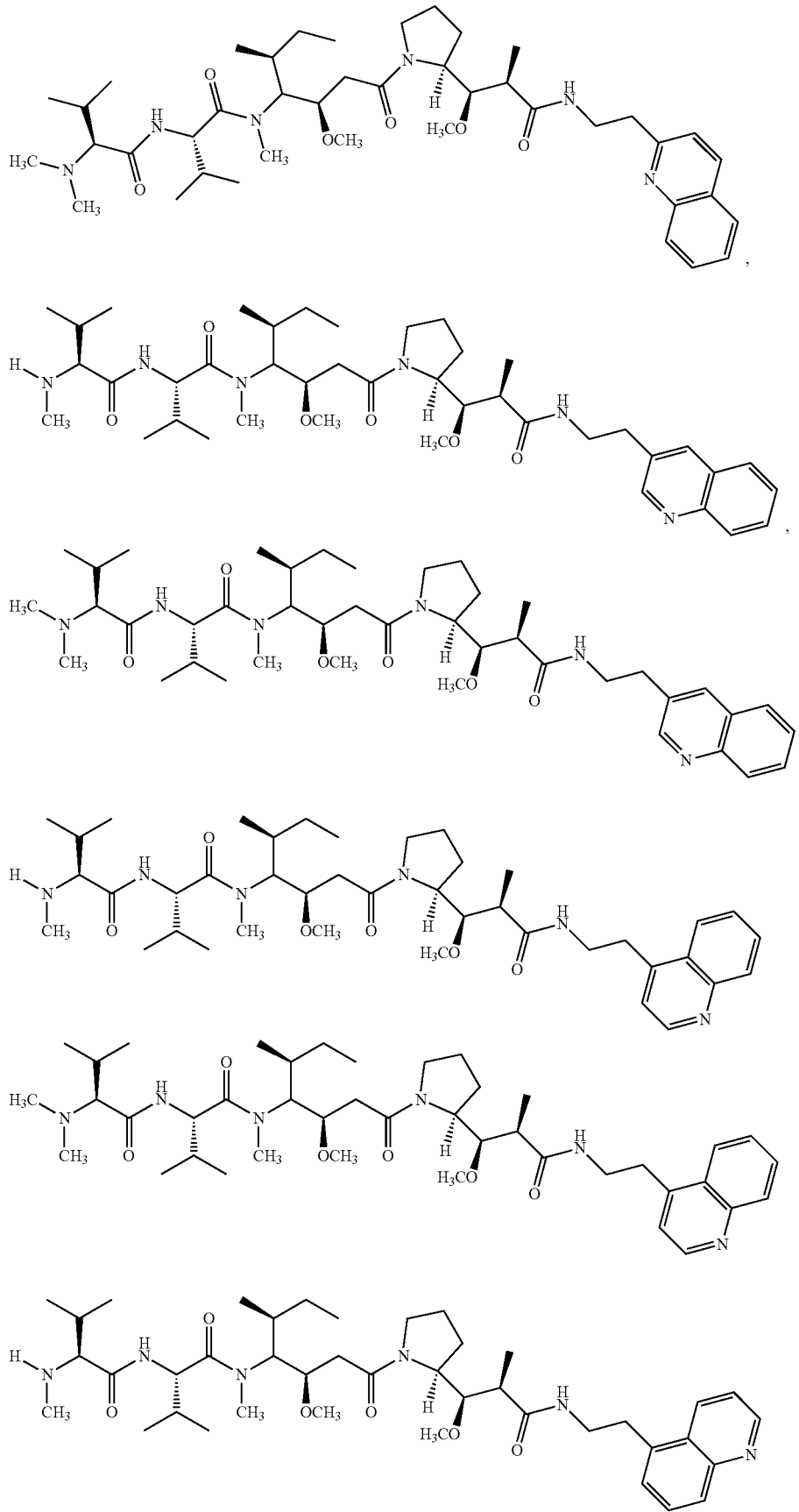

-continued
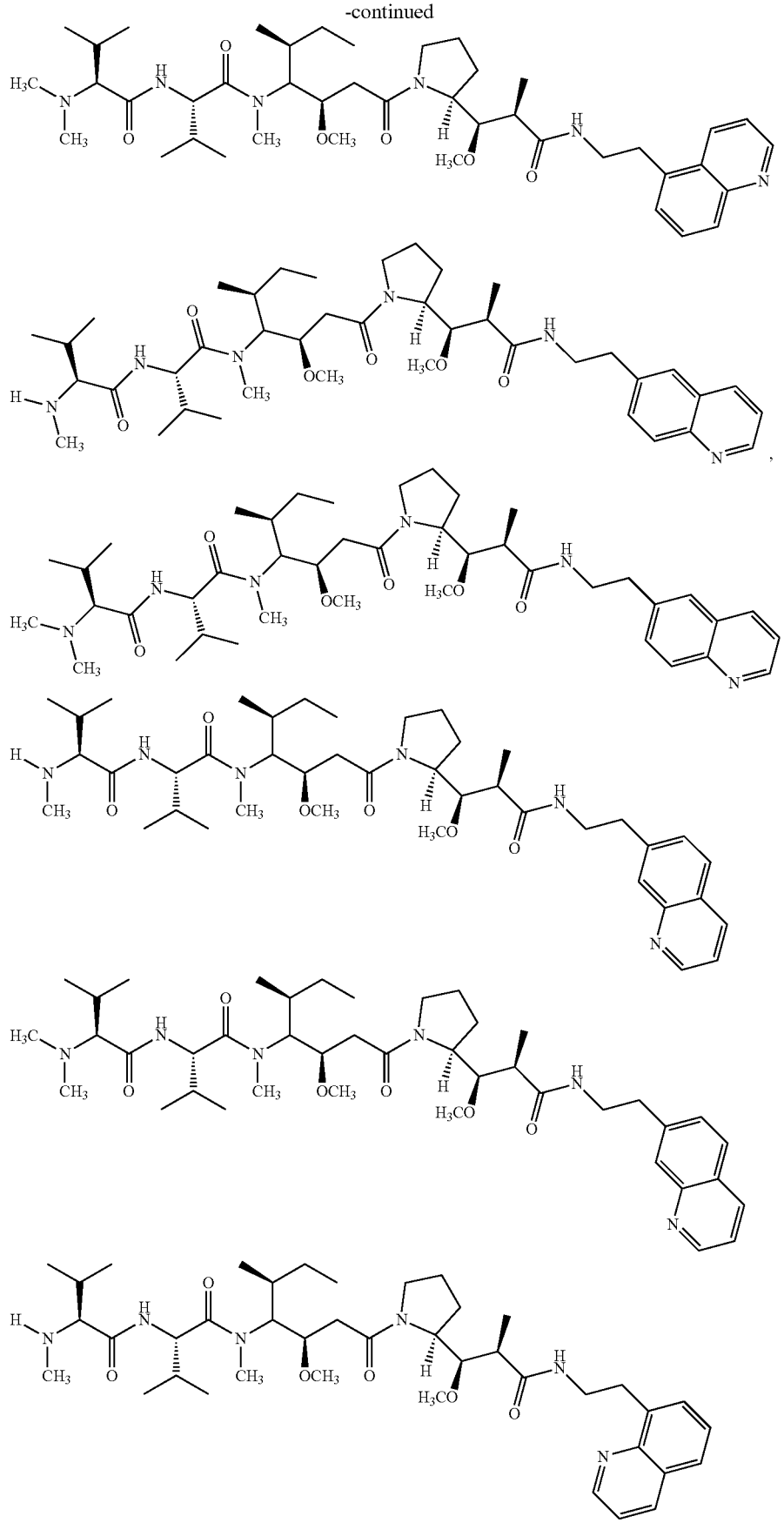

-continued
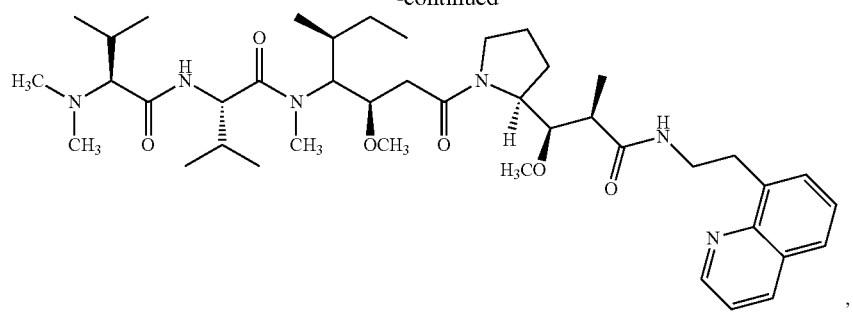
,
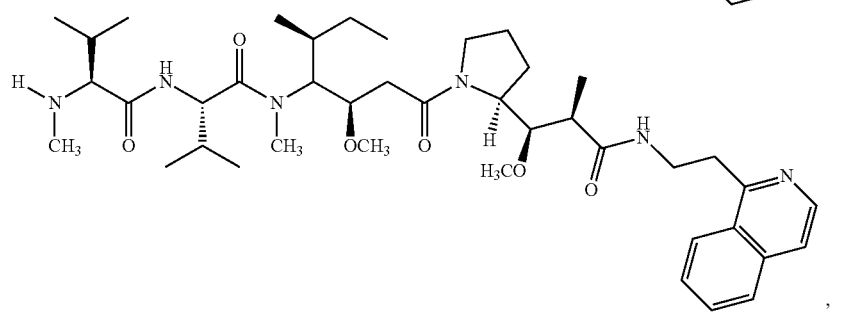
,
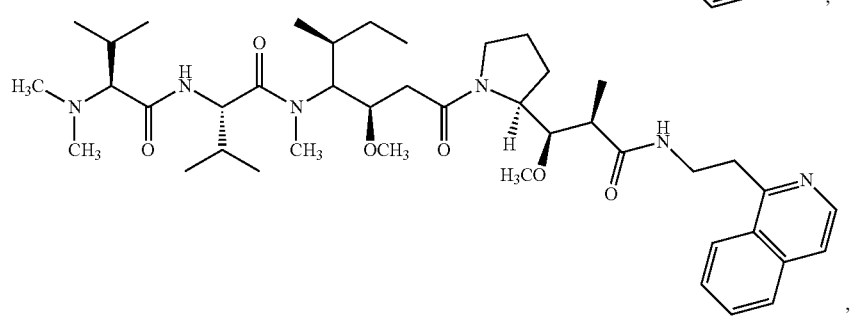
,
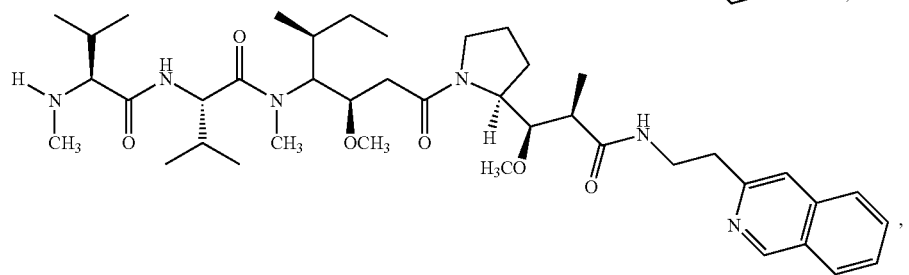
,
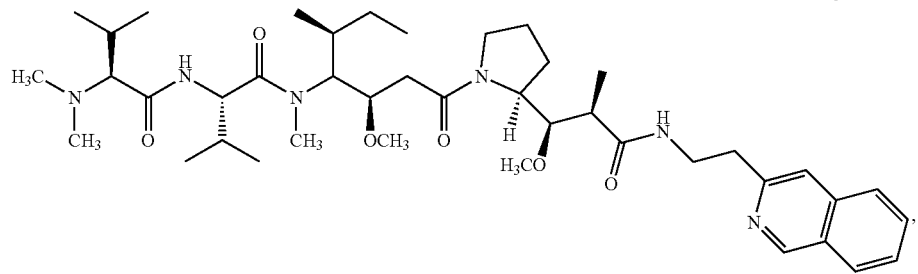
,
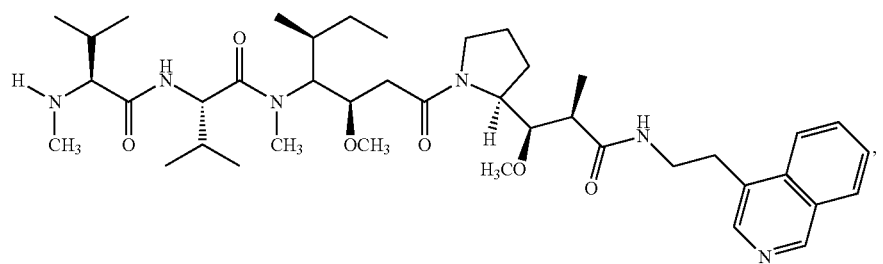
, -continued
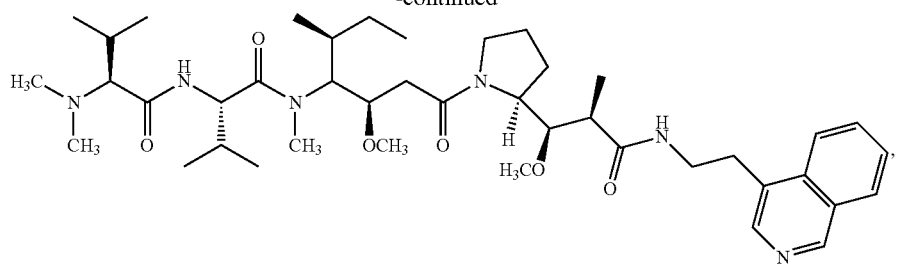
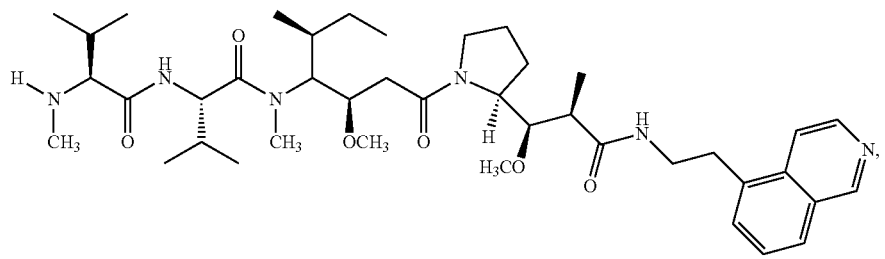
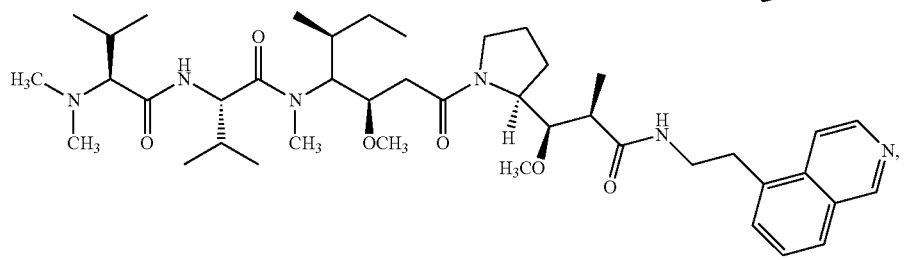
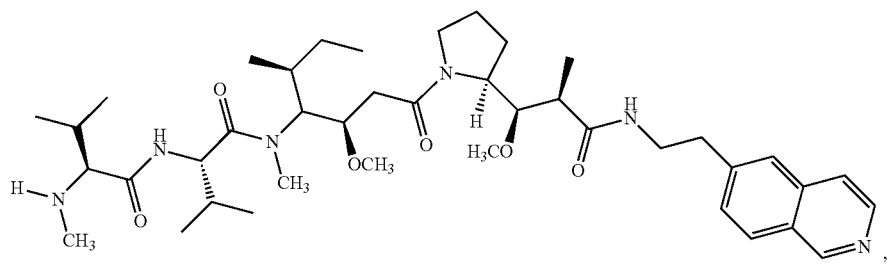
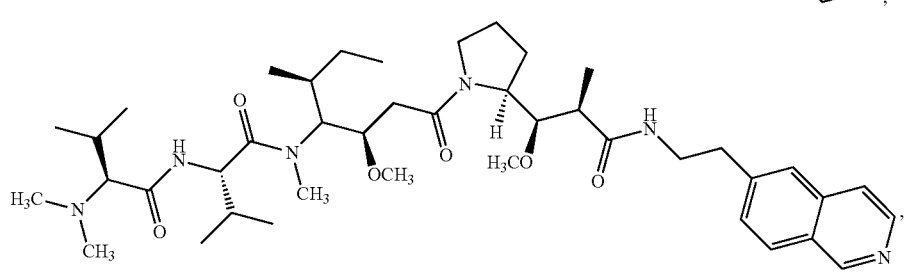
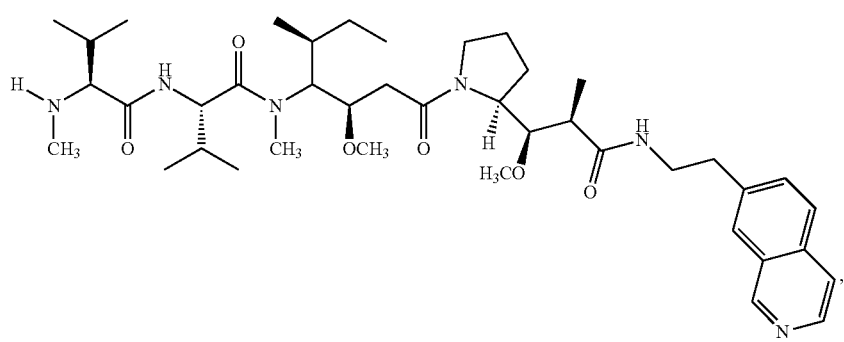

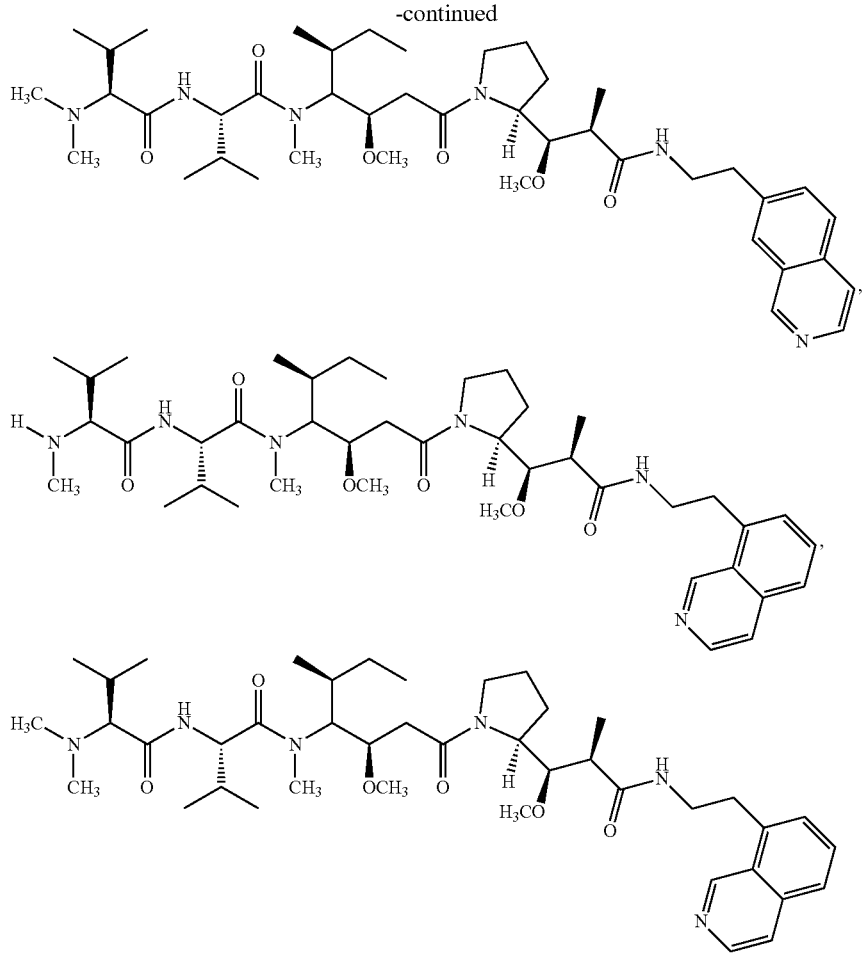

and pharmaceutically acceptable salts thereof.

13. A pharmaceutical composition comprising a compound of claim 1 or a pharmaceutically acceptable salt thereof and a pharmaceutically acceptable carrier.

14. An article of manufacture comprising the compound of claim 1, a container, and a package insert or label indicating that the compound can be used to treat cancer characterized by the overexpression of at least one tumor-associated antigen.

15. A method for killing or inhibiting the proliferation of tumor cells or cancer cells comprising treating the tumor cells or cancer cells with a compound of claim 1, or a pharmaceutical composition of claim 13, in an amount effective to kill or inhibit the proliferation of the tumor cells or cancer cells.

16. A method for treating cancer in a patient in need thereof comprising administering to the patient a compound of claim 1, or a pharmaceutical composition of claim 13, wherein the compound or pharmaceutical composition is administered in an amount effective to treat cancer.

17. A method of determining inhibition of cellular proliferation by a compound, comprising contacting cells in a cell culture medium with the compound of claim 1 and measuring the cytotoxic activity of the compound, whereby proliferation of the cells is inhibited.

18. A method of inhibiting the growth of tumor cells that overexpress a tumor-associated antigen comprising administering to a patient the compound of claim 1 conjugated to an antibody that is specific for said tumor-associated antigen, and optionally a second therapeutic agent wherein the compound and the second therapeutic agent are each administered in amounts effective to inhibit the growth of tumor cells in the patient.

* * * * *